(12) United States Patent
Arai et al.

(10) Patent No.: US 10,629,826 B2
(45) Date of Patent: Apr. 21, 2020

(54) ORGANIC COMPOUND AND PHOTOELECTRIC CONVERSION ELEMENT

(71) Applicants: RICOH COMPANY, LTD., Tokyo (JP); KYUSHU UNIVERSITY, NATIONAL UNIVERSITY CORPORATION, Fukuoka (JP)

(72) Inventors: Ryota Arai, Shizuoka (JP); Takuma Yasuda, Fukuoka (JP); Yu Hidaka, Fukuoka (JP); Woong Shin, Fukuoka (JP)

(73) Assignees: RICOH COMPANY, LTD., Tokyo (JP); KYUSHU UNIVERSITY, NATIONAL UNIVERSITY CORPORATION, Fukuoka (JP)

( * ) Notice: Subject to any disclaimer, the term of this patent is extended or adjusted under 35 U.S.C. 154(b) by 81 days.

(21) Appl. No.: 15/059,404

(22) Filed: Mar. 3, 2016

(65) Prior Publication Data
US 2016/0260912 A1    Sep. 8, 2016

(30) Foreign Application Priority Data

Mar. 6, 2015 (JP) ................................ 2015-044404
Mar. 20, 2015 (JP) ................................ 2015-057798

(51) Int. Cl.
*H01L 51/00* (2006.01)
*C07D 495/04* (2006.01)
(Continued)

(52) U.S. Cl.
CPC ........ *H01L 51/0074* (2013.01); *C07D 495/04* (2013.01); *H01L 51/0053* (2013.01);
(Continued)

(58) Field of Classification Search
CPC ............... H01L 51/0074; H01L 51/424; H01L 51/0068; H01L 51/0053; H01L 51/4233;
(Continued)

(56) References Cited

U.S. PATENT DOCUMENTS

2014/0083479 A1* 3/2014 Takayama ............. H01L 51/447
136/246
2014/0124035 A1* 5/2014 Byrne ................... C08G 61/123
136/263
(Continued)

FOREIGN PATENT DOCUMENTS

| JP | 2014-177409 | 9/2014 | |
|---|---|---|---|
| JP | 2015-196661 | 11/2015 | |
| WO | WO 2011085004 A2 * | 7/2011 | ............ C08G 61/123 |

OTHER PUBLICATIONS

Yuang-Tung Cheng, "Improvement of organic solar cells by flexible substrate and ITO surface treatments" Applied Surface Science 256 (2010) 7606-7611.*
(Continued)

*Primary Examiner* — Michael Y Sun
(74) *Attorney, Agent, or Firm* — Oblon, McClelland, Maier & Neustadt, L.L.P.

(57) ABSTRACT

To provide an organic compound represented by the following general formula (1):
(Continued)

<General Formula (1)> where $R_1$ is a C2-C6 alkyl group or a hydrogen atom, $R_2$ and $R_3$, which may be identical or different, are each a C2-C12 alkyl group, and $R_4$ and $R_5$, which may be identical or different, are each a C6-C12 alkyl group that may be a branched chain or a straight chain.

21 Claims, 1 Drawing Sheet

(51) Int. Cl.
  *H01L 51/42* (2006.01)
  *C07D 333/52* (2006.01)
  *C07D 333/76* (2006.01)
  *C07D 333/72* (2006.01)

(52) U.S. Cl.
  CPC ...... *H01L 51/0068* (2013.01); *H01L 51/4233* (2013.01); *C07D 333/52* (2013.01); *C07D 333/72* (2013.01); *C07D 333/76* (2013.01); *H01L 51/0036* (2013.01); *H01L 2251/308* (2013.01); *Y02E 10/549* (2013.01)

(58) Field of Classification Search
  CPC .......... H01L 51/0036; H01L 2251/308; C07D 495/04; C07D 333/72; C07D 333/76; C07D 333/52; Y02E 10/549
  See application file for complete search history.

(56) References Cited

U.S. PATENT DOCUMENTS

2015/0280142 A1   10/2015   Arai et al.
2015/0311364 A1*  10/2015   Wu ..................... H01L 51/0003
                                                     438/82

OTHER PUBLICATIONS

Yuanjing Cui "An indanone-based alkoxysilane dye with second order nonlinear optical properties" Dyes and Pigments 81 (2009) 53-57.*
Suling Shen "Solution-Processable Organic Molecule Photovoltaic Materials with ithienyl-benzodithiophene Central Unit and Indenedione End roups" Chem. Mater. 2013, 25, 2274-2281.*
Vellaiappillai Tamilavan "Pyrrolo[3,4-c]pyrrole-1,3-dione-Based Large Band Gap Polymers Containing Benzodithiophene Derivatives for Highly Efficient Simple Structured Polymer Solar Cells" Journal of Polymer Science, Part A: Polymer Chemistry 2014, 52, 3564-3574 Article www.polymerchemistry.org Journal of Polymer Science.*
Yi Zhang "Synthesis and photovoltaic properties of two-dimension-conjugated D—A copolymers based on benzodithiophene or benzodifuran units" Polym. Chem., 2013, 4, 1474.*
Ning Wang, "Fluorinated Benzothiadiazole-Based Conjugated Polymers for High-Performance Polymer Solar Cells without Any Processing Additives or Post-treatments" J. Am. Chem. Soc. 2013, 135, 17060-17068.*
Hao Chen, "Novel Fluorene-based Conjugated Copolymers with Donor-acceptor Structures for Photovoltaic Applications" Polymer Bulletin 60, 581-590 (2008).*
Chul Young Kim, "Poly(1,4-bis((E)-2-(3-dodecylthiophen-2-yl)vinyl)benzene) for Solution Processable Organic Thin Film Transistor" Bull. Korean Chem. Soc. 2012, vol. 33, No. 5 1659.*
Masaya Hirade "Effects of Intramolecular Donor-Acceptor Interactions on Bimolecular Recombination in Small-Molecule Organic Photovoltaic Cells" J. Phys. Chem. C 2013, 117, 4986-4991.*
Hung-Yang Chen "Rare solvent annealing effective benzo(1,2-b:4,5-b) dithiophene-based low band-gap polymer for bulk heterojunction organic photovoltaics" Chem. Commun., 2012, 48, 1012-1014 (Year: 2012).*
Panasonic Electric Works Technical Report, 56 (2008) 87.
Nature, 353 (1991) 737.
J.Am.Chem.Soc., 115 (1993) 6382.
Adv.Mater. 2013, 25, 2397-2402.
Chem. Mater. 2013, 25, 2274-2281.

* cited by examiner

ORGANIC COMPOUND AND PHOTOELECTRIC CONVERSION ELEMENT

CROSS-REFERENCE TO RELATED APPLICATIONS

The present application claims priority under 35 U.S.C. § 119 to Japanese Patent Application No. 2015-044404, filed on Mar. 6, 2015 and Japanese Patent Application No. 2015-057798, filed on Mar. 20, 2015. The contents of which are incorporated herein by reference in their entirety.

BACKGROUND OF THE INVENTION

Field of the Invention

The present invention relates to organic compounds and photoelectric conversion elements.

Description of the Related Art

In recent years, the power required for driving electric circuits has become extremely low. Preparing for the coming IoT society, various electronic parts, such as sensors, have been able to be driven with very low electric power (order of µW). As for utilization of a sensor, applications for an energy harvesting element has been expected as a self-sufficient energy supply capable of generate and consume power in-situ. Among the energy harvesting elements, photoelectric conversion elements have been attracted attentions as an element capable of generating power anywhere as long as there is light. As an energy harvesting element, particularly demanded is a photoelectric conversion element capable of efficiently generating electric power with weak light. Typical examples of weak light include LED light, and light of a fluorescent lamp. These are typically used indoor, and are called indoor lighting. The illuminance of these types of light is from about 20 lux through about 1000 lux, and these are very weak light compared to direct sunlight (about 100,000 lux). As an energy harvesting element, there is a need for an element capable of efficiently generating energy with indoor lighting, such as a fluorescent lamp, and an LED lamp.

As the photoelectric conversion element, the most widely used is a silicon-based battery cell. Various silicon-based battery cells having high conversion efficiency under sunlight have been reported (for example, Panasonic Electric Works Technical Report, 56 (2008) 87). However, it has been generally known that the silicon-based solar cell has low conversion efficiency under weak light, through the silicon-based solar cell has excellent conversion efficiency with sun light (for example, Nature, 353 (1991) 737). Meanwhile, it is reported that a dye-sensitized solar cell presented by Graetzel et al. of Swiss Federal Institute of Technology in Lausanne has photoelectric conversion properties better than silicon solar cells, under weak light (see, for example, J. Am. Chem. Soc., 115 (1993) 6382). Moreover, it is also known that a bulk heterojunction organic thin solar battery, in which a p-type organic semiconductor developed by Heeger et al., and a n-type organic semiconductor, such as fullerene, are mixed, has relatively high power generating ability with weak light (Adv. Mater. 2013, 25, 2397-2402).

It is known associated with properties of a photoelectric conversion element that open-circuit voltage is typically largely reduced, as the light intensity is reduced. This reduction in the open-circuit voltage is a significant factor for degrading the properties of a solar cell under weak light. The tendency mentioned above is also applied for conventional organic thin-film solar cells. Therefore, there is a need for improving the low open-circuit voltage under weak light.

Moreover, it is known that a short-circuit current density, which is one of properties of a photoelectric conversion element, is proportional to a light intensity, if the light source for use is the same. This tendency as mentioned is also applied for a so-called organic thin-film solar cell. Conventional organic thin-film solar cells have been developed to use sun light as a light source. Among them, development of p-type organic semiconductors has been particularly actively conducted.

Meanwhile, a photoelectric conversion element, a light source of which is indoor lighting, needs to exhibit a high electric current value with a fluorescent lamp, or an LED lamp, because the light used is a fluorescent lamp or an LED lamp, not sunlight. Unlike sunlight, light emitted from a fluorescent lamp or LED lamp has a spectrum only in visible light region. A p-type organic semiconductor used in a conventional photoelectric conversion element designed to use with sunlight does not match with the spectrum of the fluorescent lamp or LED lamp very well, and thus use of such the p-type organic semiconductor in the photoelectric conversion element leads to a low electric current value with light of a fluorescent lamp or LED lamp. Accordingly, it is desired to develop a material suitable for a spectrum of light of a fluorescent lamp or LED lamp. Specifically, there is a need for a material having an absorption spectrum present at the shorter wavelength side to an absorption spectrum of a p-type organic semiconductor designed to use with sunlight.

The literature "Chem. Mater. 2013, 25, 2274-2281" discloses a material whose absorption wavelengths are relatively short wavelengths, and discloses an organic material exhibits a relatively high electric current value under simulated sunlight. However, this literature does not teach properties of the material with low illuminance.

Moreover, a p-type organic semiconductor used in a bulk heterojunction organic thin-film solar cell is formed into a film through a solution coating process. Therefore, the p-type organic semiconductor is desired to have high dissolvability. Especially in the case where it is desired to make a film thickness large, and sufficiently perform light absorption, the higher dissolvability of the p-type organic semiconductor is required. In order to adjust absorption wavelengths of a low-molecular p-type organic semiconductor, moreover, a method for introducing an acceptor segment is often used. In this case, the dissolvability of the p-type organic semiconductor tends to be lowered, and thus there is a problem where the p-type organic semiconductor is not dissolved in a solvent used for film formation. For the purpose of solving the aforementioned problem, a long-chain alkyl group is introduced into a skeleton of the p-type semiconductor. In the aforementioned literature, an acceptor segment is introduced, and a long-chain alkyl group is introduced to secure dissolvability.

However, the aforementioned conventional organic material does not have sufficient dissolvability, and hence cannot be suited for formation of a thick film.

SUMMARY OF THE INVENTION

The present invention aims to provide an organic compound (p-type organic semiconductor), which generates high open-circuit voltage even with very weak light, such as indoor lighting.

As the means for solving the aforementioned problems, the organic compound of the present invention is represented by the following general formula (1).

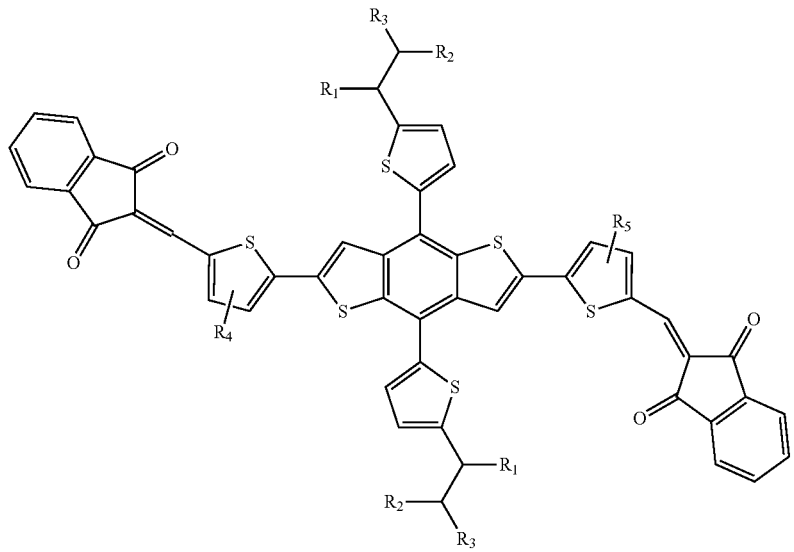

<General Formula (1)>

In the general formula (1), $R_1$ is a C2-C6 alkyl group or a hydrogen atom, $R_2$ and $R_3$, which may be identical or different, are each a C2-C12 alkyl group, and $R_4$ and $R_5$, which may be identical or different, are each a C6-C12 alkyl group that may be a branched chain or a straight chain.

Moreover, the organic compound of the present invention is represented by the following general formula (2).

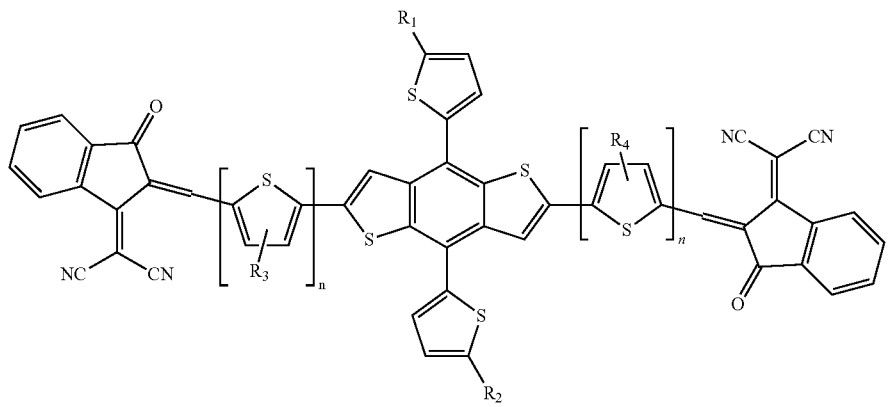

<General Formula (2)>

In the general formula (2), $R_1$ and $R_2$, which may be identical or different, are each a C6-C22 alkyl group that may be a branched chain or a straight chain, $R_3$ and $R_4$, which may be identical or different, are each a hydrogen atom or a C2-C16 alkyl group that may be a branched chain or a straight chain, and n is an integer of 1, 2, or 3.

The present invention can provide an organic compound (p-type organic semiconductor), which generates high open-circuit voltage even with very weak light, such as indoor lighting.

DETAILED DESCRIPTION OF THE INVENTION

Figure 1:
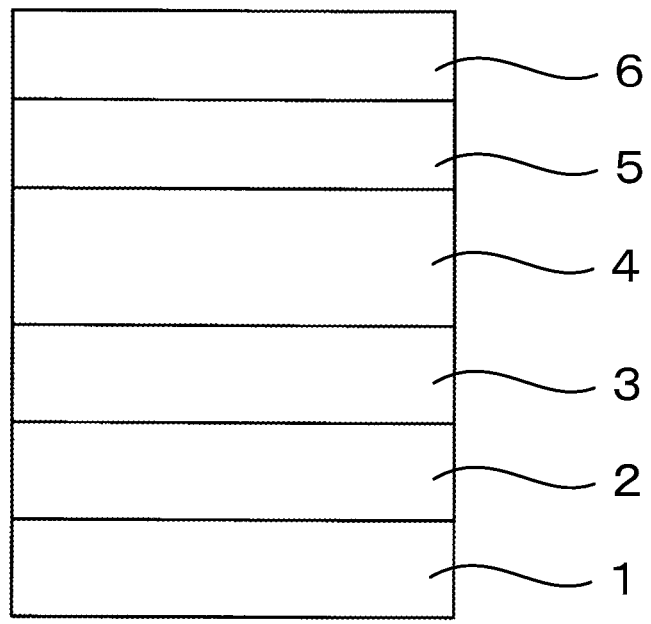
FIG. 1 is a schematic view illustrating one example of the photoelectric conversion element of the present invention.

The organic compound and photoelectric conversion element according to the present invention are described with reference to drawings hereinafter.

Note that, the present invention is not limited to the embodiments described hereinafter, and another embodiments, additions to the embodiments, eliminations from the embodiments are also included in the present invention, as long as these changes are made within the scope at which a person skilled in the art can easily arrive, and any of these embodiments can exhibits functions and effects of the present invention.

In the present specification, the term "photoelectric conversion element" denotes an element, which converts optical energy into electric energy, or an element, which convers electric energy into optical energy. Specific examples of the photoelectric conversion element include a solar battery, and a photodiode.

The details are described hereinafter.

<Organic Compound>

In a first embodiment, the organic compound of the present invention is represented by the following general formula (1). The compound represented by the general formula (1) is an organic compound, which is highly soluble, and exhibits high conversion efficiency with weak light, such as indoor lighting.

<General Formula (1)>

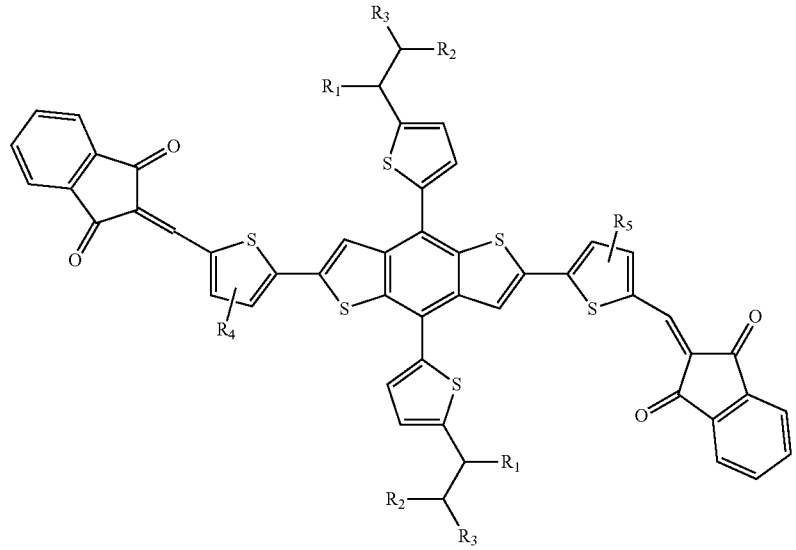

In the general formula (1), $R_1$ is a C2-C6 alkyl group or a hydrogen atom, $R_2$ and $R_3$, which may be identical or different, are each a C2-C12 alkyl group, and $R_4$ and $R_5$, which may be identical or different, are each a C6-C12 alkyl group that may be a branched chain or a straight chain.

$R_1$ is a hydrogen atom or a C2-C6 alkyl group, and examples of the alkyl group include an ethyl group, a propyl group, a butyl group, a pentyl group, and a hexyl group. $R_1$ is preferably a hydrogen atom.

$R_2$ is a C2-C12 alkyl group, and examples of the alkyl group include the groups listed above, an octyl group, and a decyl group. $R_2$ is preferably an ethyl group.

$R_3$ is a C2-C12 alkyl group, and examples of the alkyl group include the groups listed above, an octyl group, and a decyl group. $R_3$ is preferably a butyl group.

$R_4$ and $R_5$ are each a C6-C12 alkyl group, and examples of the alkyl group include a hexyl group, an octyl group, a decyl group, and a dodecyl group. $R_4$ and $R_5$ are each preferably a hexyl group.

Specific examples of the organic compound represented by the general formula (1) include the compounds represented by the following structural formulae. However, the present invention is not limited to these examples.

Exemplary Compound 1-1
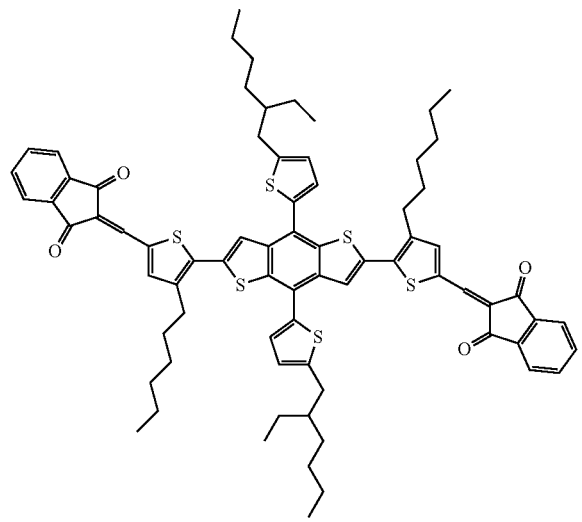
Exemplary Compound 1-2
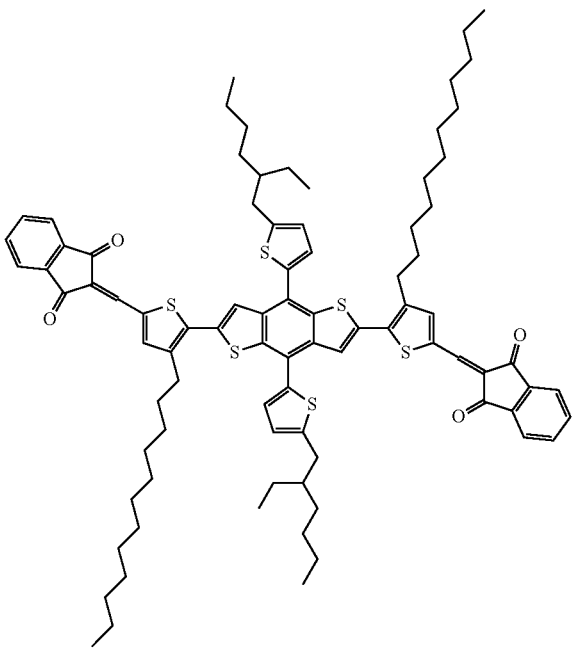
Exemplary Compound 1-3
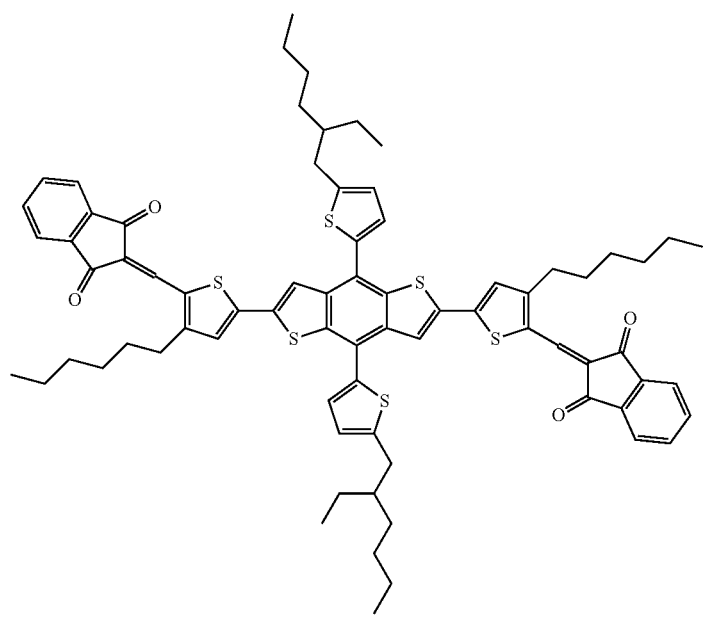

Exemplary Compound 1-4
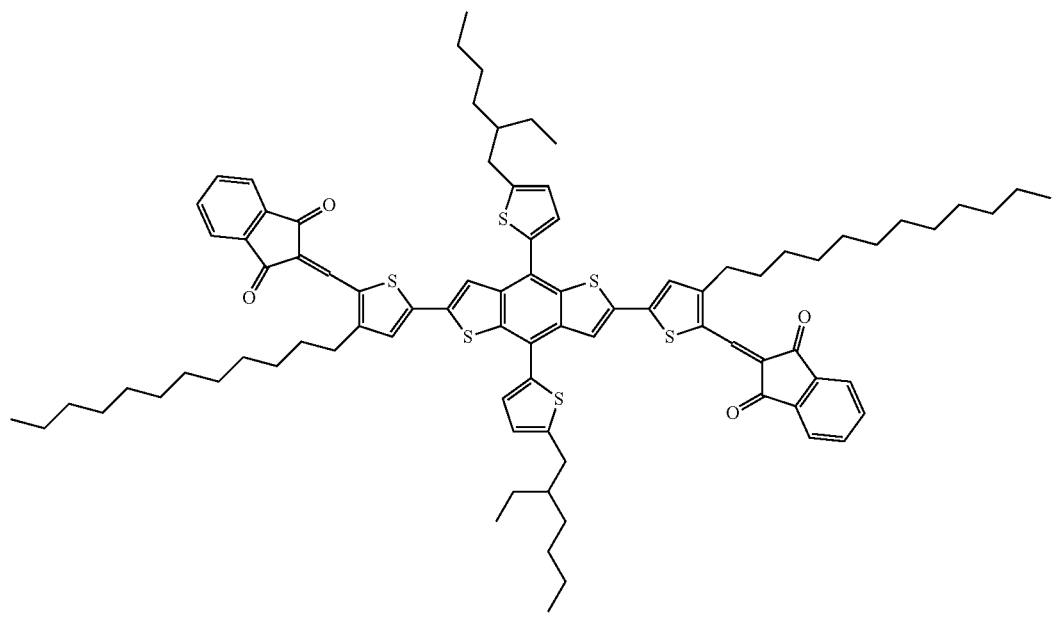
Exemplary Compound 1-5
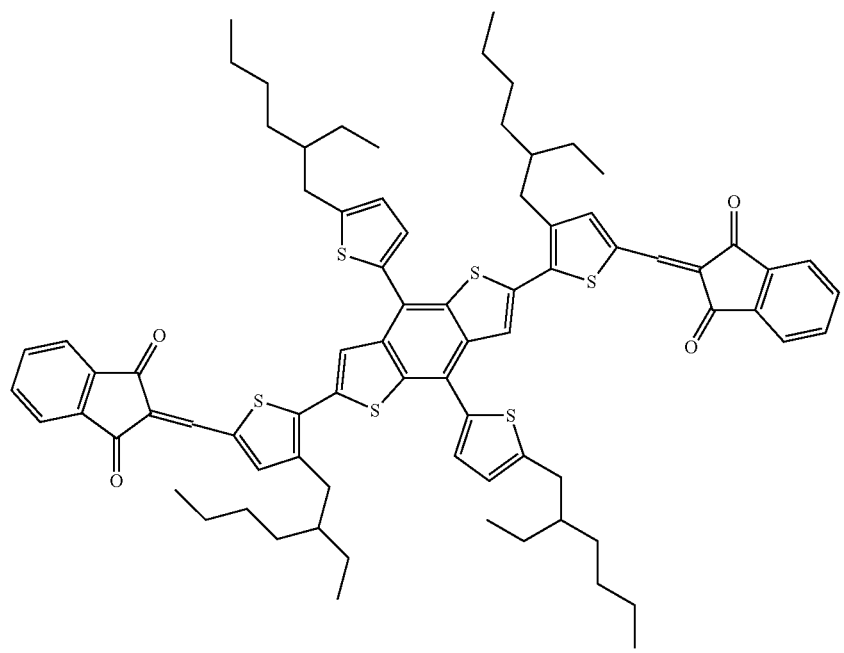

-continued
Exemplary Compound 1-6
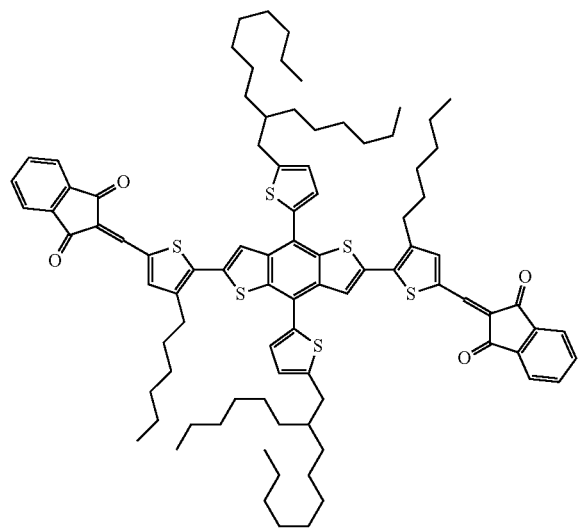
Exemplary Compound 1-7
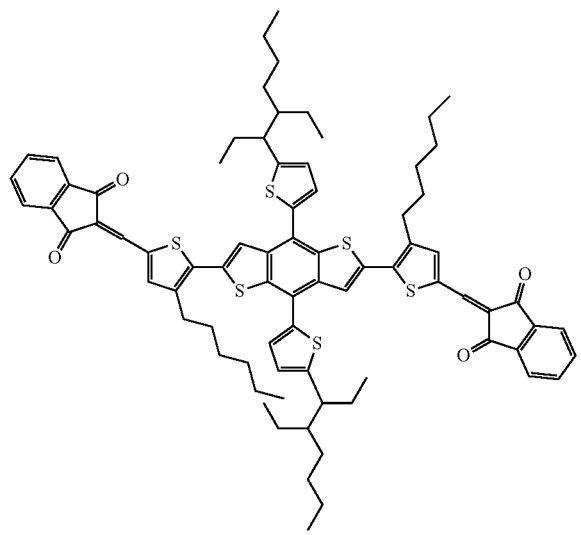
Exemplary Compound 1-8
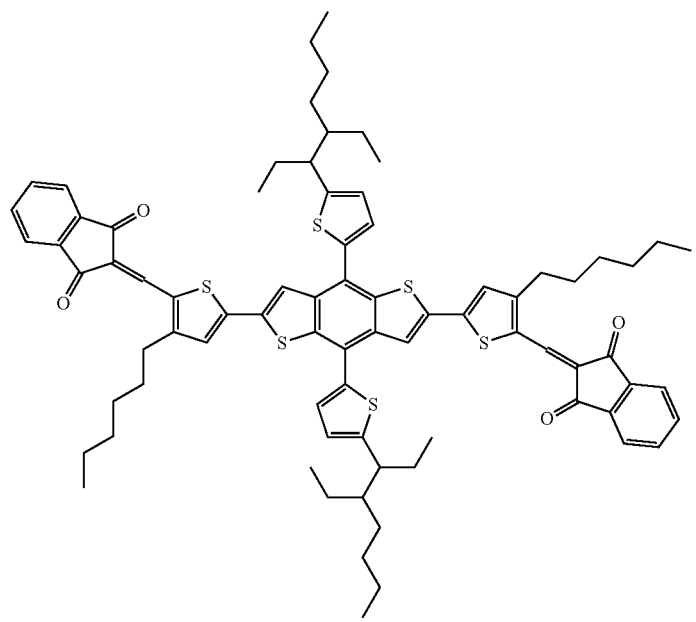
For example, the organic compound represented by the general formula (1) can be synthesized by the following steps.
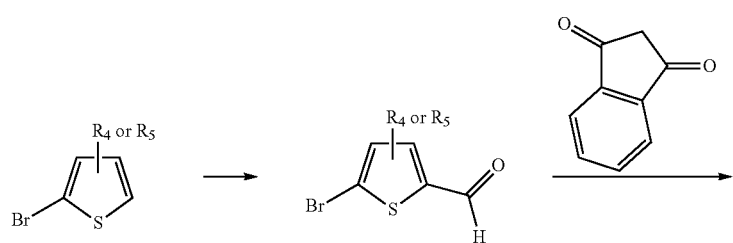

-continued

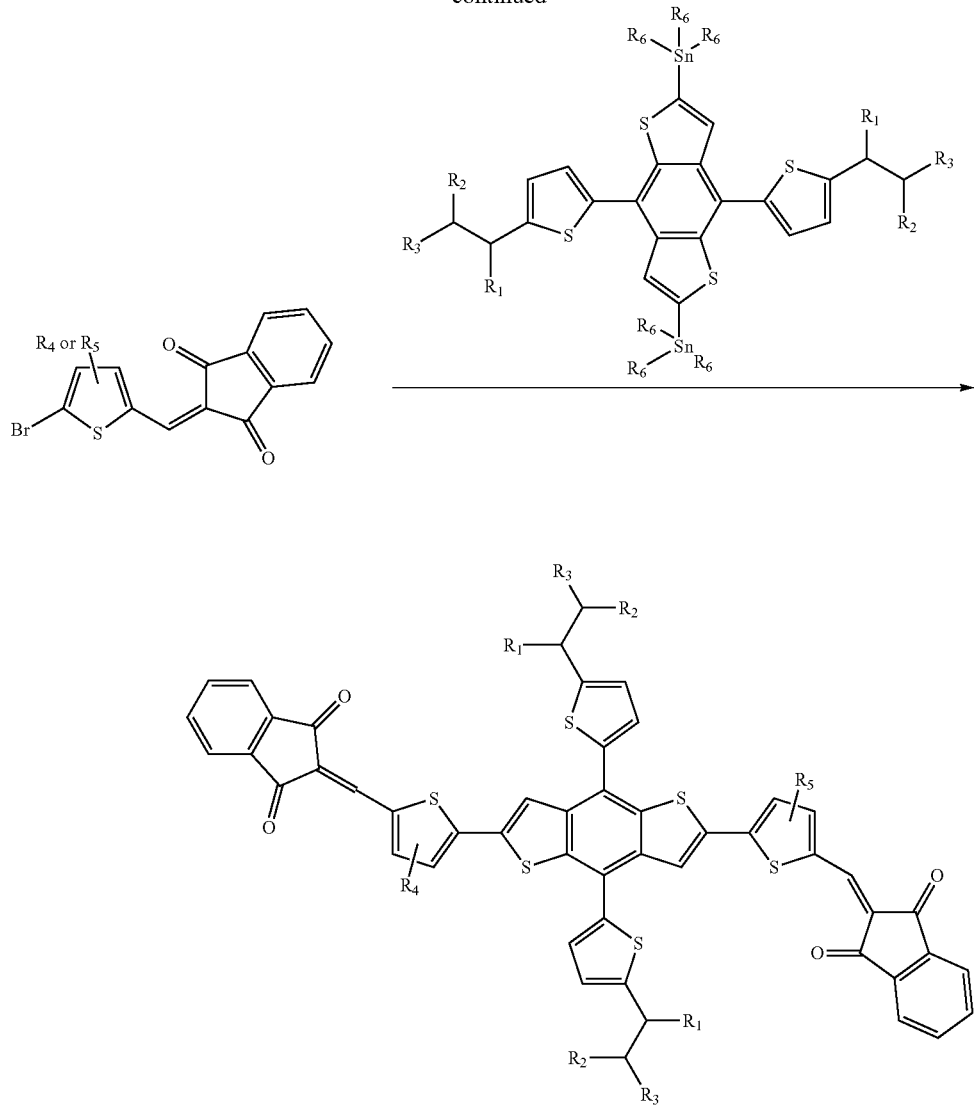

(First Step)

Bromothiophene, in which 3- or 4-position of thiophene is alkylated, is formylated at 5-position, to thereby obtain a thiophene derivative including a formyl group. As for a method of the formylation, a typical method is used. In particular, a method called Vilsmeier reaction, where formylation is performed with phosphorus oxychloride and dimethyl formamide or dimethyl formanilide, is preferable. Another example may be a method where a hydrogen abstraction reaction is carried out with an organic lithium compound having low nucleophilicity, such as lithium diisopropyl amide, followed by lithiation, and formylation is then performed with DMF.

(Second Step)

The obtained thiophene derivative including a formyl group and 1,3-indandione are subjected to dehydration condensation, to thereby obtain a brominated thiophene-indandione derivative. As for a method of the dehydration condensation, a typical method can be used. Examples thereof include: a method where the thiophene derivative including a formyl group and 1,3-indandione are heated in a solvent in the presence of an acid catalyst, such as acetic acid, and hydrochloric acid; and a method where the thiophene derivative including a formyl group and 1,3-indandione are heated in a solvent in the presence of an organic base catalyst, such as pyridine, and piperidine. In particular, a method where the thiophene derivative including a formyl group and 1,3-indandione are heated in acetic acid anhydride is preferable. As for the solvent, a typical solvent can be used. Examples of the solvent include toluene, chlorobenzene, THF, 1,4-dioxane, DMF, NMP, 1,2-dichloroethane, ethanol, and IPA.

(Third Step)

The obtained brominated thiophene-indandione derivative and an alkyltin-substituted benzodithiophene derivative are allowed to react through Stille coupling, to thereby obtain a compound represented by the general formula (1). As for the Stille coupling, a typical method disclosed in Org. React. 1997, 50, 1, can be used. $R_6$ is a C1-C4 alkyl group.

In a second embodiment, the organic compound of the present invention is represented by the following general formula (2). The compound represented by the general formula (2) is an organic compound (p-type organic semiconductor), which generates high open-circuit voltage with weak light, such as indoor lighting.

<General Formula (2)>

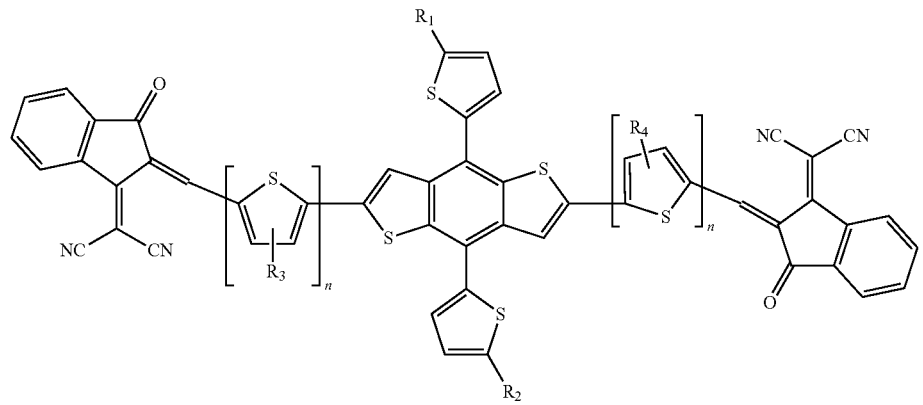

In the general formula (2), $R_1$ and $R_2$, which may be identical or different, are each a C6-C22 alkyl group that may be a branched chain or a straight chain, $R_3$ and $R_4$, which may be identical or different, are each a hydrogen atom or a C2-C16 alkyl group that may be a branched chain or a straight chain, and n is an integer of 1, 2, or 3.

Examples of the C6-C22 alkyl group represented by $R_1$ or $R_2$ include a hexyl group, an octyl group, a decyl group, a dodecyl group, a 2-ethylhexyl group, a 2-hexyldecyl group, and a 2-decyldodecyl group. Examples of the C2-C16 alkyl group represented by $R_3$ or $R_4$ include an ethyl group, a propyl group, a butyl group, a pentyl group, a hexyl group, an octyl group, a decyl group, a dodecyl group, a 2-ethylhexyl group, and a 2-hexyldecyl group. Among them, preferred as $R_1$ and $R_2$ are a 2-ethylhexyl group, and a 2-decyldodecyl group, and preferred as $R_3$ and $R_4$ are a hexyl group, a 2-ethylhexyl group, and a dodecyl group.

Specific examples of the organic compound represented by the general formula (2) include the compound represented by the following structural formulae. However, the present invention is not limited to these examples.

Exemplary Compound 2-1

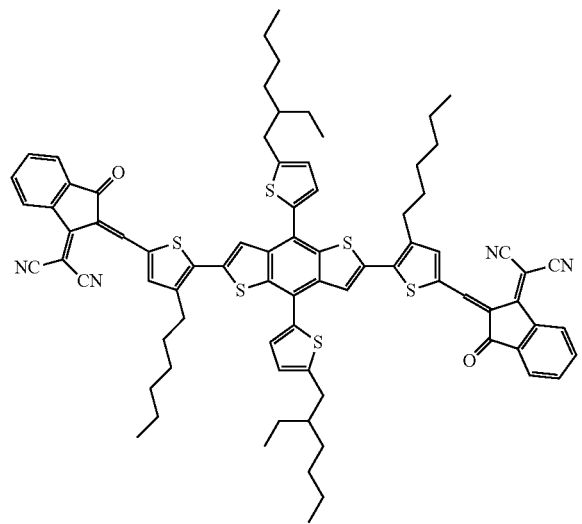

Exemplary Compound 2-2

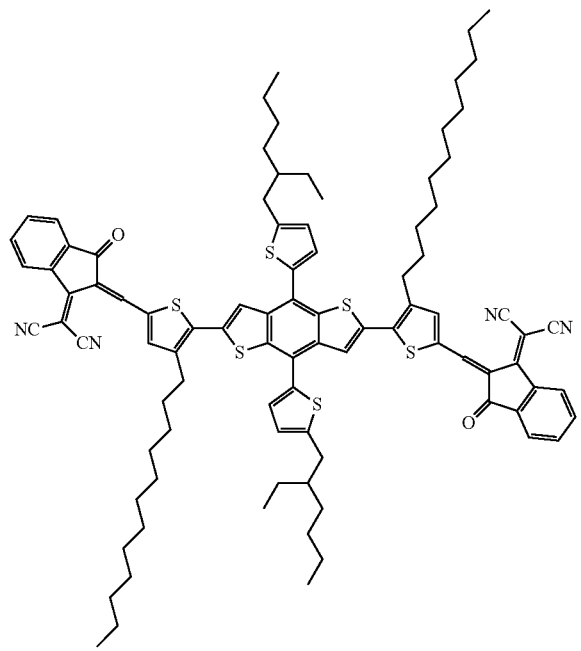

Exemplary Compound 2-3
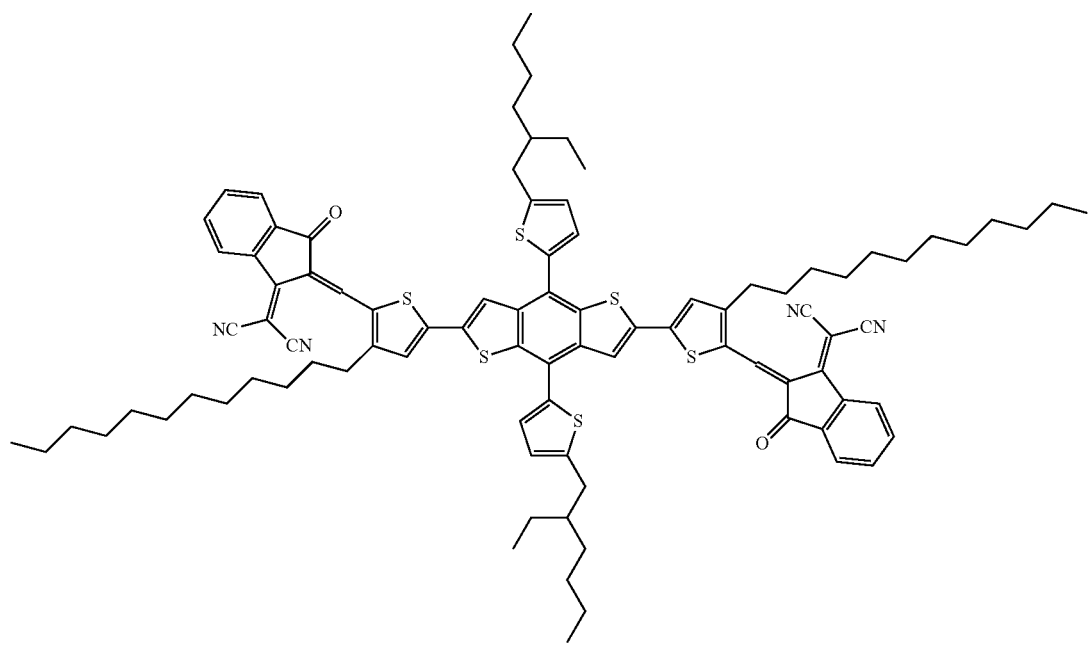
Exemplary Compound 2-4
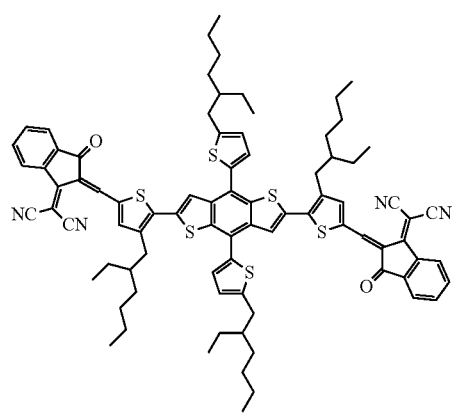
Exemplary Compound 2-5
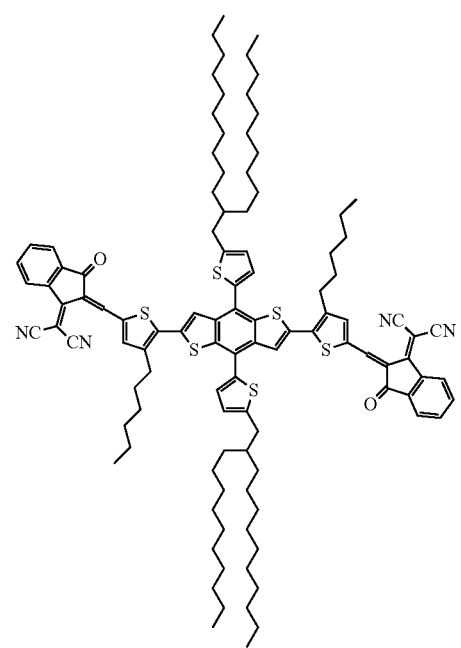

Exemplary Compound 2-6
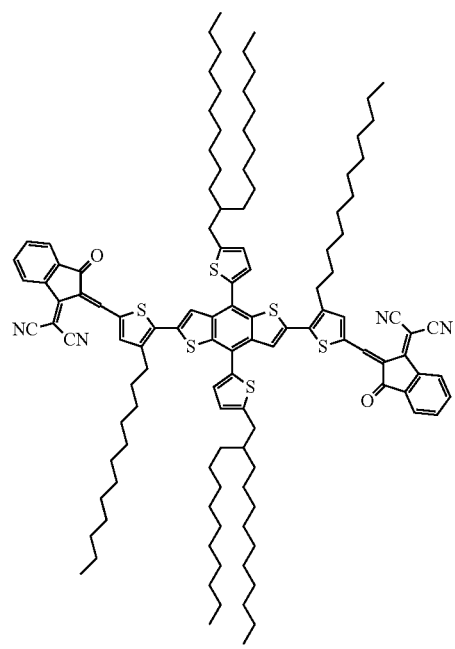
Exemplary Compound 2-7
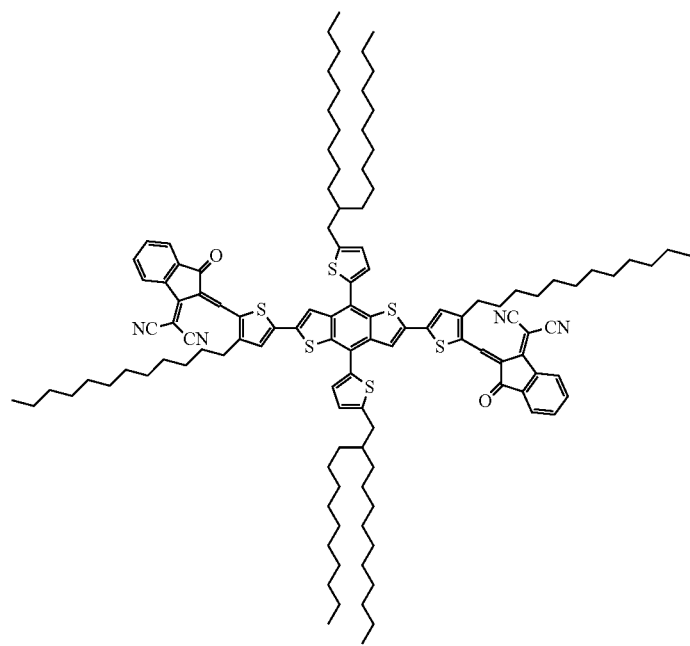

Exemplary Compound 2-8
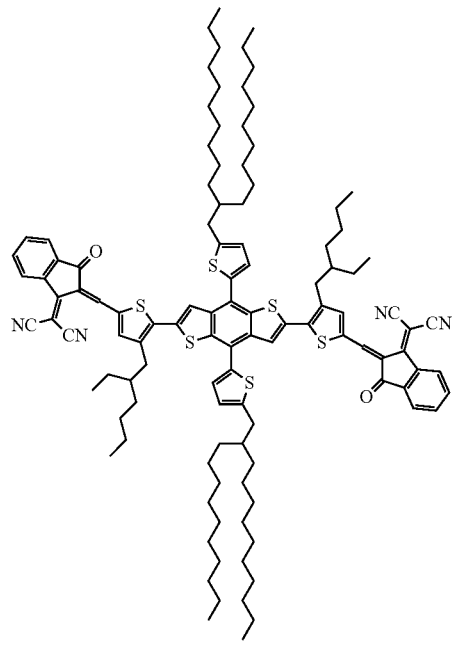
Exemplary Compound 2-9
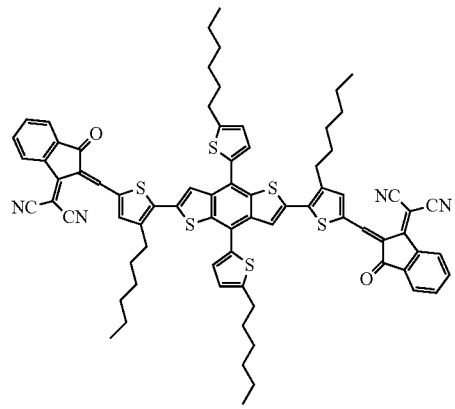
Exemplary Compound 2-10
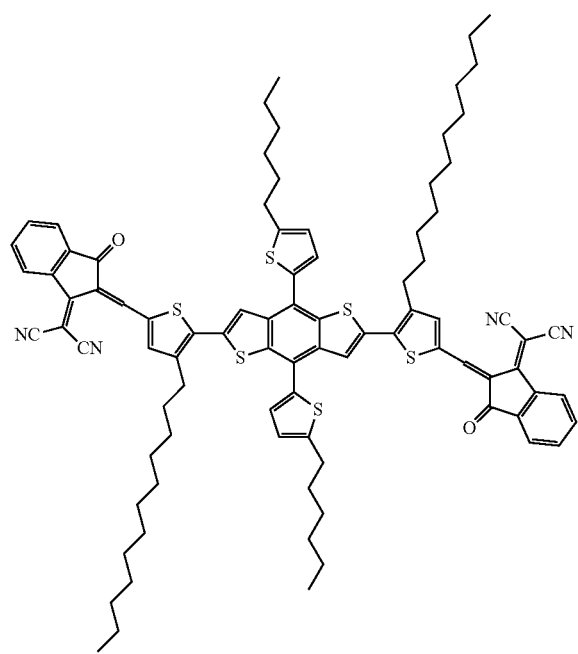

Exemplary Compound 2-11
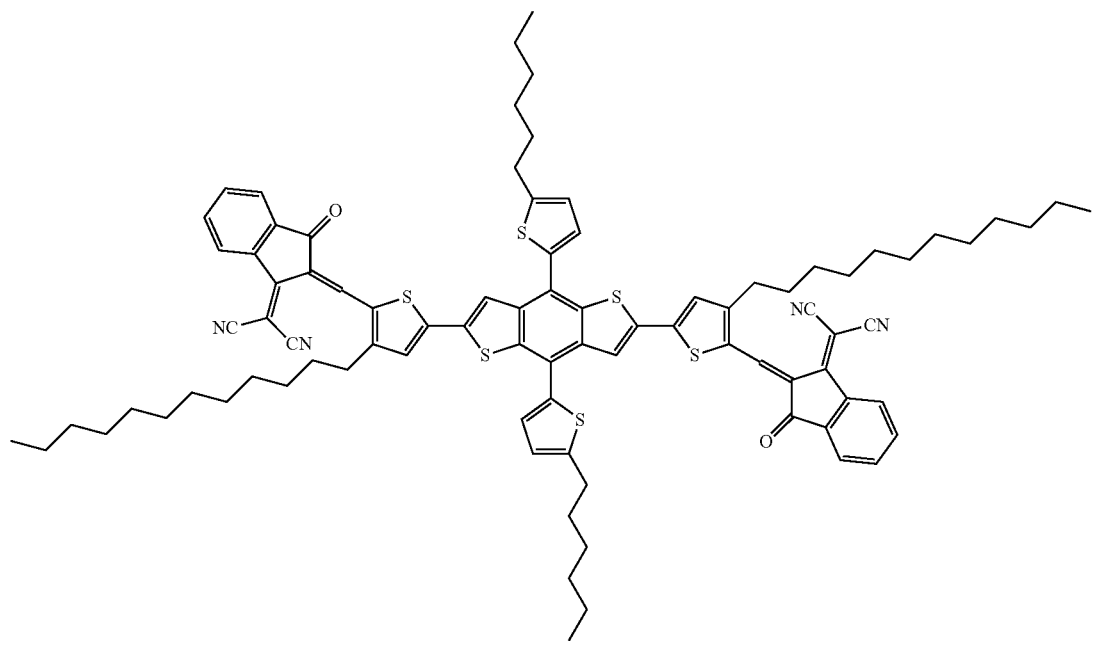
Exemplary Compound 2-12
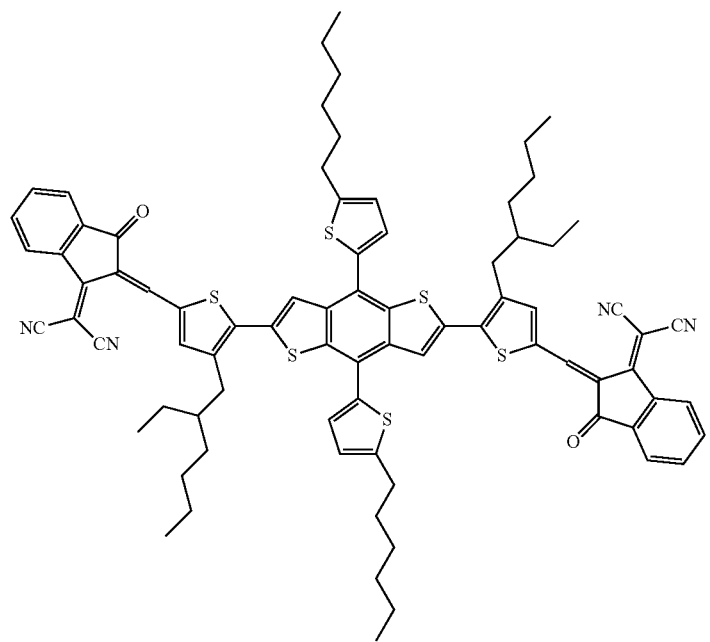

Exemplary Compound 2-13
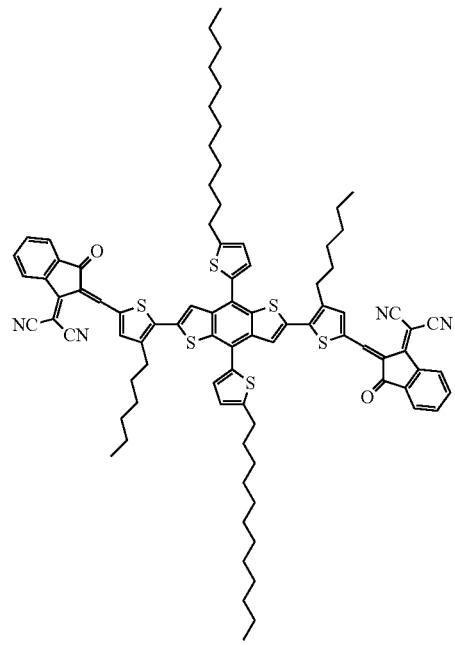
Exemplary Compound 2-14
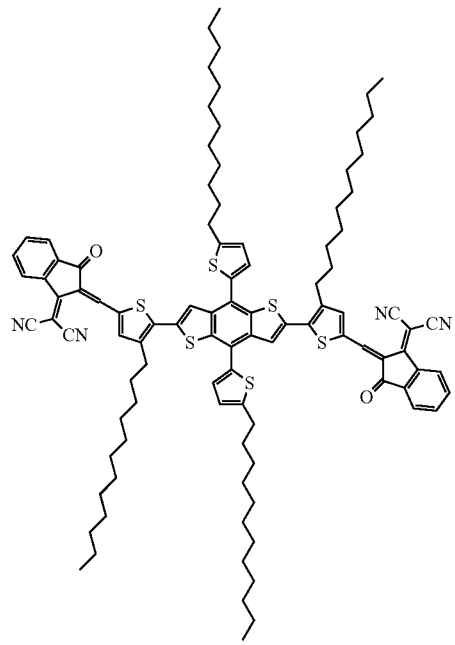
Exemplary Compound 2-15
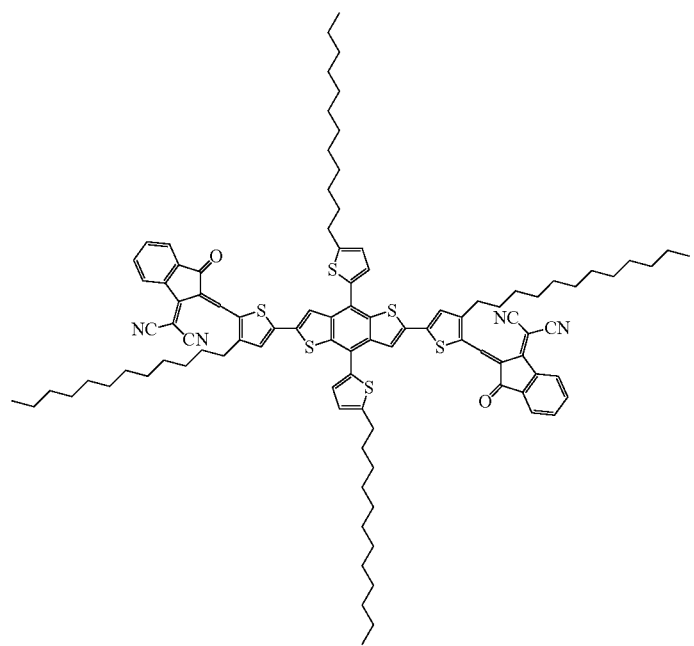

Exemplary Compound 2-16
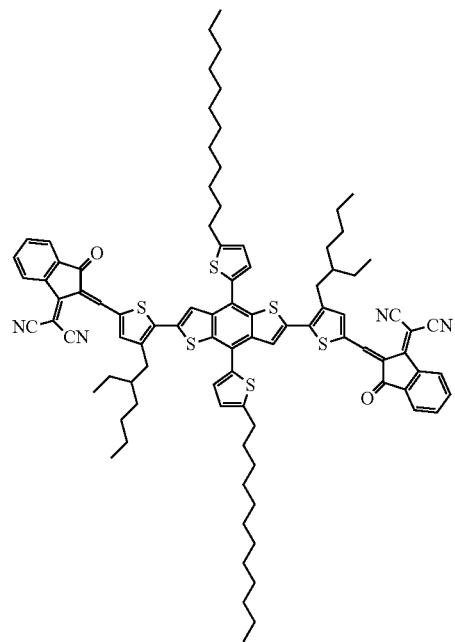
Exemplary Compound 2-17
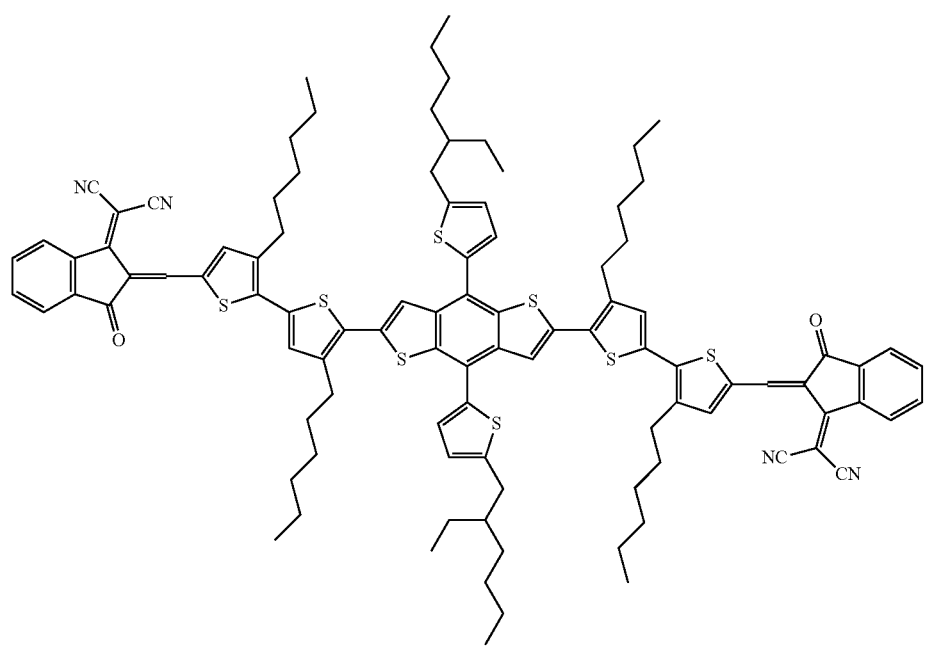

Exemplary Compound 2-18
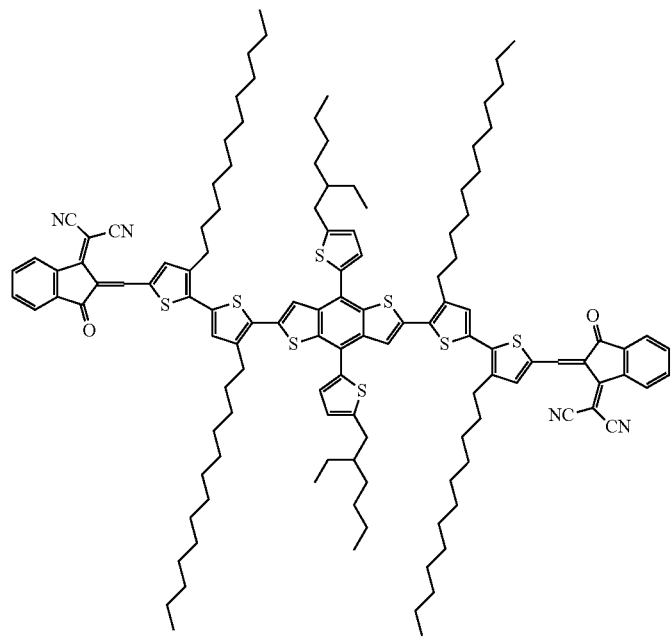
Exemplary Compound 2-19
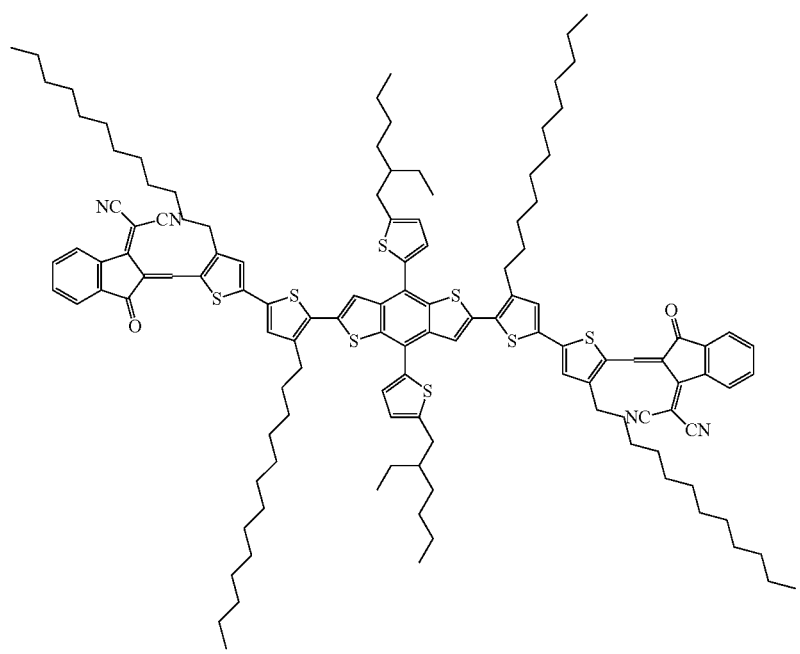

-continued
Exemplary Compound 2-20
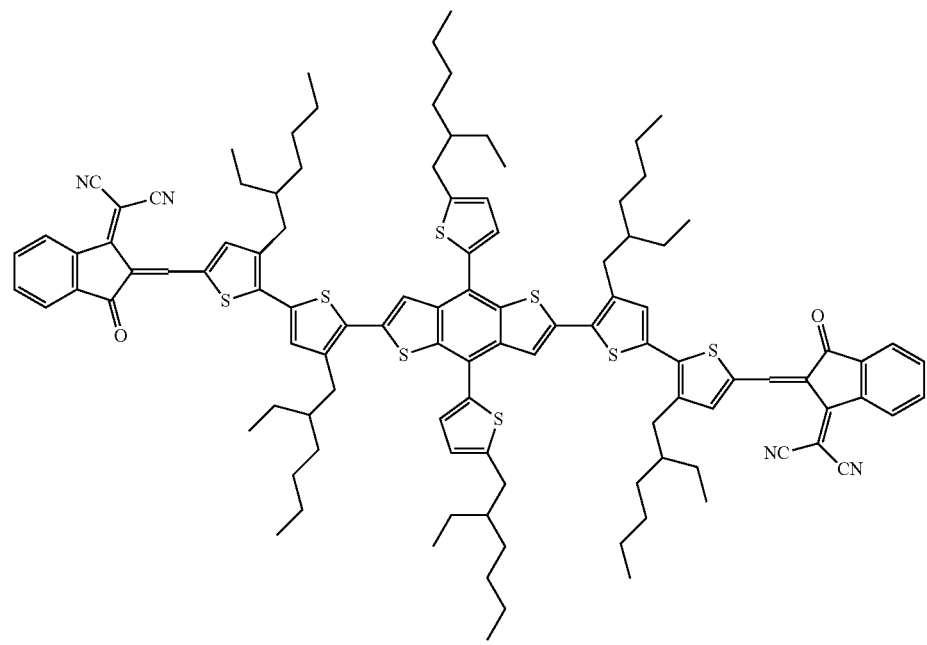
Exemplary Compound 2-21
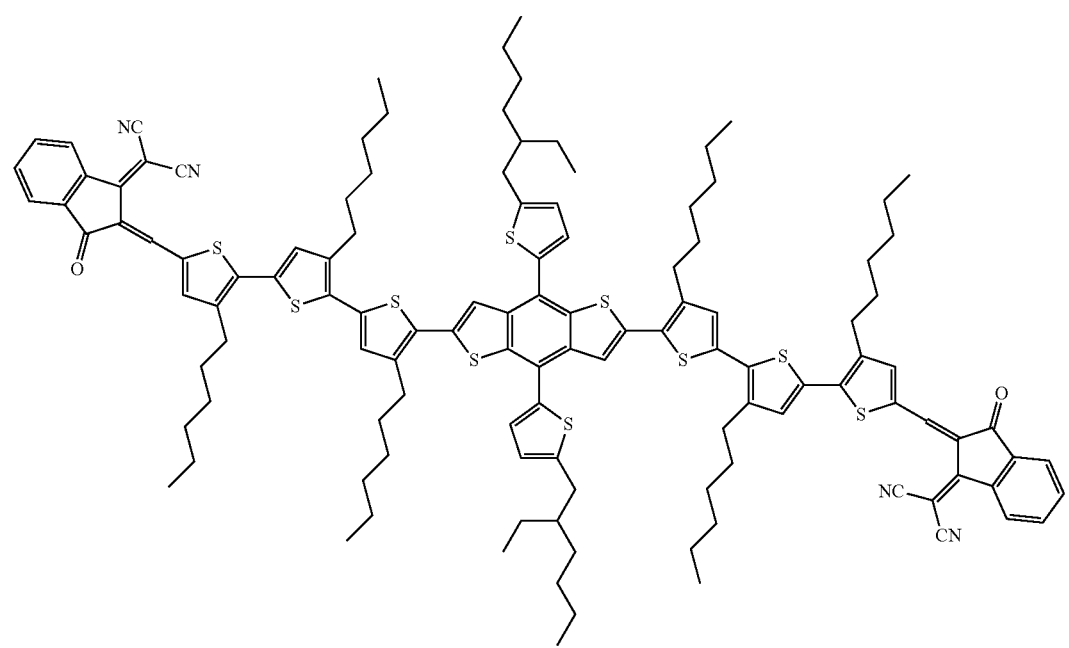

Exemplary Compound 2-22
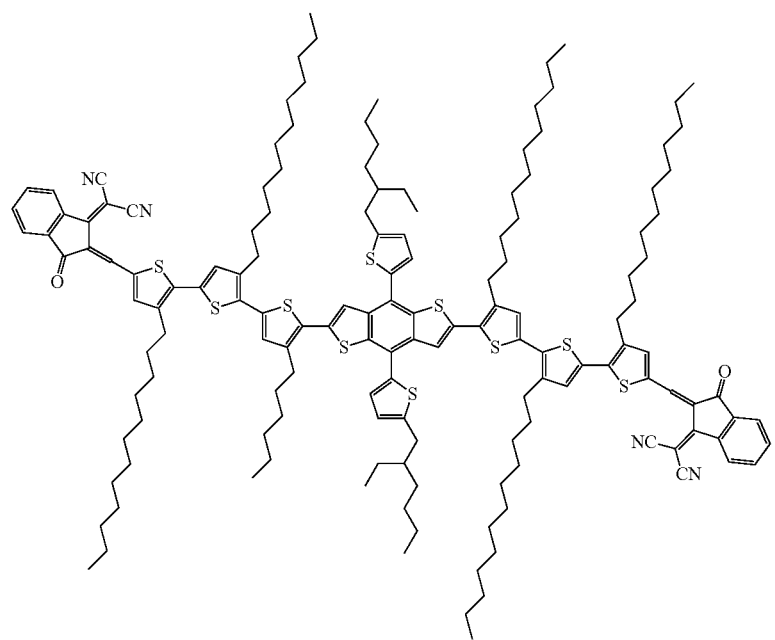
Exemplary Compound 2-23
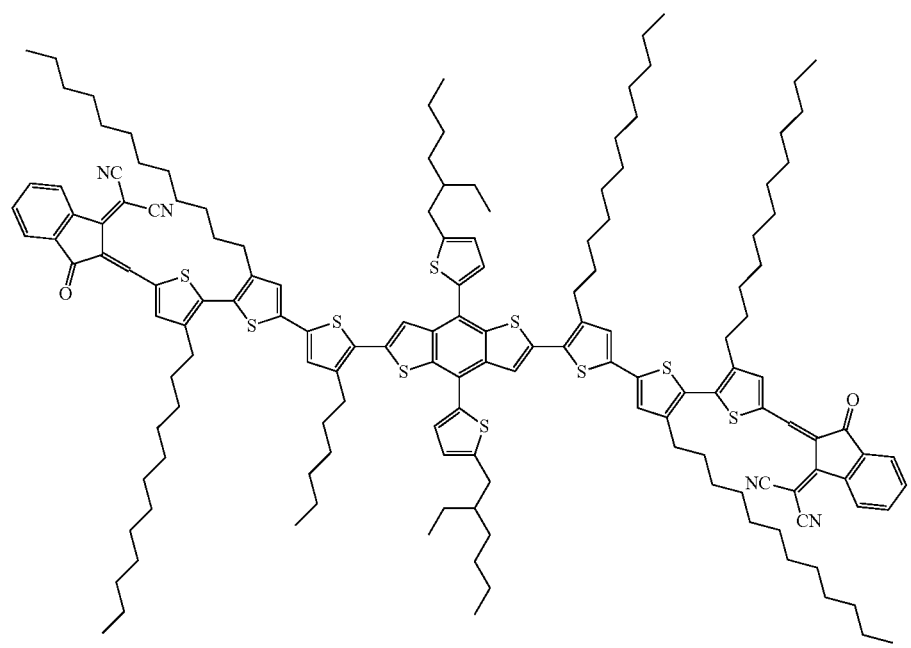

Exemplary Compound 2-24
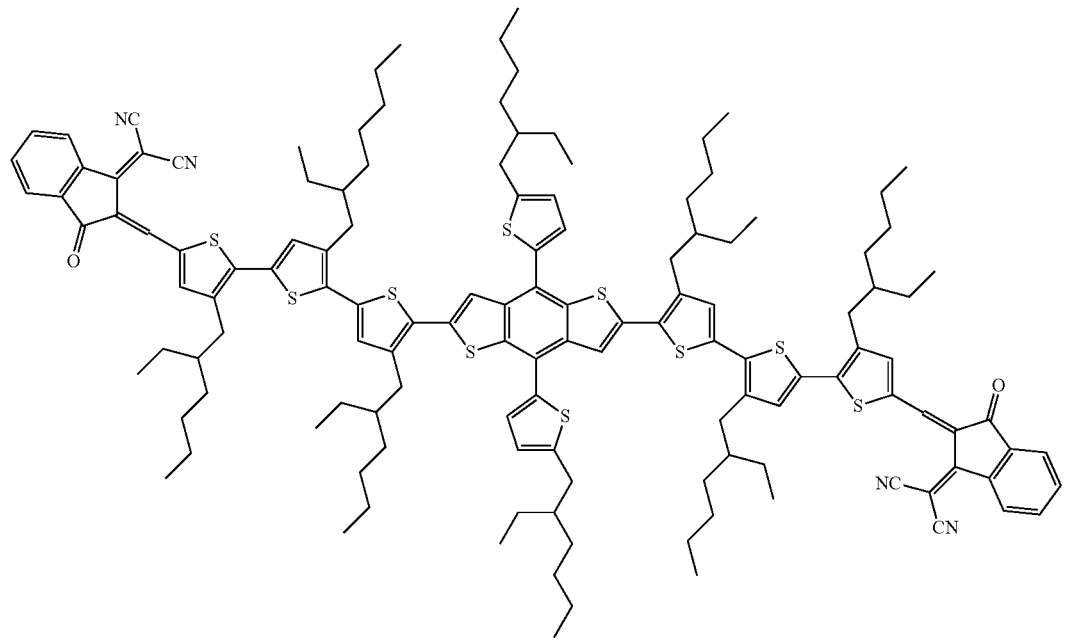
Among the exemplary compounds listed above, particularly preferred are Exemplary Compound 2-1, Exemplary Compound 2-2, Exemplary Compound 2-4, Exemplary Compound 2-10, Exemplary Compound 2-12, Exemplary Compound 2-17, and Exemplary Compound 2-21.
For example, the organic compound represented by the general formula (2) can be synthesized by the following steps.
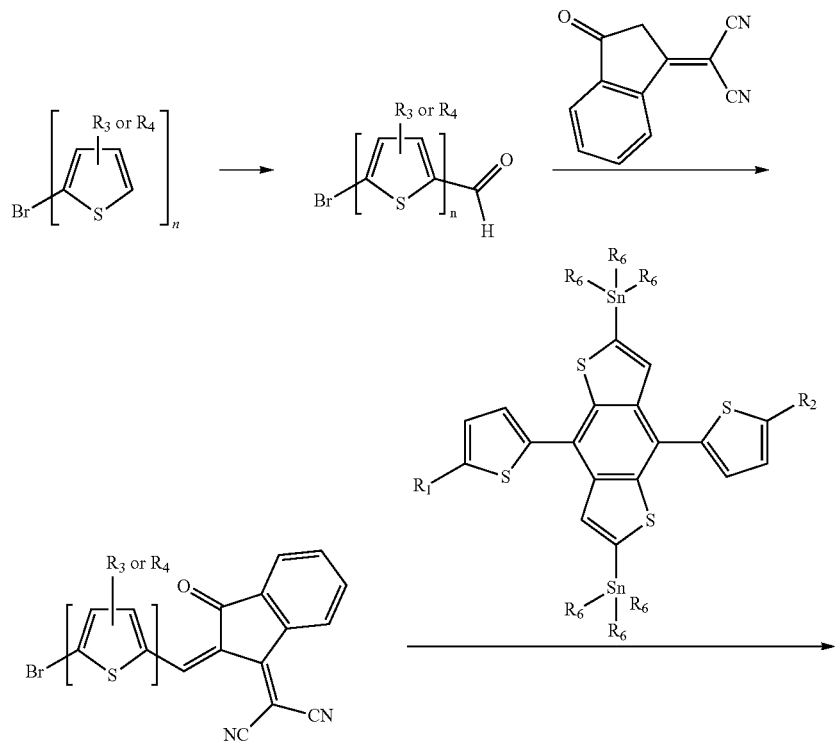

-continued

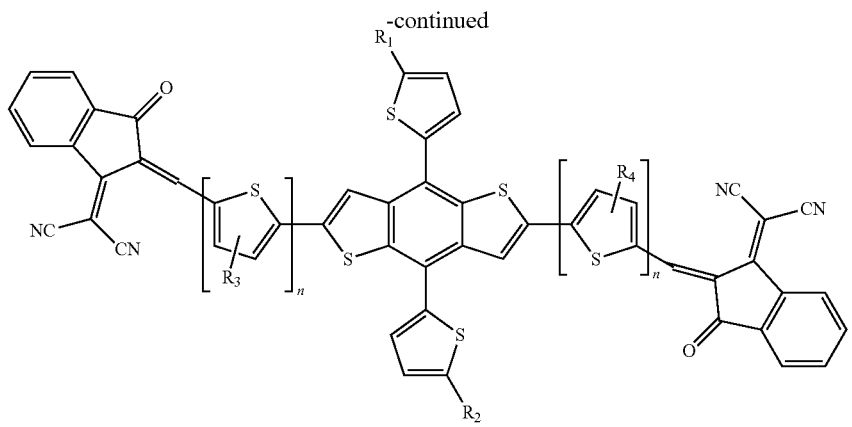

(First Step)

Bromothiophene, in which 3- or 4-position of thiophene is alkylated, is formylated at 5-position, to thereby obtain a thiophene derivative including a formyl group. As for a method of the formylation, a typical method is used. In particular, a method called Vilsmeier reaction, where formylation is performed with phosphorus oxychloride and dimethyl formamide or dimethyl formanilide, is preferable. Another example may be a method where a hydrogen abstraction reaction is carried out with an organic lithium compound having low nucleophilicity, such as lithium diisopropyl amide, followed by lithiation, and formylation is then performed with DMF.

(Second Step)

The obtained thiophene derivative including a formyl group and 3-(dicyanomethylidene)indan-1-one are subjected to dehydration condensation, to thereby obtain a brominated thiophene-indandione derivative. As for a method of the dehydration condensation, a typical method can be used. Examples thereof include: a method where the thiophene derivative including a formyl group and 3-(dicyanomethylidene)indan-1-one are heated in a solvent in the presence of an acid catalyst, such as acetic acid, and hydrochloric acid; and a method where the thiophene derivative including a formyl group and 3-(dicyanomethylidene)indan-1-one are heated in a solvent in the presence of an organic base catalyst, such as pyridine, and piperidine. In particular, a method where the thiophene derivative including a formyl group and 3-(dicyanomethylidene)indan-1-one are heated in acetic acid anhydride is preferable. As for the solvent, a typical solvent can be used. Examples of the solvent include toluene, chlorobenzene, THF, 1,4-dioxane, DMF, NMP, 1,2-dichloroethane, ethanol, and IPA.

(Third Step)

The obtained brominated thiophene-3-(dicyanomethylidene)indan-1-one derivative and an alkyltin-substituted benzodithiophene derivative are allowed to react through Stille coupling, to thereby obtain a compound represented by the general formula (2). As for the Stille coupling, a typical method disclosed in Org. React. 1997, 50, 1, can be used. $R_6$ is a C1-C4 alkyl group.

<Thin Organic-Material Film>

The organic compound of the present invention represented by the general formula (1) or the general formula (2) is a p-type organic semiconductor material (referred to as a p-type organic material, hereinafter).

Accordingly, the organic compound of the present invention is used in combination with a n-type organic semiconductor material (referred to as a n-type organic material, hereinafter) to form a thin film (thin organic-material film), and the thin film can be used as a member constituting a semiconductor element.

The thin organic-material film of the present invention includes at least the organic compound of the present invention, and a n-type organic material. The thin organic-material film may further include other ingredients, if necessary.

The thin organic-material film contains a p-type organic material and the n-type organic material, and uses the organic compound represented by the general formula (1) or the general formula (2) as the p-type organic material. Note that, the thin organic-material film may further contain other p-type organic materials.

Examples of the aforementioned other p-type organic materials include a polymer material (e.g., a polythiophene compound, a polyphenylene vinylene compound, a polyfluorene compound, and a polyphenylene compound), and a low molecular material (e.g., various porphyrins, and phthalocyanine).

Examples of the n-type organic material include fullerene, a fullerene derivative, a naphthalenetetracarboxylic acid dimide derivative, and a perylenetetracarboxylic acid diimide derivative. Among them, a fullerene derivative is preferable in view of charge separation, and charge transportation.

The fullerene derivative may be appropriately synthesized for use, or selected from commercial products. Examples of the commercial products include PC71BM (phenyl-C71-butylic acid methyl ester), PC61BM, and an indene-fullerene bis-adduct.

Note that, other than the n-type organic material above, an inorganic compound, such as zinc oxide, and titanium oxide, may be used.

In the present invention, a film of the p-type organic material and a film of the n-type organic material are sequentially formed to form a flat junction interface. In order to make an area of the junction interface large, however, a bulk heterojunction where the p-type organic material and the n-type organic material are mixed three-dimensionally is preferably formed.

In the case where the materials for use are highly soluble, in order to form the bulk heterojunction, the p-type organic material and the n-type organic material are dissolved in a solvent to form a solution, in which where the p-type organic material and the n-type organic material are mixed at molecular level, the solution is applied, and the applied solution is dried to remove the solvent to thereby form the bulk heterojunction. The aggregation state of each semiconductor may be optimized by further performing a heating process.

In the case where the materials for use are poorly dissolved, the n-type organic material is dispersed in a solvent, in which the organic compound of the present invention is dissolved, to prepare a solution, and the solution is applied to form a mixed layer. In this case, the aggregation state of each semiconductor can be optimized by further performing a heating process.

The organic compound for use in the present invention easily forms an aggregate structure, and is rigid. Accordingly, the organic compound has excellent heat resistance. The organic compound has a deep HOMO level, and excellent stability in the atmosphere, and moreover, an improvement in open-circuit voltage can be expected owing to the organic compound. As a soluble group, such as an alkyl group, is introduced into the aforementioned rigid molecular skeleton, in addition, an organic semiconductor film having a regular aggregation state, such as crystallinity, liquid crystallinity, and orientation, is effectively formed, with securing dissolvability to a typical organic solvent. In the highly regulated state, high charge transporting ability of the film can be expected. It is particularly important that an alkyl group of a thiophene group introduced into a benzodithiophene through substitution is a branched alkyl group in the general formula (1). As the alkyl chain is a branched chain, dissolvability is significantly improved. As the dissolvability is improved, the thin organic film can be formed into a thin film. As the thin organic film can be made thick, a large quantity of light can be absorbed, leading to an improvement of power generation.

Meanwhile, in the organic material disclosed in the literature "Chem. Mater. 2013, 25, 2274-2281," an alkyl group of a thiophene group introduced into a benzodithiophene through substitution is a straight chain alkyl group. In this case, as described in Examples, dissolvability of the material id low, and it is difficult to make a thickness of a thin organic film large. The organic compound having a branched alkyl group, represented by the general formula (1) has the higher dissolvability and is more advantageous in terms of formation of a thick film.

In the case where a thin organic-material film is formed by mixing the organic compound represented by the general formula (1) or (2) and a n-type organic material, the organic compound represented by the general formula (1) or (2) and the n-type organic material are added to a solvent at the predetermined mass ratio, and the organic compound represented by the general formula (1) or (2) and the n-type organic material are dissolved in the solvent by a method, such as heating, stirring, ultrasonic irradiation, to thereby prepare a solution, and the solution is applied onto an electrode. In this case, photoelectric conversion efficiency of a resulting photoelectric conversion element can be improved by using a mixed solvent prepared by blending two or more solvents.

The mass ratio of the organic compound represented by the general formula (1) or the general formula (2) to the n-type organic material is preferably in a range of from 2:1 through 1:2.

Examples of a formation method of the thin organic-material film include spin coating, blade coating, slit-die coating, screen printing, bar coating, mold coating, print transfer, dip coating, inkjet printing, spray coating, and vacuum vapor deposition. The formation method can be appropriately selected from the aforementioned examples depending on properties of a thin organic-material film to be produced, such as thickness controlling, and orientation controlling.

In the case where spin coating is performed, for example, a concentration of the compound represented by the general formula (1) or general formula (2), and the n-type organic material (a total mass of the organic compound represented by the general formula (1) or the general formula (2), and the n-type organic material relative to a volume of a solution containing the organic compound represented by the general formula (1) or the general formula (2) and the n-type organic material) is preferably in a range of from 5 mg/mL through 30 mg/mL. As the concentration of the solution is adjusted to the aforementioned range, a uniform thin organic-material film can be easily produced.

In order to remove the organic solvent from the produced thin organic-material film, an annealing treatment may be performed under the reduced pressure or inert atmosphere (nitrogen or argon atmosphere). The temperature of the annealing treatment is preferably in a range from 40° C. through 300° C., more preferably in a range of from 50° C. through 200° C. As the annealing treatment is performed, stacked layers are penetrated into each other at interfaces, to thereby increase contacting effective areas. As a result, a short-circuit current can be increased. Note that, the annealing treatment may be performed after forming electrodes.

The average thickness of the thin organic-material film is preferably in a range of from 50 nm through 500 nm, more preferably in a range of from 100 nm through 300 nm. When the average thickness is less than 100 nm, a quantity of light absorbed by the thin organic-material film is insufficient, and thus a quantity of carriers generated is insufficient. When the average thickness is greater than 500 nm, transport efficiency of carriers generated by light absorption is degraded even more.

The thin organic-material film of the present invention can be used for various uses, but the thin organic-material film is suitably used as a photoelectric conversion layer of the photoelectric conversion element of the present invention described below.

(Photoelectric Conversion Layer)

The photoelectric conversion layer of the present invention includes at least the organic compound of the present invention, which has a structure represented by the general formula (1) or the general formula (2), and a n-type organic material. The aforementioned thin organic-material film can be used as a material of the photoelectric conversion layer.

(Solution for Forming Photoelectric Conversion Layer)

The photoelectric conversion layer of the present invention can be formed by using a solution for forming a photoelectric conversion layer. The solution contains at least the organic compound of the present invention, which has a structure represented by the general formula (1) or the general formula (2), a n-type organic material, and an organic solvent. The solution may further contain other ingredients, if necessary.

An amount of the organic compound is preferably in a range of from 0.5% by mass through 10% by mass relative to a total amount of the solution for forming a photoelectric conversion layer.

As for the n-type organic material, any of the materials listed as examples of the n-type organic material listed in the description of the thin organic-material film can be used.

An amount of the n-type organic material is preferably in a range of from 0.5% by mass through 10% by mass, relative to a total amount of the solution for forming a photoelectric conversion layer.

The organic solvent is appropriately selected depending on the intended purpose without any limitation. Examples of the organic solvent include methanol, ethanol, butanol, toluene, xylene, o-chlorophenol, acetone, ethyl acetate, ethylene glycol, tetrahydrofuran, dichloromethane, chloroform, dichloroethane, chlorobenzene, dichlorobenzene, trichlorobenzene, dimethylformamide, dimethyl sulfoxide, N-methylpyrrolidone, and γ-butyrolactone. These organic solvents may be used alone, or in combination. Among them, preferred are chlorobenzene, chloroform, and o-dichlorobenzene.

The aforementioned other ingredients are appropriately selected depending on the intended purpose without any limitation. Examples of the ingredients include various additives, such as diiodooctane, octaonediol, and 1-chloronaphthalene. Among them, 1-chloronaphthalene is preferable. As the 1-chloronaphthalene is added, a positive/negative phase separation structure of the resulting photoelectric conversion layer becomes close to an optimal structure. Accordingly, photoelectric conversion ability is improved.

(Photoelectric Conversion Element)

The photoelectric conversion element of the present invention is a photoelectric conversion element, which includes a substrate, a first electrode, an electron-transporting layer, a photoelectric conversion layer, a hole-transporting layer, and a second electrode, where the first electrode, the electron-transporting layer, the photoelectric conversion layer, the hole-transporting layer, and the second electrode are disposed on the substrate in this order. Alternatively, the photoelectric conversion element of the present invention is a photoelectric conversion element, which includes a substrate, a first electrode, a hole-transporting layer, a photoelectric conversion layer, an electron-transporting layer, and a second electrode, where the first electrode, the hole-transporting layer, the photoelectric conversion layer, the electron-transporting layer, and the second electrode are disposed in this order on the substrate. The photoelectric conversion layer includes the thin organic-material film of the present invention, or the organic compound of the present invention.

The photoelectric conversion element of the present invention is described with reference to drawings hereinafter.

Figure 2:
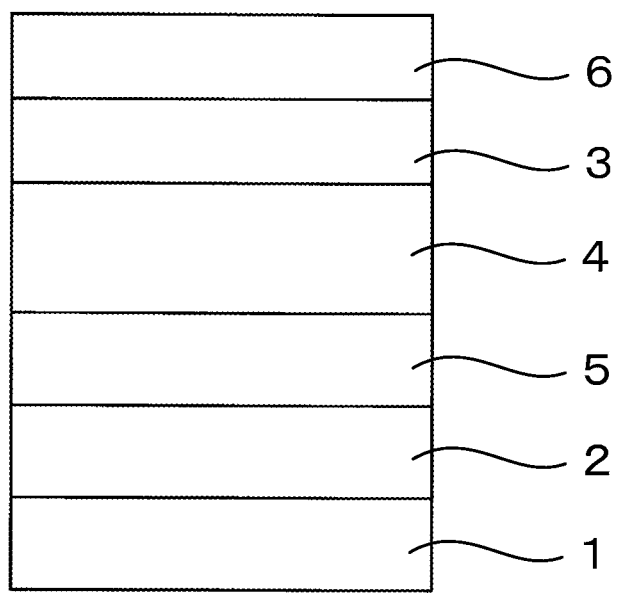
FIG. 2 is a schematic view illustrating another example of the photoelectric conversion element of the present invention.

FIG. 1 illustrates a structure where a first electrode 2, an electron-transporting layer 3, a photoelectric conversion layer 4, a hole-transporting layer 5, and a second electrode 6 are sequentially disposed on a substrate 1. FIG. 2 illustrates a structure where a first electrode 2, a hole-transporting layer 5, a photoelectric conversion layer 4, an electron-transporting layer 3, and a second electrode 6 are sequentially disposed on a substrate 1.

<Substrate>

The substrate for use in the present invention is not particularly limited, and is selected from substrates known in the art. The substrate 1 is preferably a transparent material, and examples thereof include glass, a transparent plastic plate, a transparent plastic film, and a transparent inorganic crystal.

<First Electrode and Second Electrode>

As for at least either of electrodes, an electrode transparent to visible light is used. The other electrode may be transparent or opaque.

The electrode transparent to visible light is not particularly limited, and a typical electrode used for a photoelectric conversion element or liquid crystal panel can be used. Examples of such the electrode include conductive metal oxides, such as tin-doped indium oxide (referred to as "ITO" hereinafter), fluorine-doped tin oxide (referred to as "FTO" hereinafter), antimony-doped tin oxide (referred to as "ATO" hereinafter), and aluminium- or gallium-doped zinc oxide (referred respectively as "AZO," and "GZO" hereinafter). The average thickness of the electrode transparent to visible light is preferably in a range of from 5 nm through 10 µm, more preferably in a range of from 50 nm through 1 µm.

In order to maintain certain hardness, the electrode transparent to visible light is preferably disposed on a substrate composed of a material transparent to visible light. A product of the electrode and the substrate that are integrated can also be used. Examples thereof include FTO coated glass, ITO coated glass, zinc oxide:aluminium coated glass, an FTO coated transparent plastic film, and an ITO coated transparent plastic film.

The electrode transparent to visible light may be an electrode containing a substrate (e.g., a glass substrate) on which a metal electrode having the structure through which light can pass (e.g., a mesh-patterned structure or a stripe-pattered structure) is disposed. Alternatively, the electrode transparent to visible light may be an electrode where carbon nanotube or graphene is laminated on the substrate in a manner that transparency is secured. These may be used alone, or in combination, or in the state of a laminate.

In order to reduce substrate resistance, moreover, a metal lead wire may be used. Examples of a material of the metal lead wire include metals, such as aluminium, copper, silver, gold, platinum, and nickel. The metal lead wire is disposed on the substrate, for example, by vapor deposition, sputtering, or crimping, followed by disposing ITO or FTO thereon.

In the case where an opaque electrode is used as at least either of the first electrode or the second electrode, examples of a material of the opaque electrode include metals (e.g., platinum, gold, silver, copper, and Al), and graphite. A thickness of the opaque electrode is not particularly limited, and the opaque electrode may be made of one kind material alone, or may be a laminate made of two or more kinds materials.

<Electron-Transporting Layer>

A material for forming the electron-transporting layer is appropriately selected depending on the intended purpose. For example, the electron-transporting layer is formed by applying an electron-accepting organic material [e.g., perylenetetracarboxylic anhydride, perylenetetracarboxylic diimide, oxazole derivatives, triazol derivatives, phenanthroline derivatives, phosphine oxide derivatives, fullerene compounds, carbon nanotube (CNT), and CN-PPV], or an inorganic material (e.g., zinc oxide, titanium oxide, lithium fluoride, and calcium metal) through a sol-gel method or sputtering. In case of the photoelectric conversion element having the progressive structure illustrated in FIG. 2, the material of the electron-transporting layer is preferably lithium fluoride. In case of the photoelectric conversion element having the inverse structure illustrated in FIG. 1, the material of the electron-transporting layer is preferably zinc oxide.

The average thickness of the electron-transporting layer is appropriately selected depending on the intended purpose without any limitation. The electron-transporting layer preferably coats the entire surface as thin as possible. The average thickness thereof is more preferably in a range of from 10 nm through 60 nm.

<Hole-Transporting Layer>

The hole-transporting layer is disposed to improve a collection efficiency of holes. Specifically, the hole-transporting layer is formed by applying a conductive polymer [e.g., PEDOT:PSS (polyethylene dioxythiophene:polystyrene sulfonate), a hole-transporting organic compound (e.g., an aromatic amine derivative), or a hole-transporting inorganic compound (e.g., molybdenum oxide, vanadium oxide, and nickel oxide) through spin coating, a sol-gel method, or sputtering. In the present invention, it is preferred that molybdenum oxide be disposed.

The average thickness of the hole-transporting layer is appropriately selected depending on the intended purpose without any limitation. The hole-transporting layer preferably coats the entire surface as thin as possible. The average thickness thereof is more preferably in a range of from 1 nm through 50 nm.

<Photoelectric Conversion Layer>

The photoelectric conversion layer includes the thin organic-material film of the present invention, or the organic compound of the present invention.

The average thickness of the photoelectric conversion layer is preferably in a range of from 50 nm through 500 nm, more preferably in a range of from 100 nm through 300 nm, and even more preferably in a range of from 60 nm through 250 nm. When the average thickness is less than 50 nm, a quantity of light absorbed by the thin organic-material film is insufficient, and thus a quantity of carriers generated is insufficient. When the average thickness is greater than 500 nm, transport efficiency of carriers generated by light absorption is degraded even more.

<Other Members>

The aforementioned other members are appropriately selected depending on the intended purpose without any limitation. Examples of the members include a gas barrier layer, a protective layer, and a buffer layer.

Examples of a material of the gas barrier layer include an inorganic material, such as silicon nitride, and silicon oxide.

The photoelectric conversion element of the present invention may have a series junction formed by stacking two or more photoelectric conversion layers (making as a tandem) via one or more intermediate electrodes.

Examples thereof include a laminate structure including a substrate/a first electrode/a hole-transporting layer/a first photoelectric conversion layer/an intermediate electrode/a second photoelectric conversion layer/an electron-transporting layer/a second electrode. Use of the aforementioned laminate can improve open-circuit voltage.

In case of the aforementioned laminate structure, it is preferred that at least one of the photoelectric conversion layers include a thin organic-material film containing the organic compound represented by the general formula (1) or the general formula (2), and the other layer contain another organic material having an absorption wavelength is different from that of the organic compound represented by the general formula (1) or the general formula (2), in order not to reduce short-circuit current.

Examples of the aforementioned other organic materials include a polymer material (e.g., a polythiophene compound, a polyphenylene vinylene compound, a polyfluorene compound, and a polyphenylene compound), and a low molecular material (e.g., various porphyrins, and phthalocyanine).

<Use>

Recently, demanded, especially as an energy harvesting element, is a photoelectric conversion element capable of efficiently generating electric power with weak light. Typical examples of weak light include LED light, and light of a fluorescent lamp. These are typically used indoor, and are called indoor lighting. The illuminance of these types of light is from about 20 lux through about 1,000 lux, and these are very weak light compared to direct sunlight (about 100,000 lux).

The photoelectric conversion element of the present invention exhibits high conversion efficiency with weak light, such as the aforementioned indoor lighting, and can be applied for a power supply by using in combination with a circuit board capable of controlling the generated electric current. Examples of a device utilizing the aforementioned power supply include calculators, and watches. Other than these examples, a power supply containing the photoelectric conversion element of the present invention can be used in mobile phones, electric organizers, and electronic paper. Moreover, a power supply containing the photoelectric conversion element of the present invention can also be used as an auxiliary power for extending continuous usage of rechargeable or battery-driven electric appliances. Furthermore, the present invention can be also applied as an image sensor.

EXAMPLES

Example I-1

Synthesis Example 1

Exemplary Compound 1-1 was synthesized according to the following scheme.

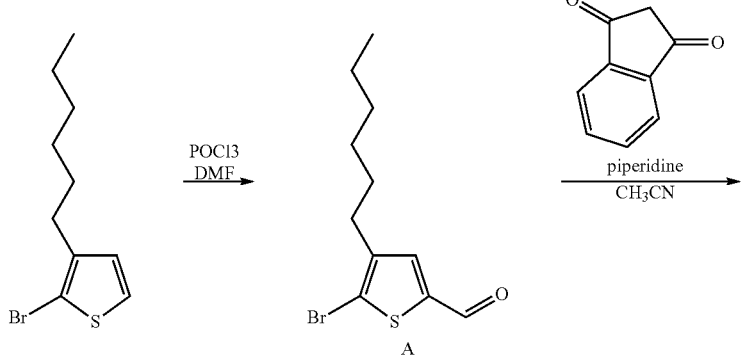

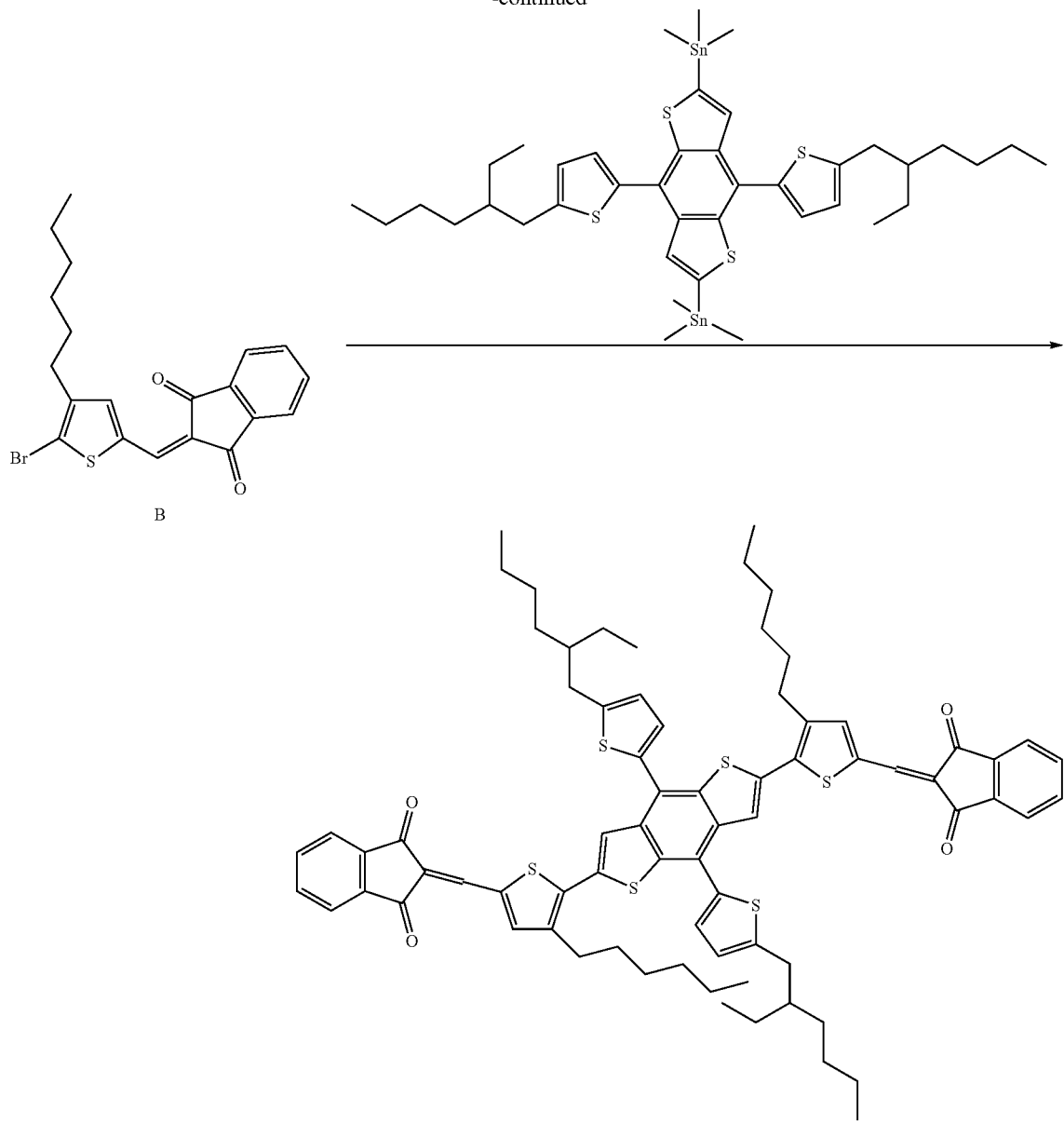

(Synthesis of A
(2-bromo-3-hexyl-5-thiophenecarboxyaldehyde))

A four-necked flask was charged with 30 mL of DMF, followed by cooling to 0° C. in an ice bath. To the flask, POCl$_3$ was gradually dripped. After the dripping, the mixture was warmed up to room temperature, followed by adding 2-bromo-3-hexylthiophene (manufactured by Tokyo Chemical Industry Co., Ltd.) (5.0 g, 20.2 mmol). The resulting mixture was stirred for 3 hours at 80° C. Thereafter, the obtained reaction liquid was neutralized with sodium hydrogen carbonate, from which an organic layer was extracted with ethyl acetate. The organic layer was dried with MgSO$_4$, followed by filtration and vacuum concentration. The concentrated product was purified by silica gel column (cyclohexane, followed by toluene), to thereby obtain A (2-bromo-3-hexyl-5-thiophenecarboxyaldehyde) (3.2 g, 10.9 mmol).

Synthesis of B

A recovery flask was charged with A (2.0 g, 7.29 mmol), 1,3-indanedione (manufactured by Tokyo Chemical Industry Co., Ltd.) (1.17 g, 8.02 mmol), and acetonitrile (20 mL), and the resulting mixture was stirred. To the resultant, 1 mL of piperidine was added. The resulting reaction solution was subjected to reflux for 3 hours. The generated sediment was collected through filtration, followed by washing 3 times with methanol, to thereby obtain B, yellow powder, (2.1 g, 5.22 mmol).

Synthesis of Exemplary Compound 1-1

A four-necked flask was charged with B (0.47 g, 1.16 mmol), 2,6-bis(trimethyltin)-4,8-bis(5-(2-ethylhexyl)thiophen-2-yl)benzo[1,2-b:4,5-b']dithiophene (manufactured by Luminescence Technology Corp.) (0.5 g, 0.55 mmol), Pd(PPh$_3$)$_4$ (80 mg), and 20 mL of toluene, followed by purging with argon. The resulting mixture was subjected to reflux for 5 hours. After removing the solvent from the reaction product through distillation, the reaction product was purified through silica gel chromatography (toluene), to thereby obtain Exemplary Compound 1-1 (0.4 g, 0.32 mmol). The identification was performed through mass spectrometry to thereby confirm that Exemplary Compound 1-1 (M/Z=1223.4 (M+H), relative to exact mass=1222.4) was obtained.

Moreover, as a result of an elemental analysis, the results were C:72.51, H:6.56, relative to the theoretical values C, 72.63; H, 6.42; O, 5.23; S, 15.72.

(Formation of Electron-Transporting Layer)

At room temperature, 1 g of zinc acetate (of SIGMA-ALDRICH), 0.28 g of ethanol amine (of SIGMA-ALDRICH), and 10 mL of methoxyethanol (manufactured by Wako Pure Chemical Industries, Ltd.) were stirred all night, to thereby prepare a zinc oxide precursor solution. The zinc oxide precursor solution was applied onto a glass substrate with ITO by spin coating to give a film thickness of 20 nm, followed by drying is for 10 minutes at 200° C., to thereby form an electron-transporting layer.

(Formation of Photoelectric Conversion Layer)

In 1 mL of chloroform, 7.5 mg of Exemplary Compound 1-1 and 7.5 mg of PC71BM (manufactured by Frontier Carbon Corporation) were dissolved, to thereby produce a solution for forming a photoelectric conversion layer. Onto the electron-transporting layer, the solution for forming a photoelectric conversion layer was applied by spin coating to give a film thickness of 100 nm, to thereby form a photoelectric conversion layer.

(Formation of Hole-Transporting Layer and Metal Electrode)

On the photoelectric conversion layer, 20 nm of molybdenum oxide (manufactured by Kojundo Chemical Laboratory Co., Ltd.), and 100 nm of silver were sequentially deposited by vacuum vapor deposition, to thereby produce a photoelectric conversion element.

The conversion efficiency of the obtained photoelectric conversion element under white LED irradiation [0.0125 mW/cm$^2$ (50 lux), 0.05 mW/cm$^2$ (200 lux), 0.25 mW/cm$^2$ (1,000 lux)] was measured.

The measurement was performed by using a desk lamp CDS-90α (study mode) manufactured by Cosmotechno Co., Ltd. as the white LED, and a solar battery evaluation system As-510-PV03 manufactured by NF Corporation as the evaluation device. The results are presented in Table 1-1.

Example I-2

A photoelectric conversion element was produced in the same manner as in Example I-1, provided that, in the course of producing the solution for forming a photoelectric conversion layer, 1-chloronaphthalene was added to chloroform by 1% by volume. The produced photoelectric conversion element was evaluated in the same manner as in Example I-1. The results are presented in Table 1-1.

Example I-3

A photoelectric conversion element was produced in the same manner as in Example I-2, provided that, in the course of producing the photoelectric conversion layer, Exemplary Compound 1-1 was replaced with Exemplary Compound 1-2. The produced photoelectric conversion element was evaluated in the same manner as in Example I-2. The results are presented in Table 1-1.

Example I-4

A photoelectric conversion element was produced in the same manner as in Example I-2, provided that, in the course of producing the photoelectric conversion layer, Exemplary Compound 1-1 was replaced with Exemplary Compound 1-3. The produced photoelectric conversion element was evaluated in the same manner as in Example I-2. The results are presented in Table 1-1.

Example I-5

A photoelectric conversion element was produced in the same manner as in Example I-2, provided that, in the course of producing the photoelectric conversion layer, Exemplary Compound 1-1 was replaced with Exemplary Compound 1-4. The produced photoelectric conversion element was evaluated in the same manner as in Example I-2. The results are presented in Table I-1.

Example I-6

(Formation of Hole-Transporting Layer)

Onto a glass substrate with ITO, a PEDOT:PSS (polyethylene dioxythiophene:polystyrene sulfonate, CleviosP VP AI4083 manufactured by H. C. Stark GmbH) solution was applied by spin coating to give a film thickness of 20 nm. The applied solution was dried for 10 minutes at 130° C., to thereby form a hole-transporting layer.

(Formation of Photoelectric Conversion Layer)

In 1 mL of chloroform, 7.5 mg of Exemplary Compound 1-1, and 7.5 mg of PC71BM (manufactured by Frontier Carbon Corporation) were dissolved, to thereby prepare a solution for forming a photoelectric conversion layer. Onto the hole-transporting layer, the solution for forming a photoelectric conversion layer was applied by spin coating to give a film thickness of 100 nm, to thereby form a photoelectric conversion layer.

(Formation of Electron-Transporting Layer and Second Electrode)

Subsequently, a film of lithium fluoride in the thickness of 1 nm, and a Al electrode in the thickness of 80 nm were formed on the photoelectric conversion layer by vacuum vapor deposition at 1×10$^{-6}$ Torr, to thereby produce a photoelectric conversion element.

The obtained photoelectric conversion element was evaluated in the same manner as in Example I-1. The results are presented in Table 1-1.

Example I-7

A photoelectric conversion element was produced in the same manner as in Example I-2, provided that, in the course of producing the solution for forming a photoelectric conversion layer, the amount of Exemplary Compound 1-1 was changed to 15 mg, and the amount of PC71BM was changed to 15 mg. The produced photoelectric conversion element was evaluated in the same manner as in Example I-2. The results are presented in Table 1-1.

Example I-8

A photoelectric conversion element was produced in the same manner as in Example I-2, provided that, in the course of producing the solution for forming a photoelectric conversion layer, the amount of Exemplary Compound 1-1 was changed to 9 mg, and the amount of PC71BM was changed to 6 mg. The produced photoelectric conversion element was evaluated in the same manner as in Example I-2. The results are presented in Table 1-1.

Example I-9

A photoelectric conversion element was produced in the same manner as in Example I-2, provided that, in the course of producing the solution for forming a photoelectric conversion layer, the amount of Exemplary Compound 1-1 was changed to 6.7 mg, and the amount of PC71BM was changed to 8.3 mg. The produced photoelectric conversion element was evaluated in the same manner as in Example I-2. The results are presented in Table 1-1.

Comparative Example I-1

A photoelectric conversion element was produced in the same manner as in Example I-1, provided that, in the course of producing the solution for forming a photoelectric conversion layer, Exemplary Compound 1-1 was replaced with Comparative Compound 1-1 presented below, and described in the literature "Chem. Mater. 2013, 25, 2274-2281." The produced photoelectric conversion element was evaluated in the same manner as in Example I-1. Comparative Compound 1-1 was synthesized by the method described in the literature "Chem. Mater. 2013, 25, 2274-2281." The results are presented in Table 1-1.

Comparative Example I-2

A photoelectric conversion element was produced in the same manner as in Comparative Example I-1, in the course of producing the solution for forming a photoelectric conversion layer, the amount of Comparative Compound 1-1 was changed to 9 mg, and the amount of PC71BM was changed to 6 mg. The produced photoelectric conversion element was evaluated in the same manner as in Example I-1. The results are presented in Table 1-1.

Comparative Example I-3

A solution for forming a photoelectric conversion layer was produced in the same manner as in Comparative Example I-1, provided that the amount of Comparative Compound 1-1 was changed to 15 mg, and the amount of PC71BM was changed to 15 mg. However, the insoluble component was precipitated. Accordingly, an element could not be produced.

Comparative Example I-4

A photoelectric conversion element was produced in the same manner as in Example I-6, provided that, in the course of producing the solution for forming a photoelectric conversion layer, Exemplary Compound 1-1 was replaced with Comparative Compound 1-1. The produced photoelectric conversion element was evaluated in the same manner as in Example I-6. The results are presented in Table 1-1.

Comparative Example I-5

A photoelectric conversion element was produced in the same manner as in Example I-2, provided that, in the course of producing the solution for forming a photoelectric conversion layer, Exemplary Compound 1-1 was replaced with 6 mg of PTB7 having the structure presented below (manu-

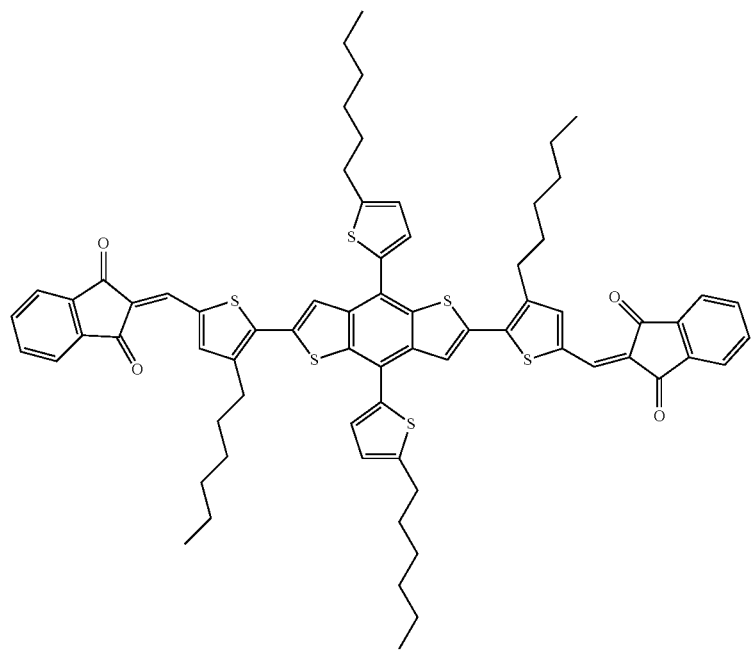

Comparative Compound 1-1 factured by 1-Material), the amount of PC71BM was changed to 9 mg, and 1-chloronaphthalene was replaced with 1,8-diiodooctane. The produced photoelectric conversion element was evaluated in the same manner as in Example I-2. The results are presented in Table 1-1.

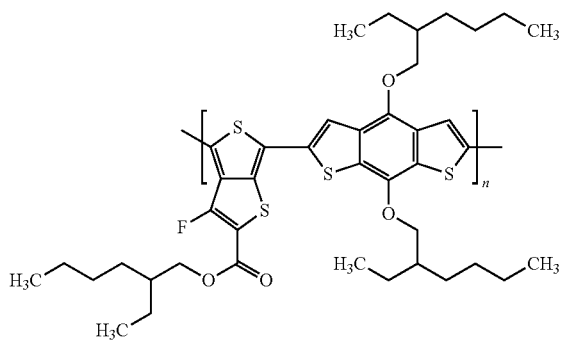

TABLE 1-1

| | Conversion efficiency (%) with LED (50 lux, 0.0125 mW/cm$^2$) | Conversion efficiency (%) with LED (200 lux, 0.05 mW/cm$^2$) | Conversion efficiency (%) with LED (1,000 lux, 0.25 mW/cm$^2$) |
|---|---|---|---|
| Ex. I-1 | 17.2 | 18.1 | 19.4 |
| Ex. I-2 | 18.7 | 19.1 | 19.8 |
| Ex. I-3 | 17.0 | 17.4 | 17.9 |
| Ex. I-4 | 17.9 | 18.3 | 18.8 |
| Ex. I-5 | 16.1 | 16.8 | 17.5 |
| Ex. I-6 | 19.4 | 19.6 | 20.1 |
| Ex. I-7 | 20.0 | 20.3 | 21.0 |
| Ex. I-8 | 18.9 | 19.8 | 20.2 |
| Ex. I-9 | 18.8 | 19.4 | 19.9 |
| Comp. Ex. I-1 | 9.4 | 10.2 | 10.7 |
| Comp. Ex. I-2 | 10.8 | 11.3 | 11.9 |
| Comp. Ex. I-3 | Could not be evaluated | Could not be evaluated | Could not be evaluated |
| Comp. Ex. I-4 | 11.8 | 12.3 | 12.8 |
| Comp. Ex. I-5 | 11.6 | 11.9 | 12.2 |

It was demonstrated that the photoelectric conversion elements produced according to the present invention had the high conversion efficiency with weak light described above, and were excellent compared to the photoelectric conversion elements produced in Comparative Examples.

Subsequently, the dissolvability of the organic compounds of the present invention represented by Exemplary Compounds 1-1 and 1-2, and Comparative Compound 1-1 in chloroform were evaluated. The evaluation method is as follows. Each organic material was formed into 0.1 mM, and 1.0 mM chloroform solutions. Each of the solutions was diluted 5 fold with THF for HPLC. The resulting diluted solution (10 μL) was analyzed (eluent: THF/ion-exchanged water=70/30, analysis time: 60 minutes, detection wavelength: 254 nm) by high-performance liquid chromatography (LC-2010HT, manufactured by Shimadzu Corporation), to thereby obtain a chromatogram. Based on this result, calibration curves for the known concentrations (0.1 mM and 1.0 mM) were obtained. Subsequently, a saturated chloroform solution of each organic material was prepared at 25° C. After filtering the saturated solution with a filter of 0.45 μm, the solution was diluted 100 fold with THF for HPLC. The diluted solution (10 μL) was subjected to the same HPLC analysis to the above, to thereby obtain a chromatogram. The mass of the organic material dissolved in 1 mL of chloroform was determined as the dissolvability using the peak area value of the chromatogram obtained from the saturated solution, and the calibration curves prepared in advance. The results are presented in Table 1-2.

TABLE 1-2

| | Mass dissolved in 1 mL of chloroform |
|---|---|
| Compound 1-1 | 42 mg |
| Compound 1-2 | 36 mg |
| Comparative Compound 1-1 | 13 mg |

As a result, it was demonstrated that the organic compounds of the present invention had high dissolvability compared to Comparative Compound 1-1.

Example I-1

(Synthesis of Exemplary Compound 2-1
Exemplary Compound 2-1 was synthesized according to the following scheme.

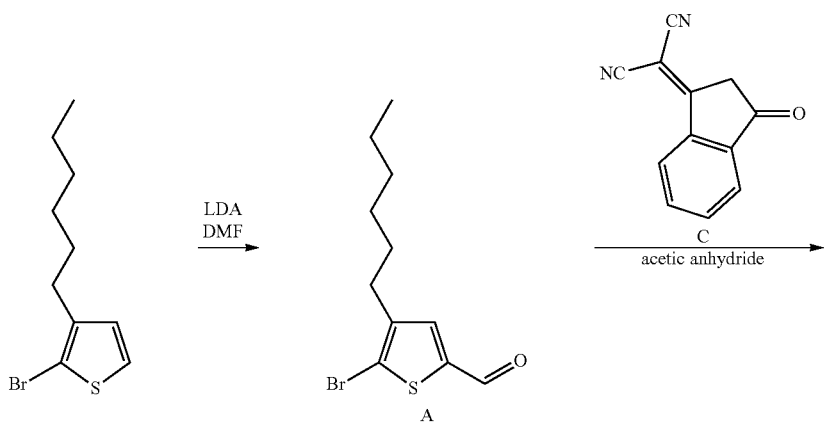

-continued

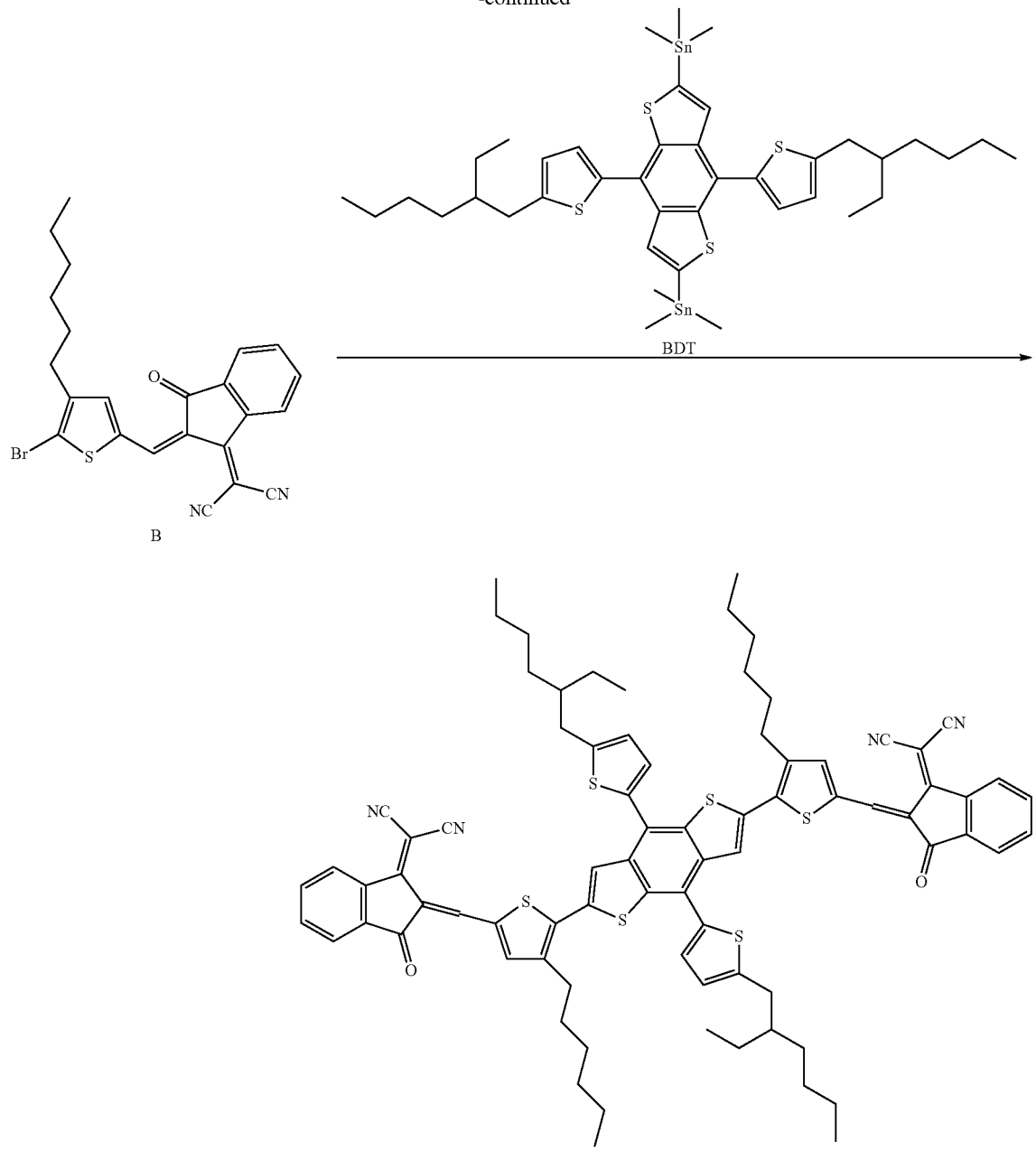

(Synthesis of A
(2-Bromo-5-formyl-3-hexylthiophene))

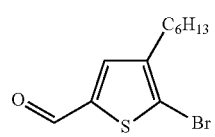

A

Schlenk flask was charged with 2-bromo-3-hexylthiophene (8.3 g, 30 mmol) and dehydrated THF (100 mL) and the mixture was stirred in a nitrogen atmosphere at −78° C. After slowly adding lithium diisopropyl amide (LDA) (15 mL, 2.0 M hexane solvent, 30 mmol) to the mixture, the resultant was stirred for 1 hour. N,N-dimethylformamide (DMF) (2.2 g, 30 mmol) was further added, and the resulting mixture was stirred for 30 minutes, followed by further stirring for 12 hours at room temperature. After adding diluted hydrochloric acid to the mixture, extraction was performed with chloroform, followed by drying with sodium sulfate, and removing the solvent by an evaporator. The reaction product was then separated by column chromatography (silica gel, chloroform:hexane=1:1), to thereby obtain orange-color oil (5.5 g, yield: 67%).

$^1$HNMR (500 MHz, CDCl$_3$): δ=9.75 (s, 1H), 7.46 (s, 1H), 2.61 (t, J=7.7 Hz, 2H), 1.64-1.58 (m, 2H), 1.36-1.34 (m, 6H), 0.85 (t, J=7.0 Hz, 3H).

Synthesis of B

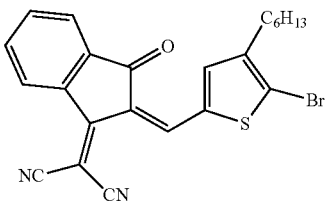

Schlenk flask was charged with A (2-bromo-5-formyl-3-hexylthiophene) (0.83 g, 3.0 mmol), (3-oxo-2,3-dihydro-1H-inden-1-ylidene)malononitrile (0.89 g, 6.0 mmol), and acetic acid anhydride (10 mL), and the resulting mixture was stirred for 24 hours at 120° C. in a nitrogen atmosphere. After returning the reaction solution to room temperature, water was added to the reaction solution, and the reaction product was extracted with chloroform, followed by drying with sodium sulfate, and removing the solvent by an evaporator. The resultant was then recrystallized in methanol, to thereby obtain a dark orange powder (0.93 g, yield: 69%).

$^1$HNMR (500 MHz, CDCl$_3$): δ=8.78 (s, 1H), (d, J=7.2 Hz, 1H), 7.95 (d, J=6.0 Hz, 1H), 7.82-7.77 (m, 2H), 7.46 (s, 1H), 2.59 (t, J=7.7 Hz, 2H), 1.65-1.58 (m, 2H), 1.35-1.23 (m, 6H), 0.91 (t, J=7 Hz, 3H).

Synthesis of Exemplary Compound 2-1

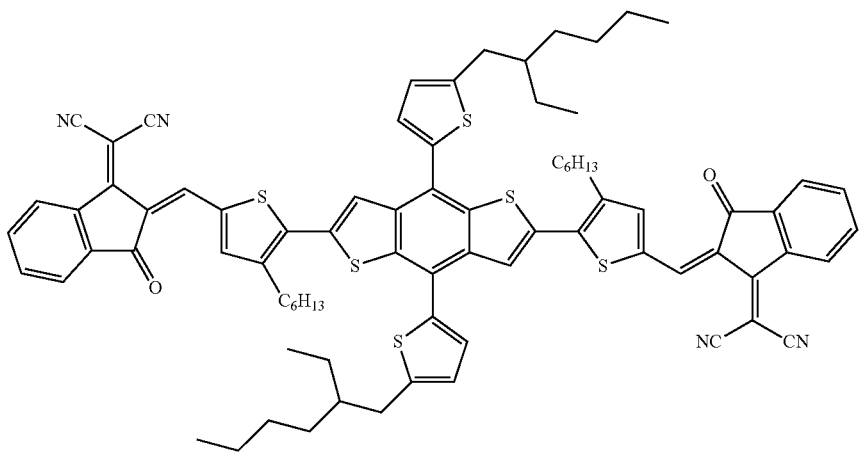

Exemplary Compound 2-1

Schlenk flask was charged with B synthesized above (0.47 g, 1.05 mmol), BDT (0.45 g, 0.5 mmol), and DMF (15 mL), and the resulting mixture was stirred in a nitrogen atmosphere. Then, Pd(PPh$_3$)$_4$ (24 mg, 0.02 mmol) was further added, and the resulting mixture was stirred for 24 hours at 85° C. After returning the reaction solution to room temperature, water was added to the reaction solution, and the reaction product was extracted with chloroform, followed by drying with sodium sulfate, and removing the solvent by an evaporator. The precipitated material was washed with ethyl acetate, separated by column chromatography (silica gel, chloroform), followed by recrystallizing in methanol, to thereby obtain a dark red powder (0.49 g, yield: 75%).

$^1$HNMR (500 MHz, CDCl$_3$): δ=8.82 (s, 2H), 8.72 (d, J=7.5 Hz, 2H), 7.97 (s, 2H), 7.95 (d, J=6.4 Hz, 2H), 7.80-7.74 (m, 4H), 7.70 (s, 2H), 7.39 (d, J=3.5 Hz, 2H), 6.97 (d, J=3.5 Hz, 2H), 2.90 (t, J=6.0 Hz, 8H), 1.76-1.68 (m, 6H), 1.52-1.23 (m, 28H), 0.98 (t, J=7.5 Hz, 6H), 0.93-0.88 (m, 12H).

Example I-2 (Synthesis of Exemplary Compound 2-2)

Exemplary Compound 2-2 was synthesized according to the following scheme.

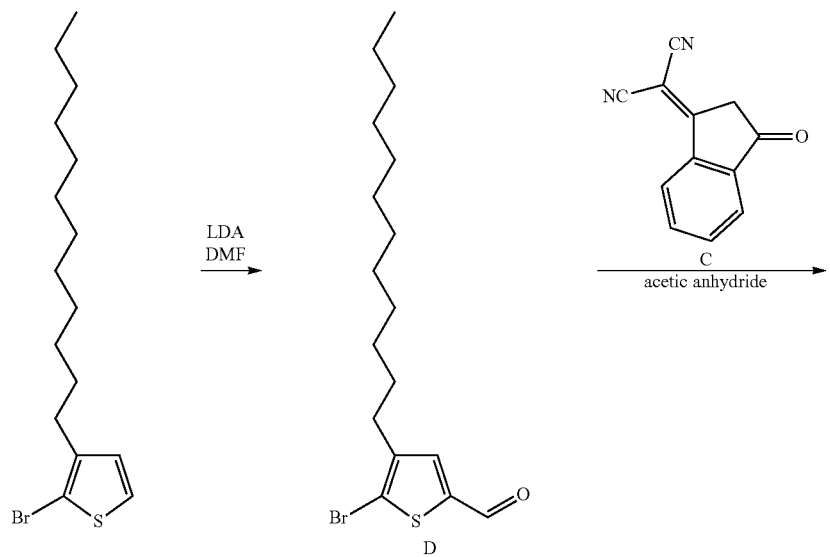
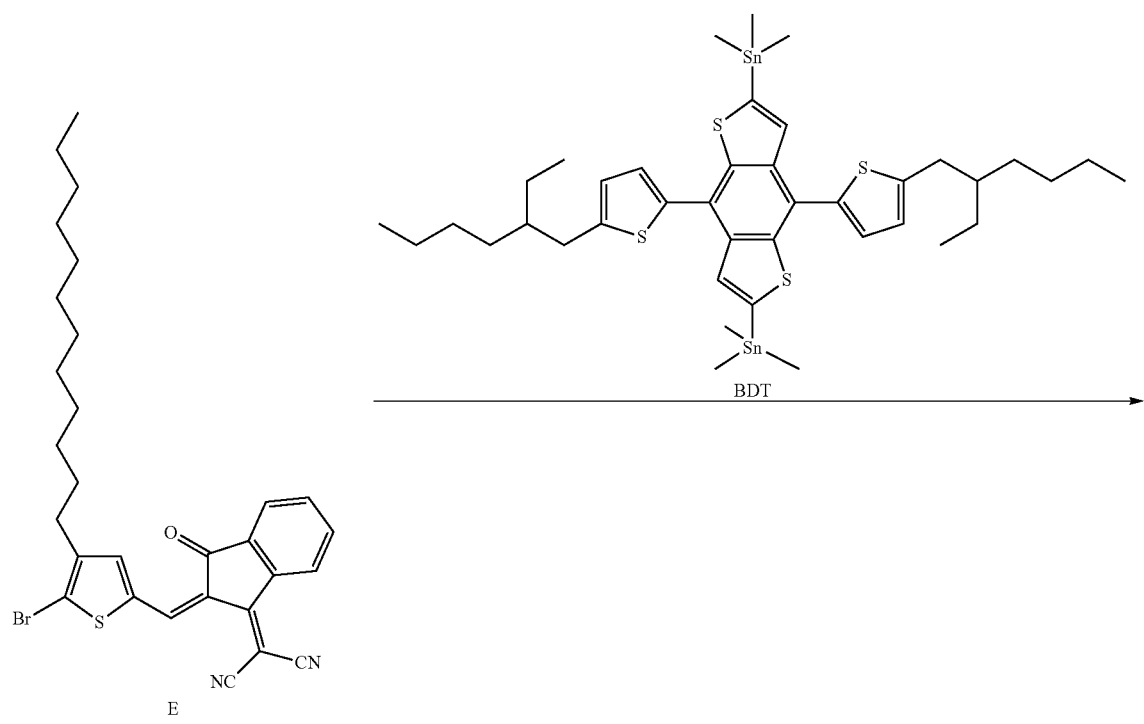

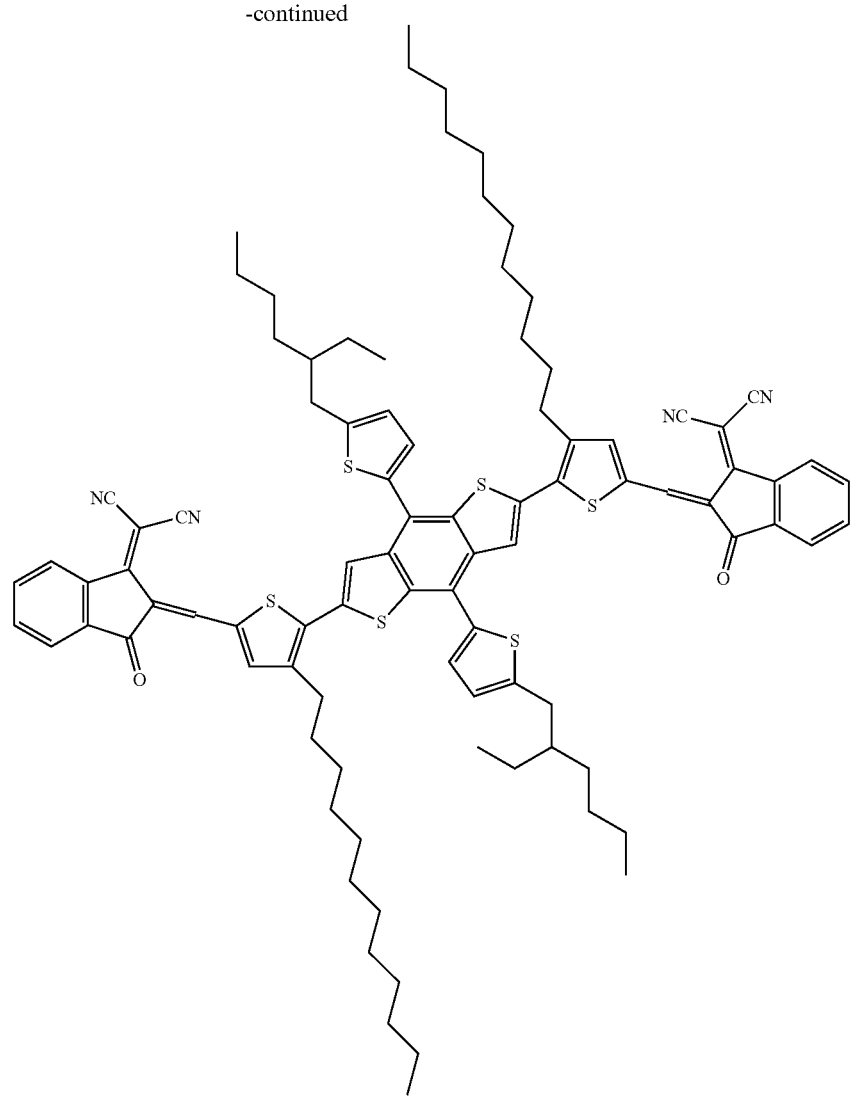

(Synthesis of D
(5-bromo-4-dodecylthiophene-2-carbaldehyde))

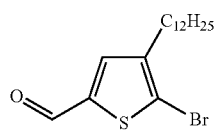

Schlenk flask was charged with 2-bromo-3-dodecylthiophene (11 g, 30 mmol) and dehydrated THF (100 mL) and the mixture was stirred in a nitrogen atmosphere at −78° C. After slowly adding lithium diisopropyl amide (LDA) (15 mL, 2.0 M hexane solvent, 30 mmol) to the mixture, the resultant was stirred for 1 hour. DMF (2.2 g, 30 mmol) was further added, and the resulting mixture was stirred for 30 minutes, followed by further stirring for 12 hours at room temperature. After adding diluted hydrochloric acid to the mixture, extraction was performed with chloroform, followed by drying with sodium sulfate, and removing the solvent by an evaporator. The reaction product was then separated by column chromatography (silica gel, chloroform:hexane=1:1), to thereby obtain orange-color oil (7.3 g, yield: 68%).

$^{1}$HNMR (500 MHz, CDCl$_{3}$): δ=9.75 (s, 1H), 7.46 (s, 1H), 2.61 (t, J=7.7 Hz, 2H), 1.65-1.58 (m, 2H), 1.36-1.33 (m, 18H), 0.85 (t, J=7.0 Hz, 3H).

Synthesis of E

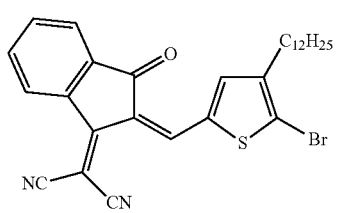

Schlenk flask was charged with D (5-bromo-4-dodecylthiophene-2-carbaldehyde) (1.1 g, 3.0 mmol), (3-oxo-2,3-dihydro-1H-inden-1-ylidene)malononitrile (0.89 g, 6.0 mmol), and acetic acid anhydride (10 mL), and the resulting mixture was stirred for 24 hours at 120° C. in a nitrogen atmosphere. After returning the reaction solution to room temperature, water was added to the reaction solution, and the reaction product was extracted with chloroform, followed by drying with sodium sulfate, and removing the solvent by an evaporator. The resultant was then recrystallized in methanol, to thereby obtain a dark orange powder (0.63 g, yield: 38%).

$^1$HNMR (500 MHz, CDCl$_3$): δ=8.77 (s, 1H), 8.72 (d, J=7.2 Hz, 1H), 7.95 (d, J=6.0 Hz, 1H), 7.82-7.76 (m, 2H), 7.46 (s, 1H), 2.57 (d, J=7.3 Hz, 2H), 1.67-1.62 (m, 2H), 1.37-1.23 (m, 18H), 0.91 (t, J=7 Hz, 3H).

Synthesis of Exemplary Compound 2-2

Exemplary Compound 2-2

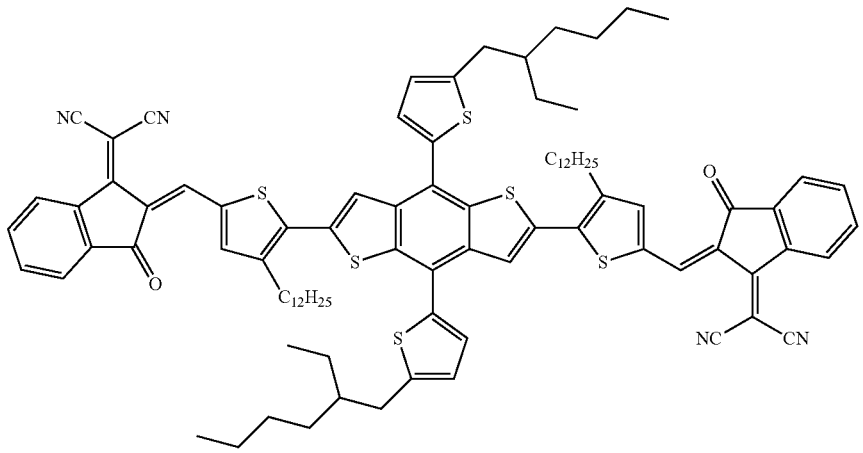

25

Schlenk flask was charged with E synthesized above (0.59 g, 1.05 mmol), BDT (0.45 g, 0.5 mmol), and DMF (15 mL), and the resulting mixture was stirred in a nitrogen atmosphere. Then, Pd(PPh$_3$)$_4$ (24 mg, 0.02 mmol) was further added, and the resulting mixture was stirred for 24 hours at 85° C. After returning the reaction solution to room temperature, water was added to the reaction solution, and the reaction product was extracted with chloroform, followed by drying with sodium sulfate, and removing the solvent by an evaporator. The precipitated material was washed with ethyl acetate, separated by column chromatography (silica gel, chloroform), followed by recrystallizing in methanol, to thereby obtain a dark blue powder (0.69 g, yield: 88%).

$^1$HNMR (500 MHz, CDCl$_3$): δ=8.81 (s, 2H), 8.71 (d, J=7.5 Hz, 2H), 7.95 (s, 2H), 7.94 (d, J=6.4 Hz, 4H), 7.80-7.74 (m, 4H), 7.70 (s, 2H), 7.40 (d, J=3.5 Hz, 2H), 6.97 (d, J=3.5 Hz, 2H), 2.92-2.87 (m, 8H), 1.76-1.67 (m, 6H), 1.51-1.24 (m, 52H), 0.98 (t, J=7.5 Hz, 6H), 0.92 (t, J=7.5 Hz, 6H), 0.87 (t, J=7.5 Hz, 6H).

Example I-3 (Synthesis of Exemplary Compound 2-4)

Exemplary Compound 2-4 was synthesized according to the following scheme.

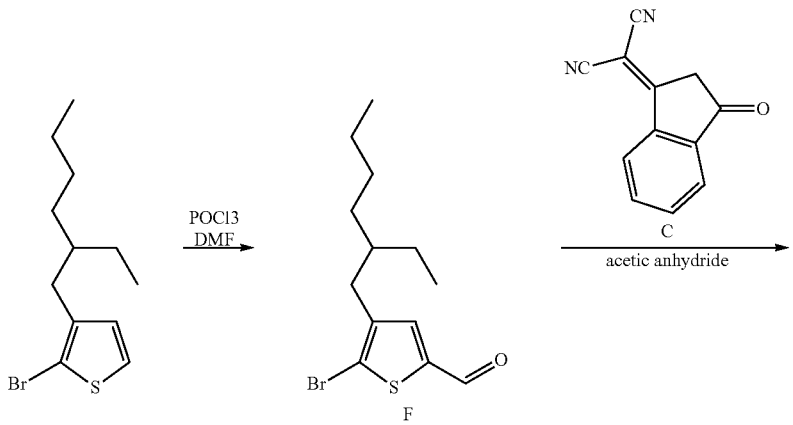

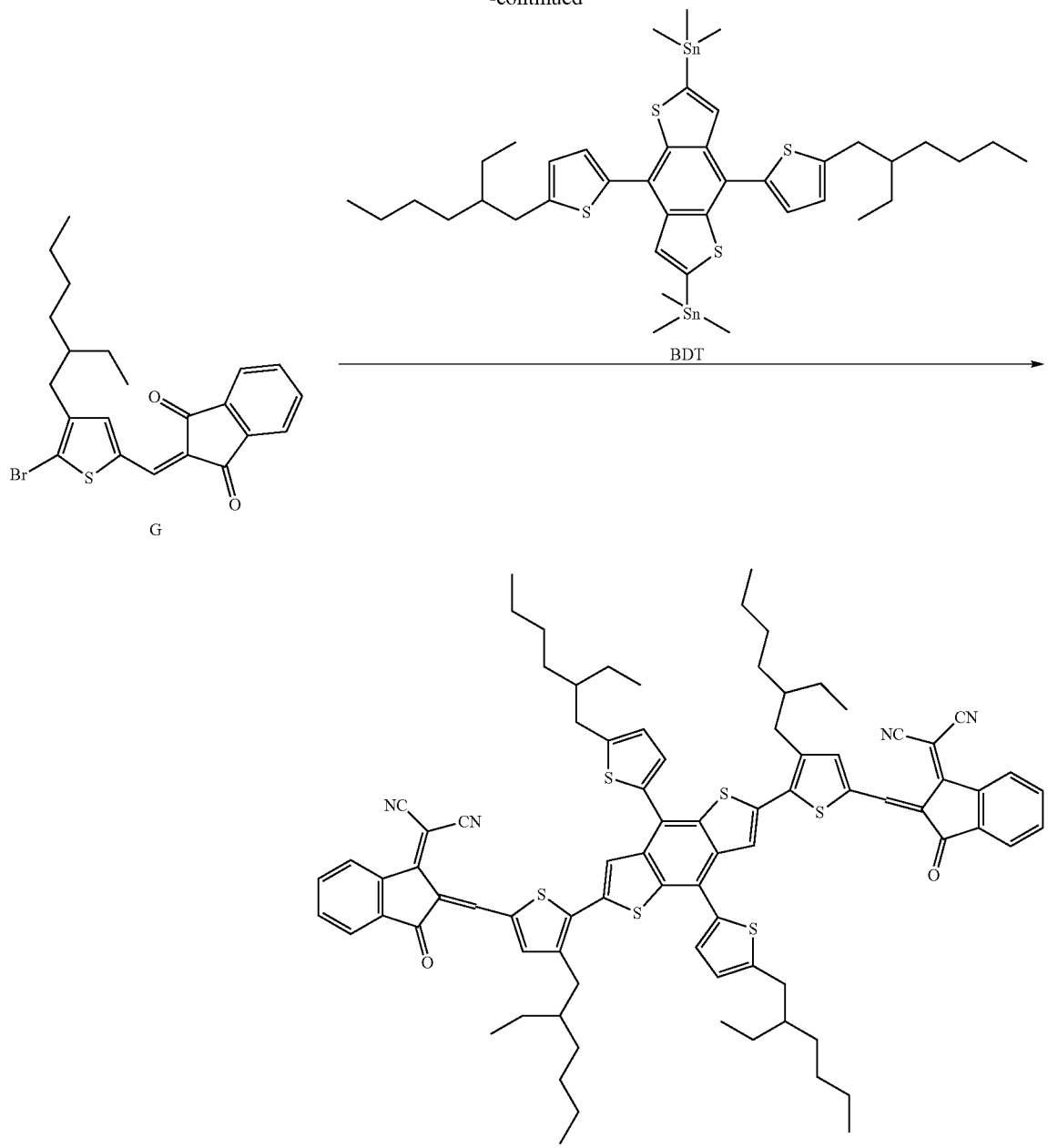

Synthesis of G

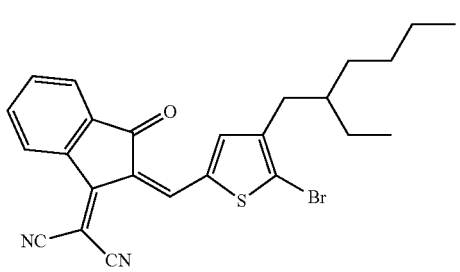

Schlenk flask was charged with 5-bromo-4-(2-ethylhexyl)thiophene-2-carbaldehyde (1.0 g, 3.3 mmol), (3-oxo-2,3-dihydro-1H-inden-1-ylidene)malononitrile (1.3 g, 6.6 mmol), and acetic acid anhydride (10 mL), and the mixture was stirred in a nitrogen atmosphere for 24 hours at 120° C. After returning the reaction solution to room temperature, water was added to the reaction solution, and the reaction product was extracted with chloroform, followed by drying with sodium sulfate, and removing the solvent by an evaporator. The resultant was then recrystallized in methanol, to thereby obtain a dark orange powder (0.99 g, yield: 49%).

$^1$HNMR (500 MHz, CDCl$_3$): δ8.76 (s, 1H), 8.70 (d, J=7.2 Hz, 1H), 7.94 (d, J=6.0 Hz, 1H), 7.82-7.75 (m, 2H), 7.46 (s, 1H), 2.56 (d, J=7.3 Hz, 2H), 1.67-1.62 (m, 1H), 1.35-1.22 (m, 8H), 0.92-0.87 (m, 6H).

Synthesis of Exemplary Compound 2-4

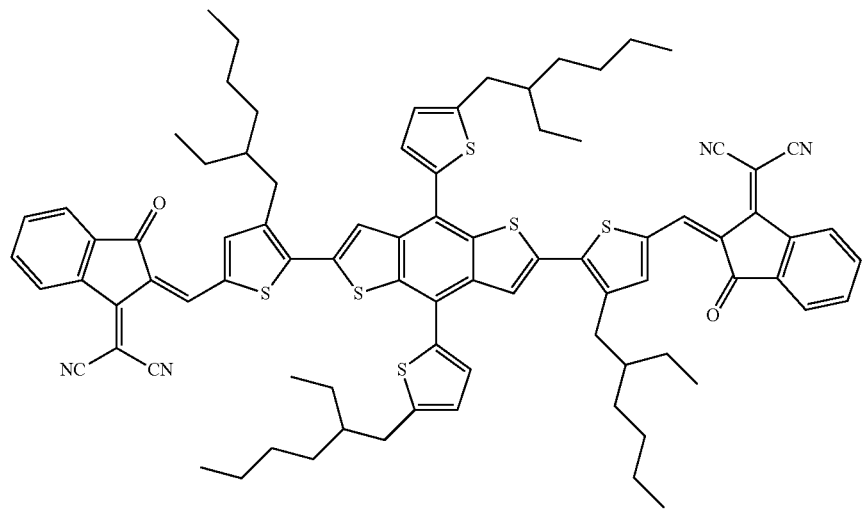

Exemplary Compound 2-4

Schlenk flask was charged with G synthesized above (0.53 g, 1.05 mmol), BDT (0.45 g, 0.5 mmol), and DMF (15 mL), and the resulting is mixture was stirred in a nitrogen atmosphere. Then, Pd(PPh$_3$)$_4$ (24 mg, 0.02 mmol) was further added, and the resulting mixture was stirred for 24 hours at 85° C. After returning the reaction solution to room temperature, water was added to the reaction solution, and the reaction product was extracted with chloroform, followed by drying with sodium sulfate, and removing the solvent by an evaporator. The precipitated material was washed with ethyl acetate, separated by column chromatography (silica gel, chloroform), followed by recrystallizing in methanol, to thereby obtain a dark blue powder (0.21 g, yield: 31%).

$^1$HNMR (500 MHz, CDCl$_3$): δ=8.82 (s, 2H), 8.72 (d, J=7.5 Hz, 2H), 7.95 (s, 2H), 7.94 (d, J=6.4 Hz, 2H), 7.81-7.74 (m, 4H), 7.66 (s, 2H), 7.37 (d, J=3.5 Hz, 2H), 6.96 (d, J=3.5 Hz, 2H), 2.91 (d, J=6.7 Hz, 4H), 2.85 (q, J=6.7 Hz, 4H), 1.74-1.72 (m, 4H), 1.51-1.23 (m, 32H), 0.99-0.83 (m, 24H).

Example II-1

(Formation of Electron-Transporting Layer)
At room temperature, 1 g of zinc acetate (of SIGMA-ALDRICH), 0.28 g of ethanol amine (of SIGMA-ALDRICH), and 10 mL of methoxyethanol (manufactured by Wako Pure Chemical Industries, Ltd.) were stirred all night, to thereby prepare a zinc oxide precursor solution. The zinc oxide precursor solution was applied onto a glass substrate with ITO by spin coating to give a film thickness of 20 nm, followed by drying for 10 minutes at 200° C., to thereby form an electron-transporting layer.

(Formation of Photoelectric Conversion Layer)
In 1 mL of chloroform, 7.5 mg of Exemplary Compound 2-2 and 7.5 mg of N,N'-bis(2-ethylhexyl)-3,4,9,10-perylenetetracarboxylic diimide (manufactured by Tokyo Chemical Industry Co., Ltd.) were dissolved, to thereby produce a solution for forming a photoelectric conversion layer. Onto the electron-transporting layer, the solution for forming a photoelectric conversion layer was applied by spin coating to give a film thickness of 100 nm, to thereby form a photoelectric conversion layer.

(Formation of Hole-Transporting Layer and Metal Electrode)
On the photoelectric conversion layer, 20 nm of molybdenum oxide (manufactured by Kojundo Chemical Laboratory Co., Ltd.), and 100 nm of silver were sequentially deposited by vacuum vapor deposition, to thereby produce a photoelectric conversion element.

The open-circuit voltage of the obtained photoelectric conversion element was measured under which LED irradiation (three points, 50 lux (0.0125 mW/cm$^2$), 200 lux (0.05 mW/cm$^2$), and 1,000 lux (0.25 mW/cm$^2$)).

The measurement was performed by using a desk lamp CDS-90α (study mode) manufactured by Cosmotechno Co., Ltd. as the white LED, and a solar battery evaluation system As-510-PV03 manufactured by NF Corporation as the evaluation device. The results are presented in Table 2-1.

Example II-2

A photoelectric conversion element was produced in the same manner as in Example II-1, provided that N,N'-bis(2-ethylhexyl)-3,4,9,10-perylenetetracarboxylic diimide (manufactured by Tokyo Chemical Industry Co., Ltd.) was replaced with PC71BM (manufactured by Frontier Carbon Corporation). The produced photoelectric conversion element was evaluated in the same manner as in Example II-1. The results are presented in Table 2-1.

Example II-3

(Formation of Hole-Transporting Layer)
Onto a glass substrate with ITO, a PEDOT:PSS (polyethylene dioxythiophene:polystyrene sulfonate, CleviosP VP AI4083 manufactured by H. C. Stark GmbH) solution was applied by spin coating to give a film thickness of 20 nm. The applied solution was dried for 10 minutes at 130° C., to thereby form a hole-transporting layer.

(Production of Photoelectric Conversion Layer)
In 1 mL of chloroform, 7.5 mg of Exemplary Compound 2 and 7.5 mg of PC71BM (manufactured by Frontier Carbon Corporation) were dissolved, to thereby prepare a solution for forming a photoelectric conversion layer. Onto the hole-transporting layer, the solution for forming a photoelectric conversion layer was applied by spin coating to give a film thickness of 100 nm, to thereby form a photoelectric conversion layer.

(Formation of Electron-Transporting Layer and Second Electrode)

Subsequently, a film of lithium fluoride in the thickness of 1 nm, and a Al electrode in the thickness of 80 nm were formed on the photoelectric conversion layer by vacuum vapor deposition at $1 \times 10^{-6}$ Torr, to thereby produce a photoelectric conversion element.

The produced photoelectric conversion element was evaluated in the same manner as in Example II-1. The results are presented in Table 2-1.

Example II-4

A photoelectric conversion element was produced in the same manner as in Example II-2, provided that Exemplary Compound 2-2 was replaced with Exemplary Compound 2-1. The produced photoelectric conversion element was evaluated in the same manner as in Example II-2. The results are presented in Table 2-1.

Example II-5

A photoelectric conversion element was produced in the same manner as in Example II-2, provided that Exemplary Compound 2-2 was replaced with Exemplary Compound 2-4. The produced photoelectric conversion element was evaluated in the same manner as in Example II-2. The results are presented in Table 2-1.

Example II-6

A photoelectric conversion element was produced in the same manner as in Example II-2, provided that Exemplary Compound 2-2 was replaced with Exemplary Compound 2-10. The produced photoelectric conversion element was evaluated in the same manner as in Example II-2. The results are presented in Table 2-1.

Example II-7

A photoelectric conversion element was produced in the same manner as in Example II-2, provided that Exemplary Compound 2-2 was replaced with Exemplary Compound 2-12. The produced photoelectric conversion element was evaluated in the same manner as in Example II-2. The results are presented in Table 2-1.

Example II-8

A photoelectric conversion element was produced in the same manner as in Example II-2, provided that Exemplary Compound 2-2 was replaced with Exemplary Compound 2-17. The produced photoelectric conversion element was evaluated in the same manner as in Example II-2. The results are presented in Table 2-1.

Example II-9

A photoelectric conversion element was produced in the same manner as in Example 11-2, provided that Exemplary Compound 2-2 was replaced with Exemplary Compound 2-21. The produced photoelectric conversion element was evaluated in the same manner as in Example II-2. The results are presented in Table 2-1.

Comparative Example II-1

A photoelectric conversion element was produced in the same manner as in Example II-1, provided that Exemplary Compound 2 was replaced with Comparative Compound 2-1, which was represented below, and described in Literature A below. The produced photoelectric conversion element was evaluated in the same manner as in Example II-1. Comparative Compound 2-1 was synthesized by the method described in Literature A below. The results are presented in Table 2-1.

Literature A: Chem. Mater. 2013, 25, 2274-2281

Comparative Compound 2-1

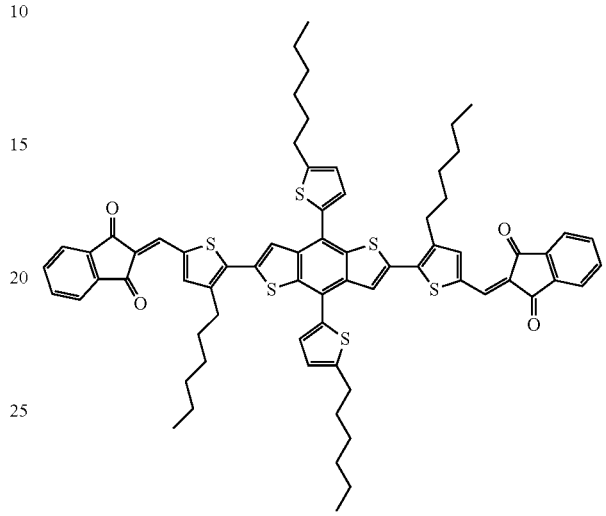

Comparative Example II-2

A photoelectric conversion element was produced in the same manner as in Example II-2, provided that Exemplary Compound 2-2 was replaced with Comparative Compound 2-1 described in Literature A above. The produced photoelectric conversion element was evaluated in the same manner as in Example II-1. The results are presented in Table 2-1.

Comparative Example II-3

A photoelectric conversion element was produced in the same manner as in Example II-3, provided that Exemplary Compound 2-2 was replaced with Comparative Compound 2-1 described in Literature A above. The produced photoelectric conversion element was evaluated in the same manner as in Example II-1. The results are presented in Table 2-1.

Comparative Example II-4

A photoelectric conversion element was produced in the same manner as in Example II-2, provided that Exemplary Compound 2-2 was replaced with PTB7 (manufactured by 1-Material). The produced photoelectric conversion element was evaluated in the same manner as in Example II-1. The results are presented in Table 2-1.

TABLE 2-1

| | Open-circuit voltage (V) with LED (50 lux, 0.0125 mW/cm$^2$) | Open-circuit voltage (V) with LED (200 lux, 0.05 mW/cm$^2$) | Open-circuit voltage (V) with LED (1,000 lux, 0.25 mW/cm$^2$) |
|---|---|---|---|
| Ex. II-1 | 0.60 | 0.63 | 0.70 |
| Ex. II-2 | 0.83 | 0.85 | 0.89 |
| Ex. II-3 | 0.82 | 0.84 | 0.88 |
| Ex. II-4 | 0.80 | 0.83 | 0.85 |

TABLE 2-1-continued

| | Open-circuit voltage (V) with LED (50 lux, 0.0125 mW/cm$^2$) | Open-circuit voltage (V) with LED (200 lux, 0.05 mW/cm$^2$) | Open-circuit voltage (V) with LED (1,000 lux, 0.25 mW/cm$^2$) |
|---|---|---|---|
| Ex. II-5 | 0.81 | 0.84 | 0.86 |
| Ex. II-6 | 0.80 | 0.82 | 0.84 |
| Ex. II-7 | 0.78 | 0.81 | 0.83 |
| Ex. II-8 | 0.76 | 0.79 | 0.81 |
| Ex. II-9 | 0.76 | 0.79 | 0.81 |
| Comp. Ex. II-1 | 0.40 | 0.47 | 0.51 |
| Comp. Ex. II-2 | 0.68 | 0.74 | 0.76 |
| Comp. Ex. II-4 | 0.65 | 0.71 | 0.74 |
| Comp. Ex. II-5 | 0.44 | 0.52 | 0.61 |

It was demonstrated that the photoelectric conversion elements of the present invention had high open-circuit voltage with weak light, 50 lux, 200 lux, and 1,000 lux of LED, compared to the photoelectric conversion elements of Comparative Examples.

For example, the embodiments of the present invention are as follows.

<1> An organic compound represented by the following general formula (1):

<General Formula (1)>

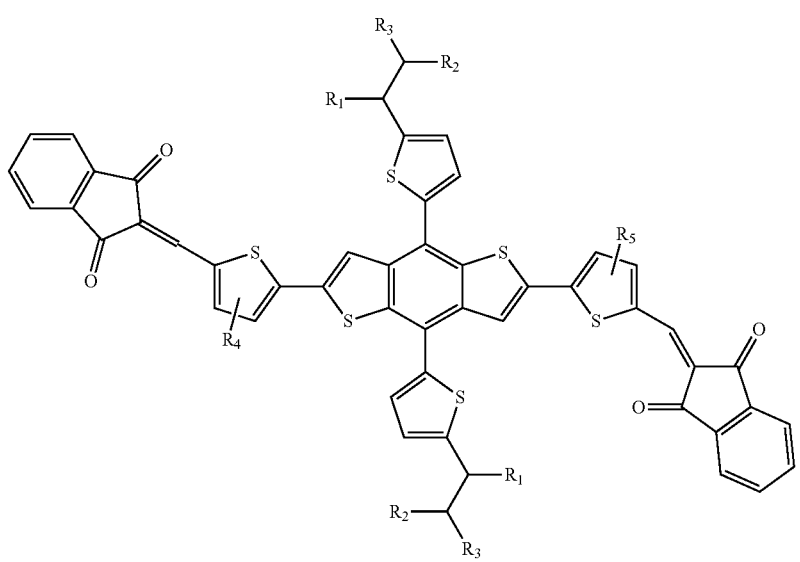

where $R_1$ is a C2-C6 alkyl group or a hydrogen atom, $R_2$ and $R_3$, which may be identical or different, are each a C2-C12 alkyl group, and $R_4$ and $R_5$, which may be identical or different, are each a C6-C12 alkyl group that may be a branched chain or a straight chain.

<2> An organic compound represented by the following general formula (2):

<General Formula (2)>

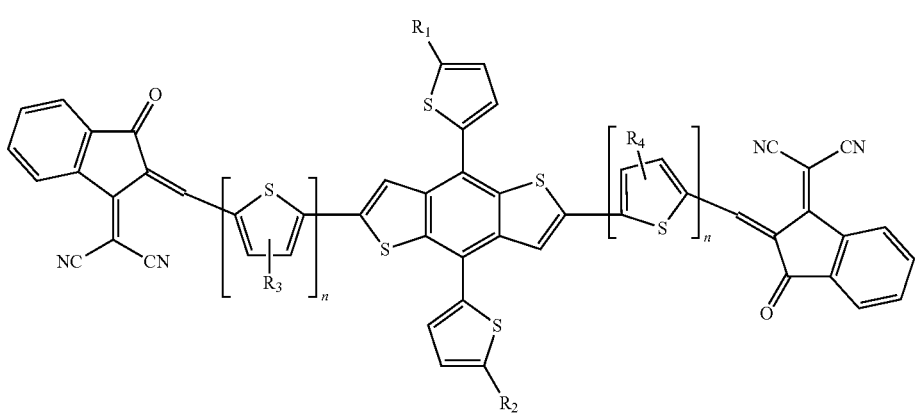

where $R_1$ and $R_2$, which may be identical or different, are each a C6-C22 alkyl group that may be a branched chain or a straight chain, $R_3$ and $R_4$, which may be identical or different, are each a hydrogen atom or a C2-C16 alkyl group that may be a branched chain or a straight chain, and n is an integer of 1, 2, or 3.

<3> A thin organic-material film including:
the organic compound according to <1>; and
a n-type organic material.

<4> The thin organic-material film according to <3>, wherein the n-type organic material is a fullerene derivative.

<5> A photoelectric conversion layer, including the thin organic-material film according to <3> or <4>.

<6> A solution for forming a photoelectric conversion layer, the solution including:
the organic compound according to <1>;
a n-type organic material; and
an organic solvent.

<7>. The solution for forming a photoelectric conversion layer according to <6>, wherein the n-type organic material is a fullerene derivative.

<8> A photoelectric conversion element including:
a substrate;
a first electrode;
an electron-transporting layer;
a photoelectric conversion layer;
a hole-transporting layer; and
a second electrode, where the first electrode, the electron-transporting layer, the photoelectric conversion layer, the hole-transporting layer, and the second electrode are disposed on the substrate in this order,
wherein the photoelectric conversion layer is the photoelectric conversion layer according to <5>.

<9> A photoelectric conversion element including:
a substrate;
a first electrode;
a hole-transporting layer;
a photoelectric conversion element;
an electron-transporting layer; and
a second electrode, where the first electrode, the hole-transporting layer, the photoelectric conversion element, the electron-transporting layer, and the second electrode are disposed on the substrate in this order,
wherein the photoelectric conversion layer is the photoelectric conversion layer according to <5>.

<10> The photoelectric conversion element according to <8> or <9>,
wherein the electron-transporting layer contains metal oxide.

<11> A photoelectric conversion element including:
a first electrode;
a second electrode; and
a photoelectric conversion layer disposed between the first electrode and the second electrode,
wherein the photoelectric conversion layer contains the organic compound according to <2>.

<12> The photoelectric conversion element according to <11>, wherein the photoelectric conversion layer further contains a n-type organic semiconductor.

<13> The photoelectric conversion element according to <12>, wherein the n-type organic semiconductor is a fullerene derivative.

<14> The photoelectric conversion element according to any one of <11> to <13>, wherein the first electrode, an electron-transporting layer, the photoelectric conversion layer, a hole-transporting layer, and the second electrode are disposed on a substrate in this order.

<15> The photoelectric conversion element according to any one of <11> to <13>, wherein the first electrode, a hole-transporting layer, the photoelectric conversion layer, an electron-transporting layer, and the second electrode are disposed on a substrate in this order.

What is claimed is:
1. An organic compound represented by one of the following formulas (1-2) to (1-8) and stereoisomers thereof:

(1-2)
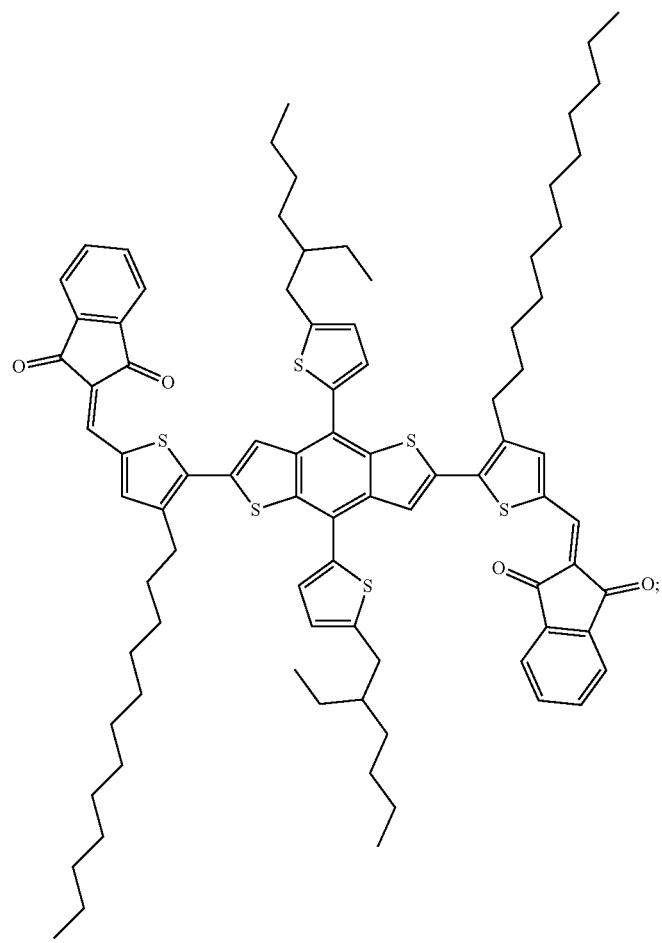
(1-3)
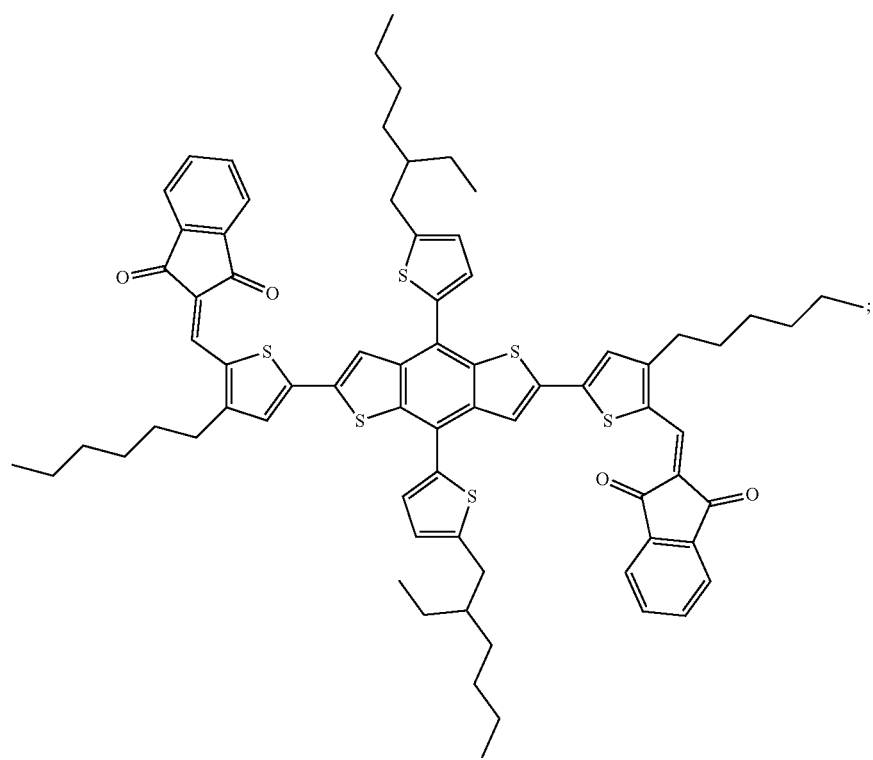

(1-4)
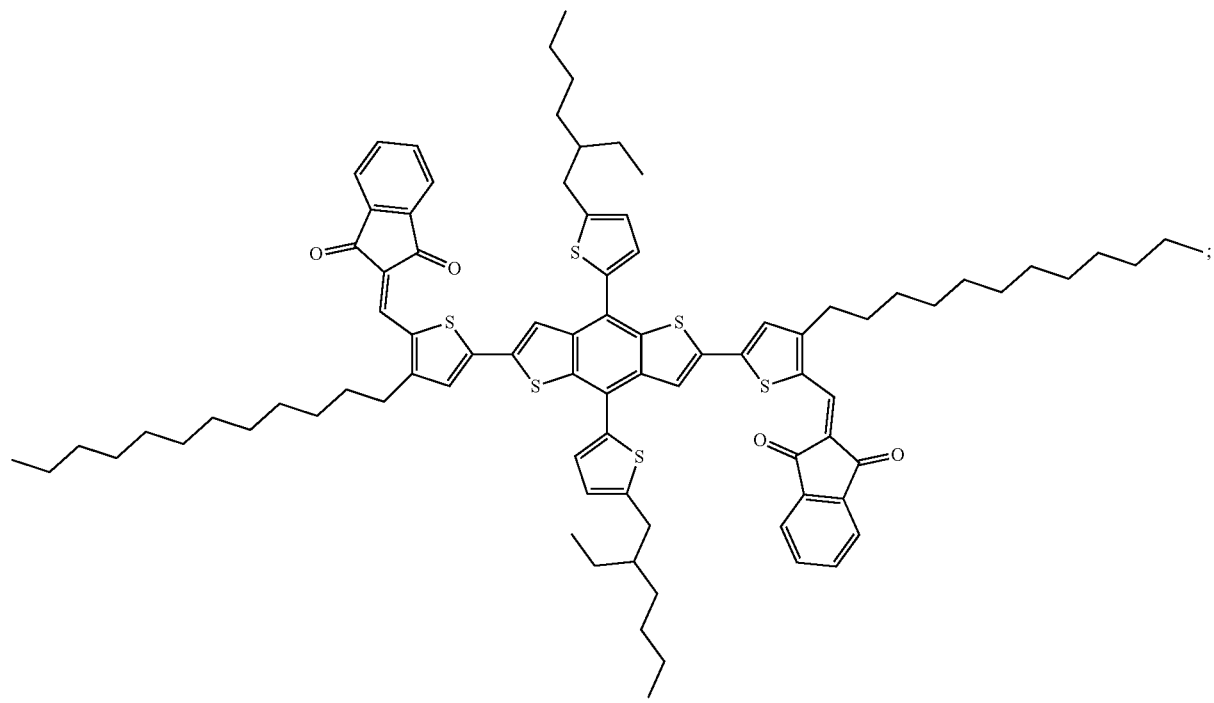
(1-5)
(1-6)
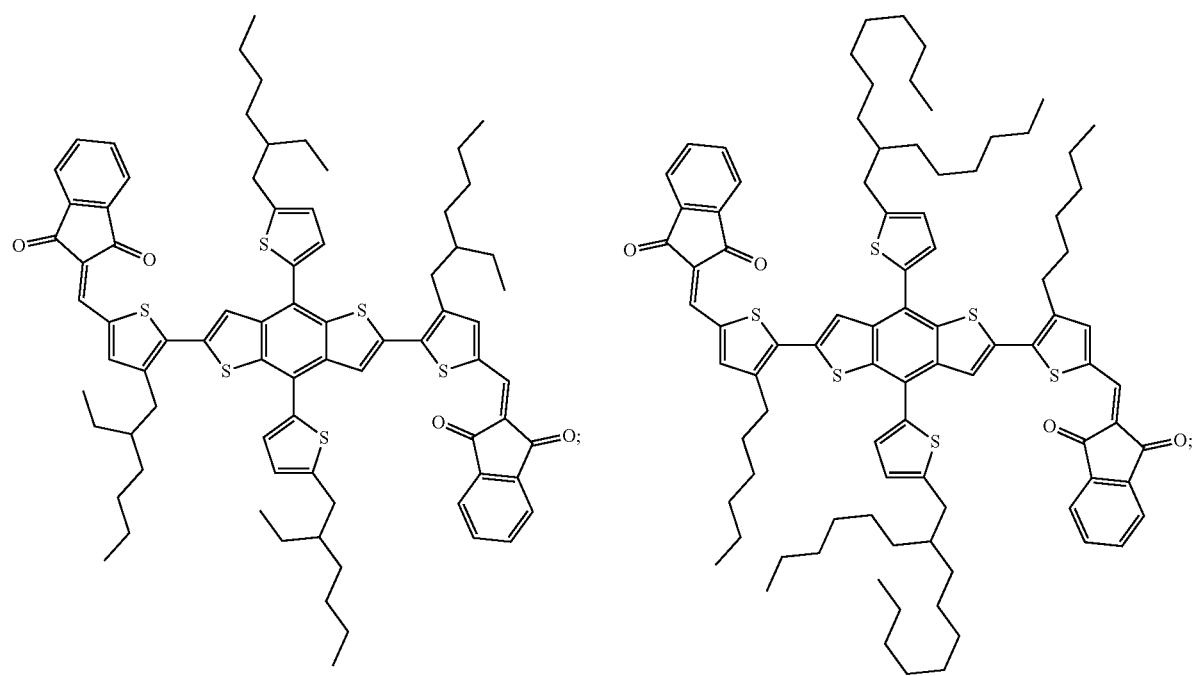

(1-7)
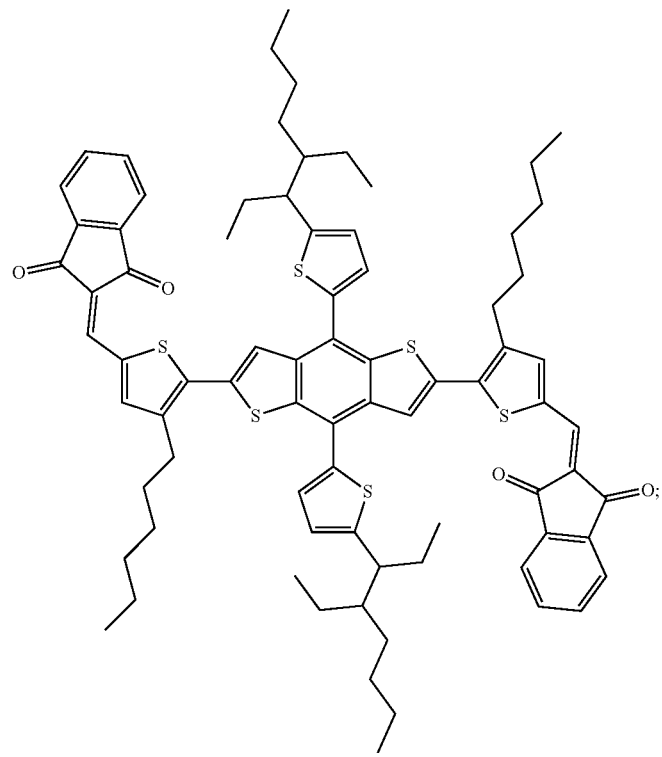
(1-8)
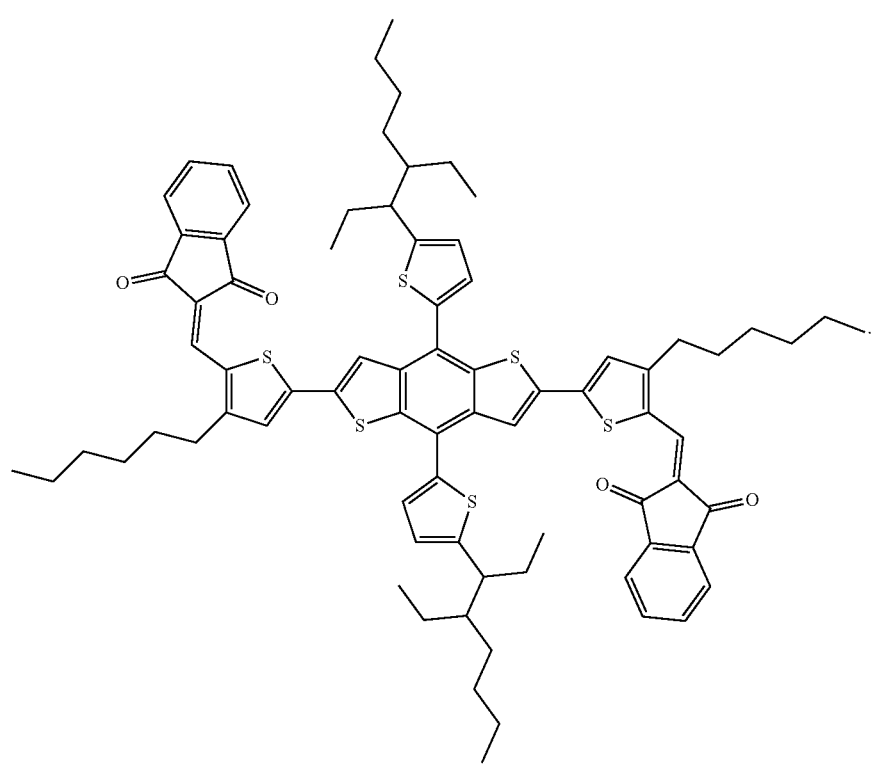
2. An organic compound represented by one of the following formulas (2-2) to (2-24) and stereoisomers thereof:

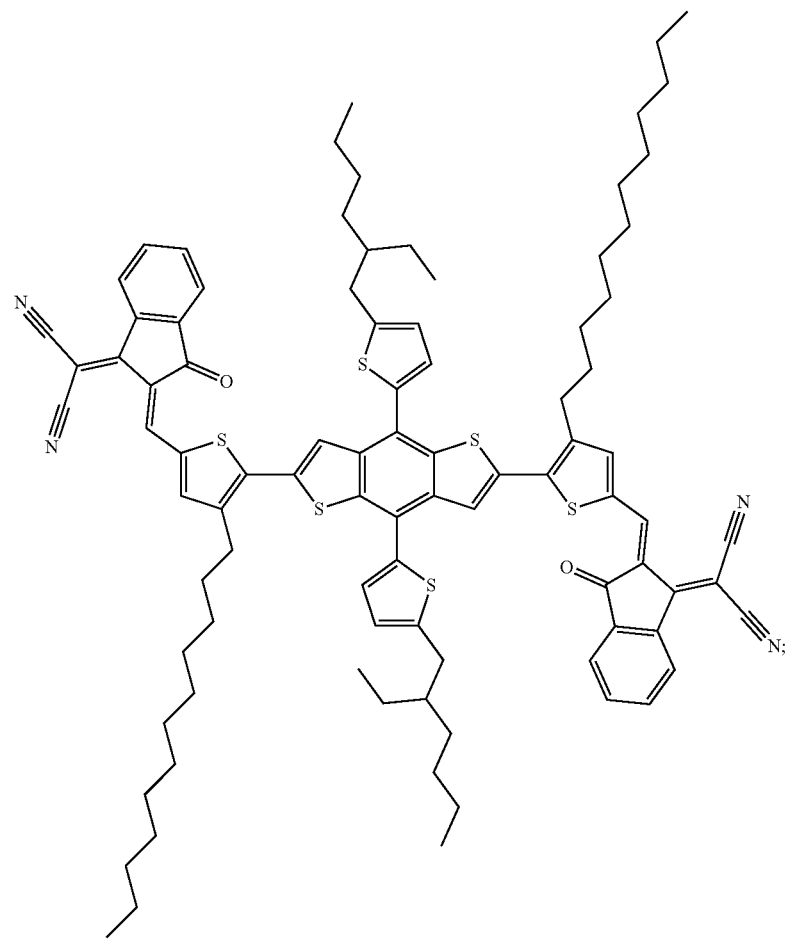
(2-2)
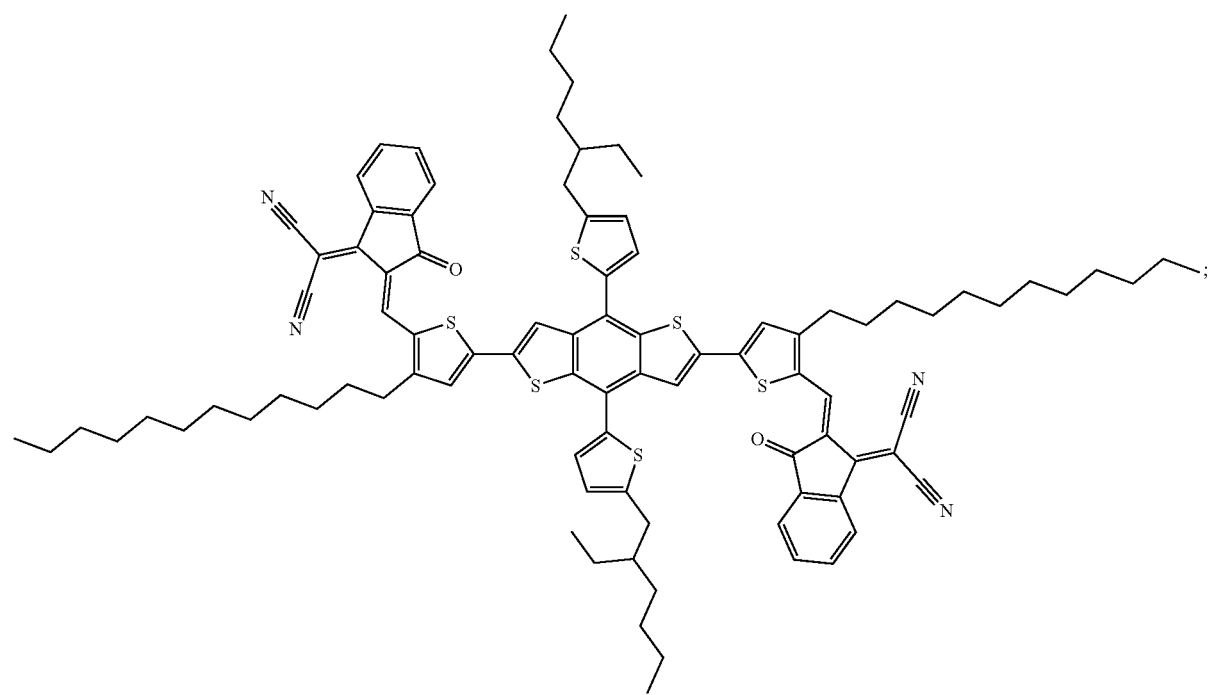
(2-3)

(2-4)
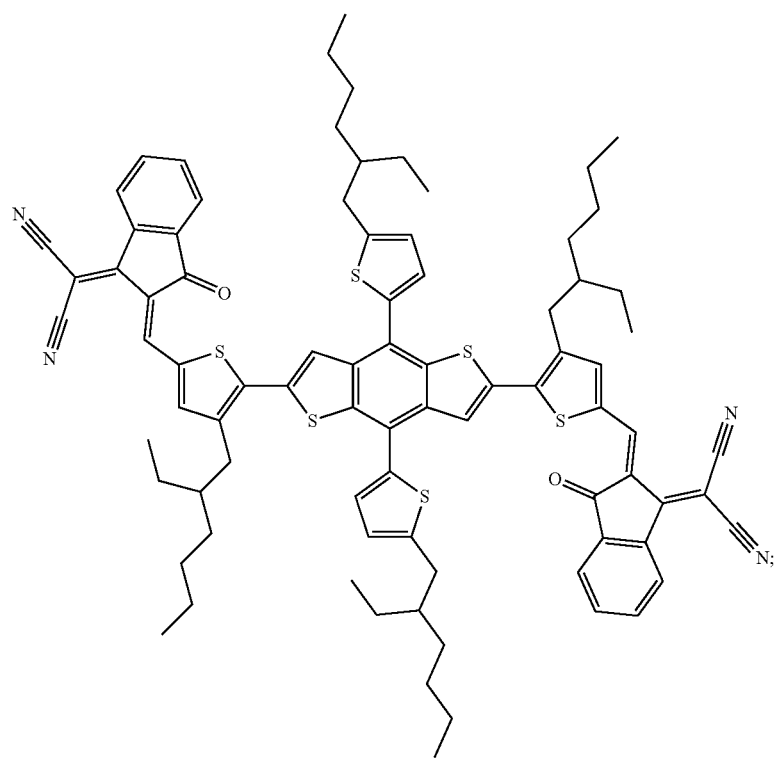
(2-5)
(2-6)
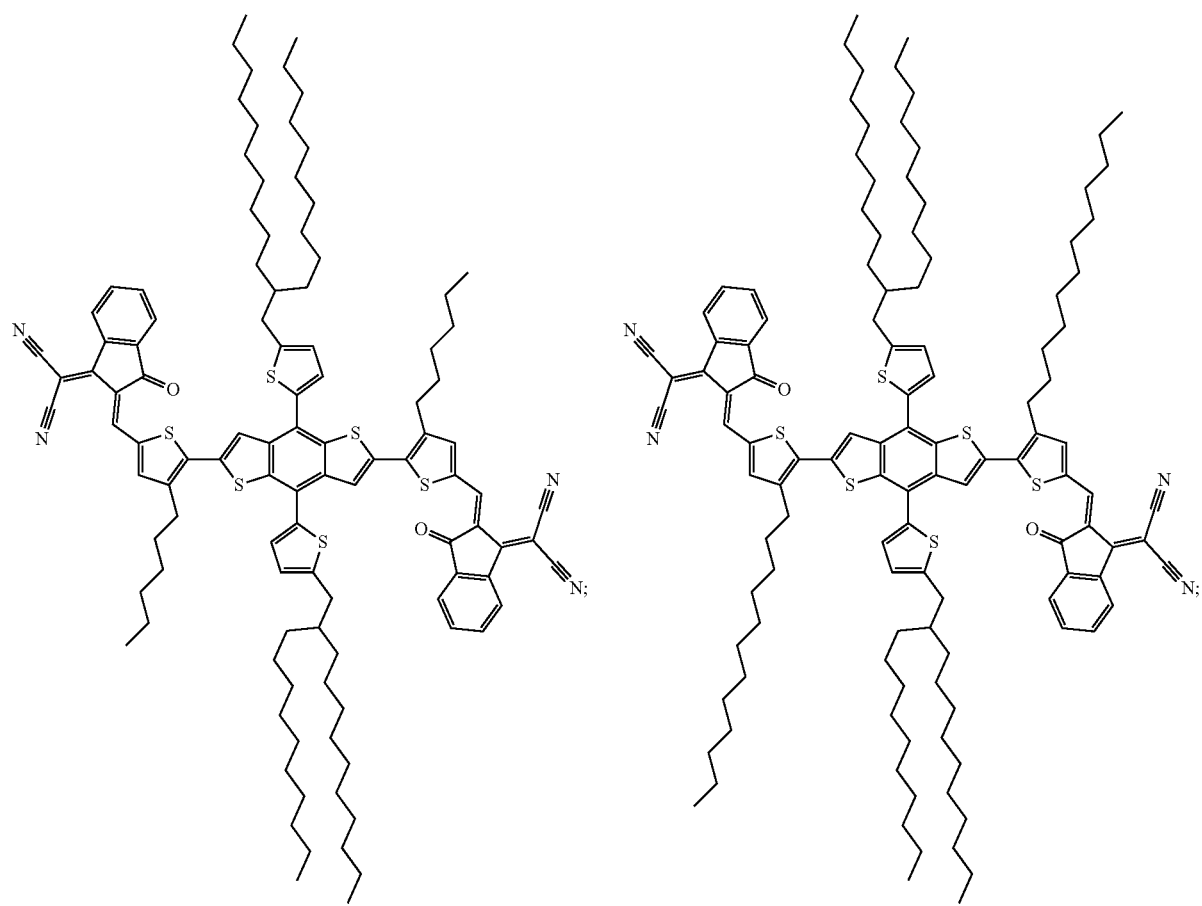

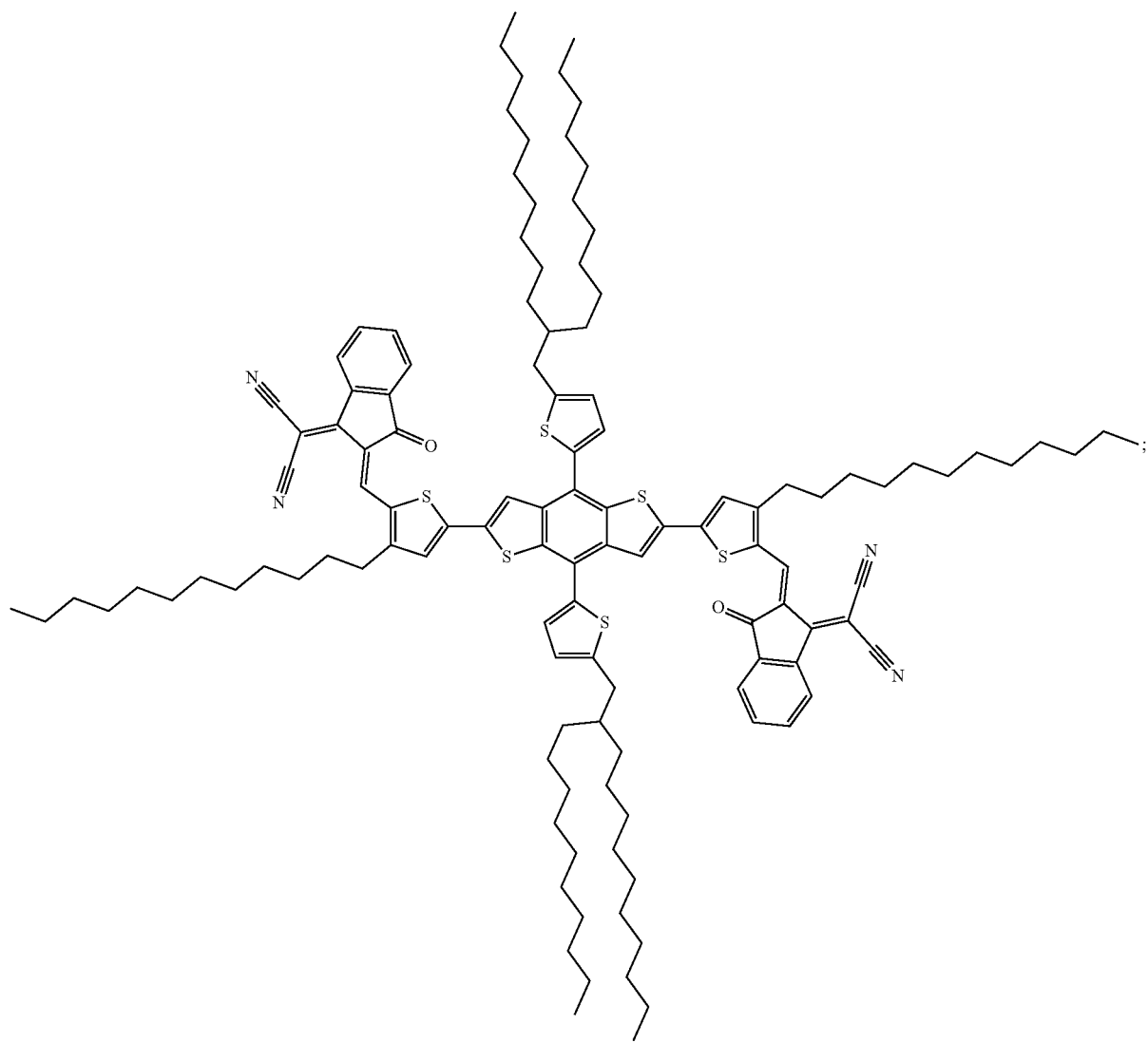
(2-7)

(2-8)
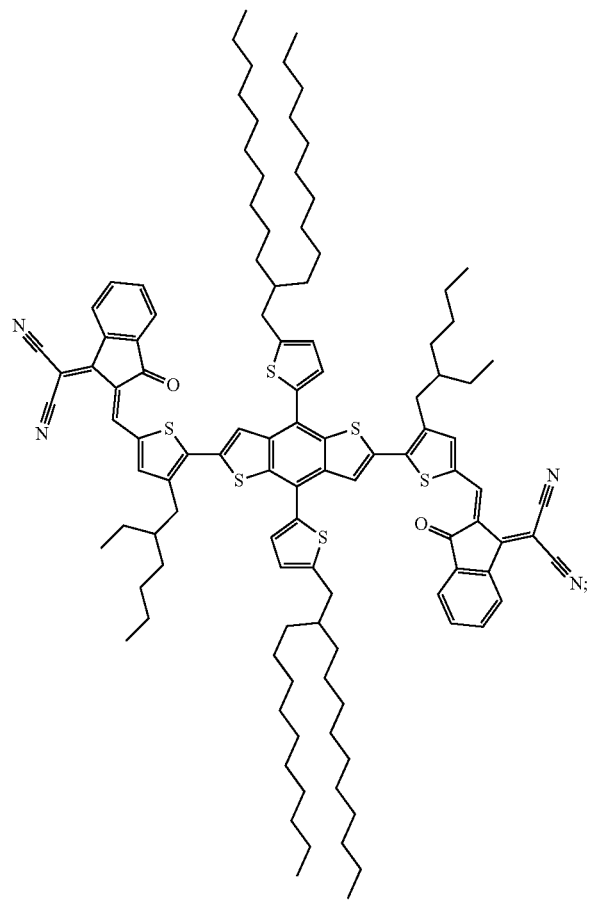
(2-9)
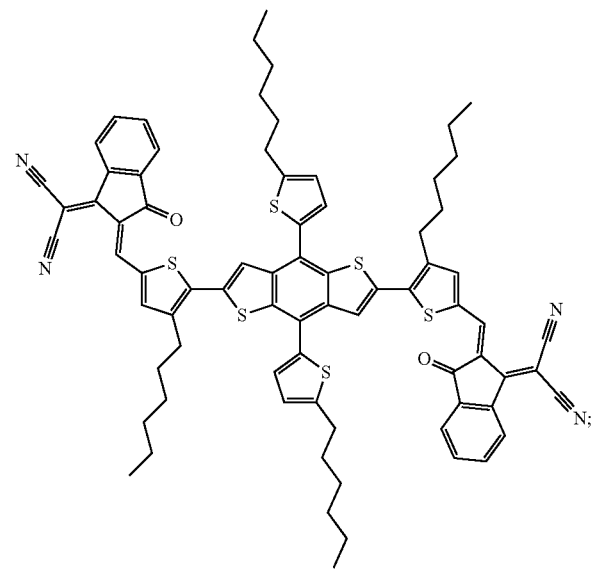

(2-10)
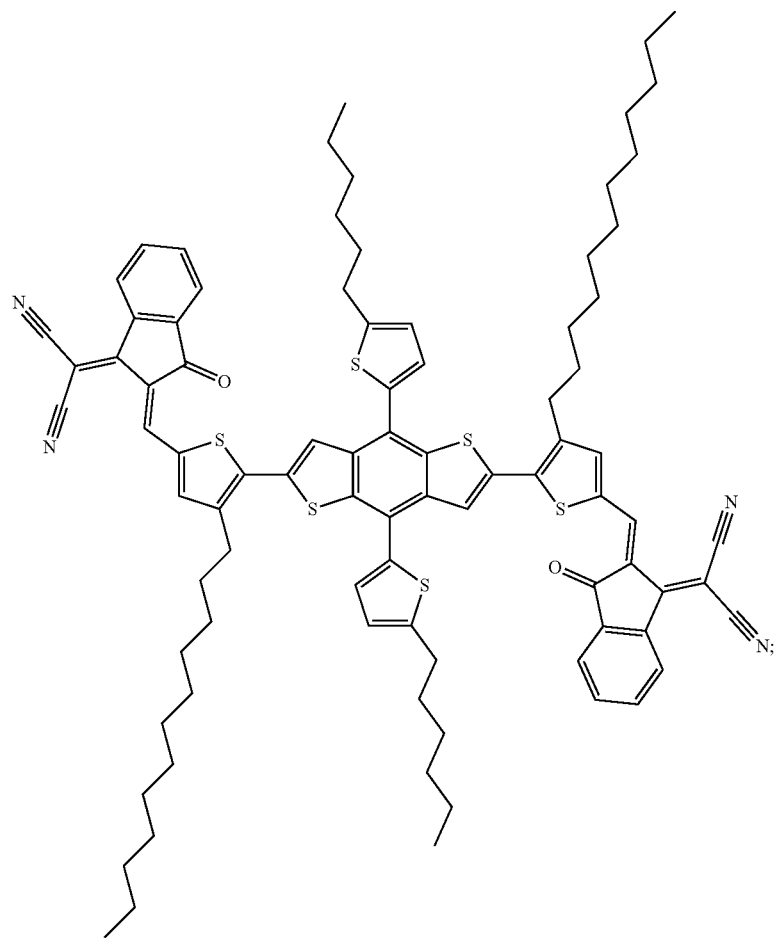
(2-11)
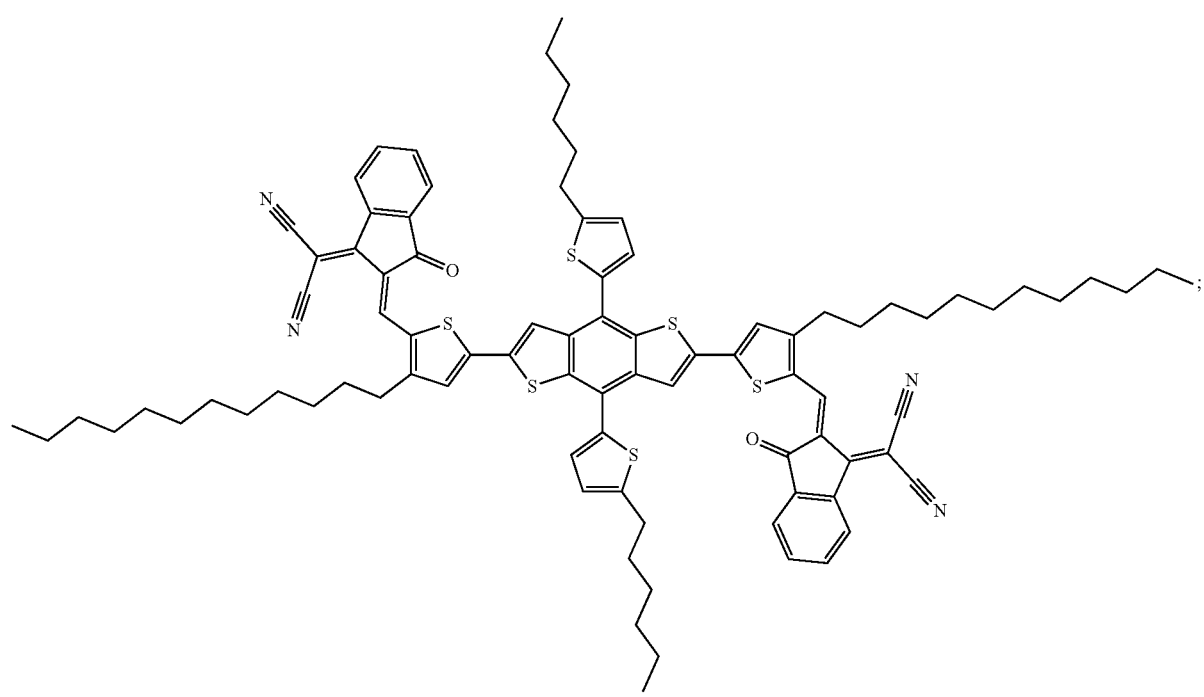

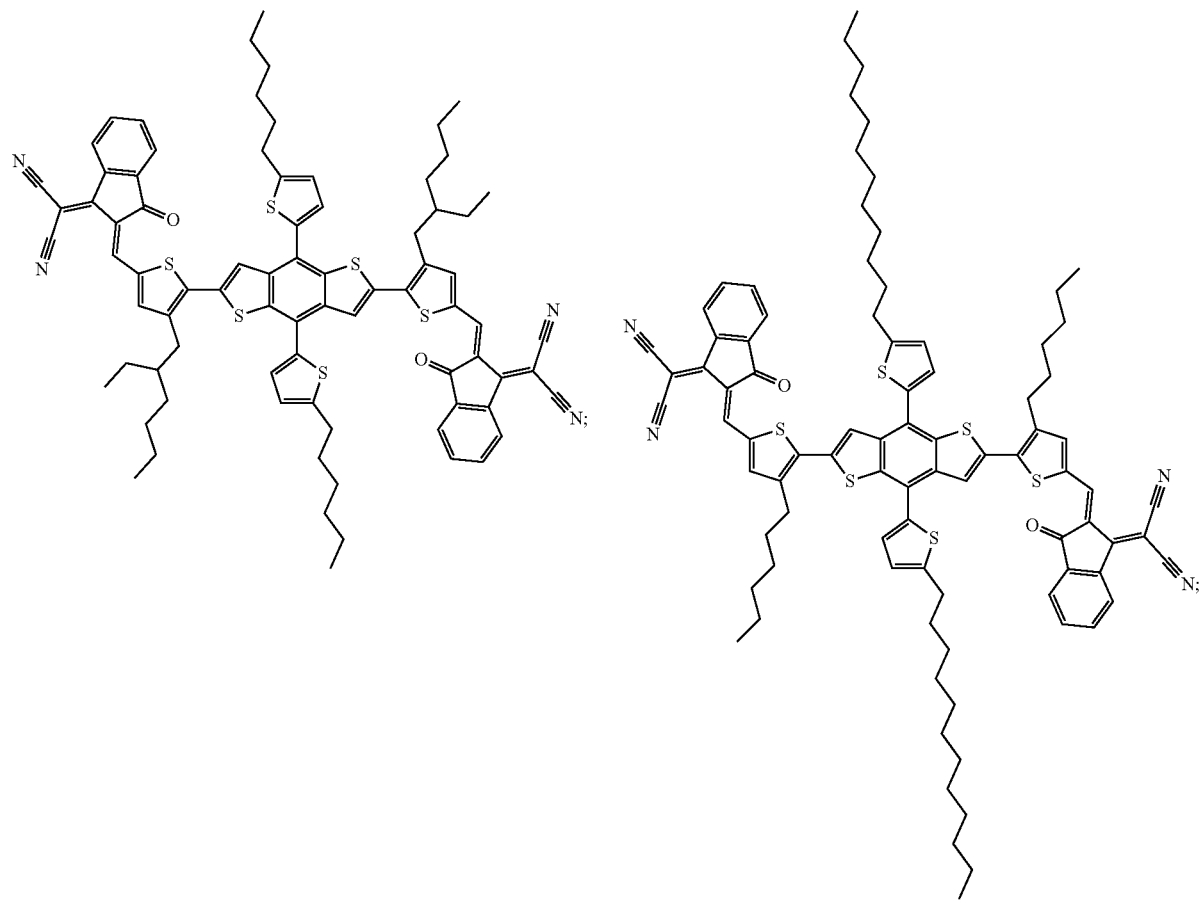

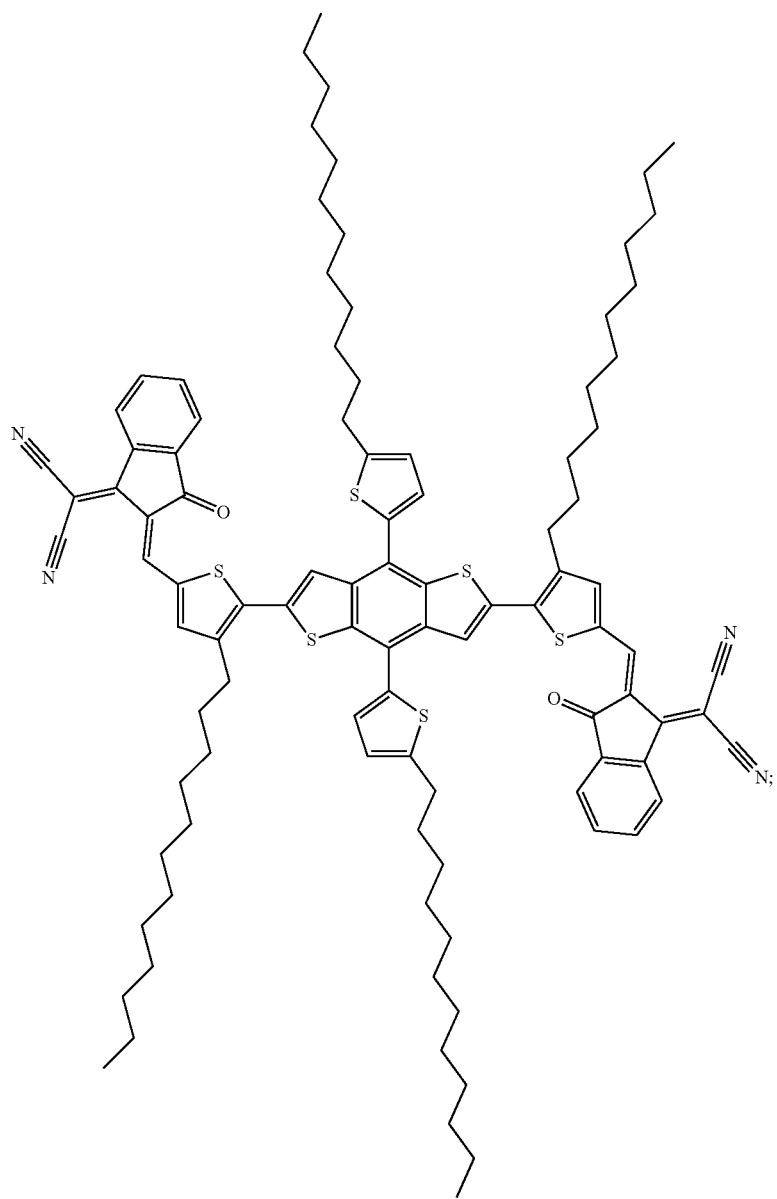
(2-14)

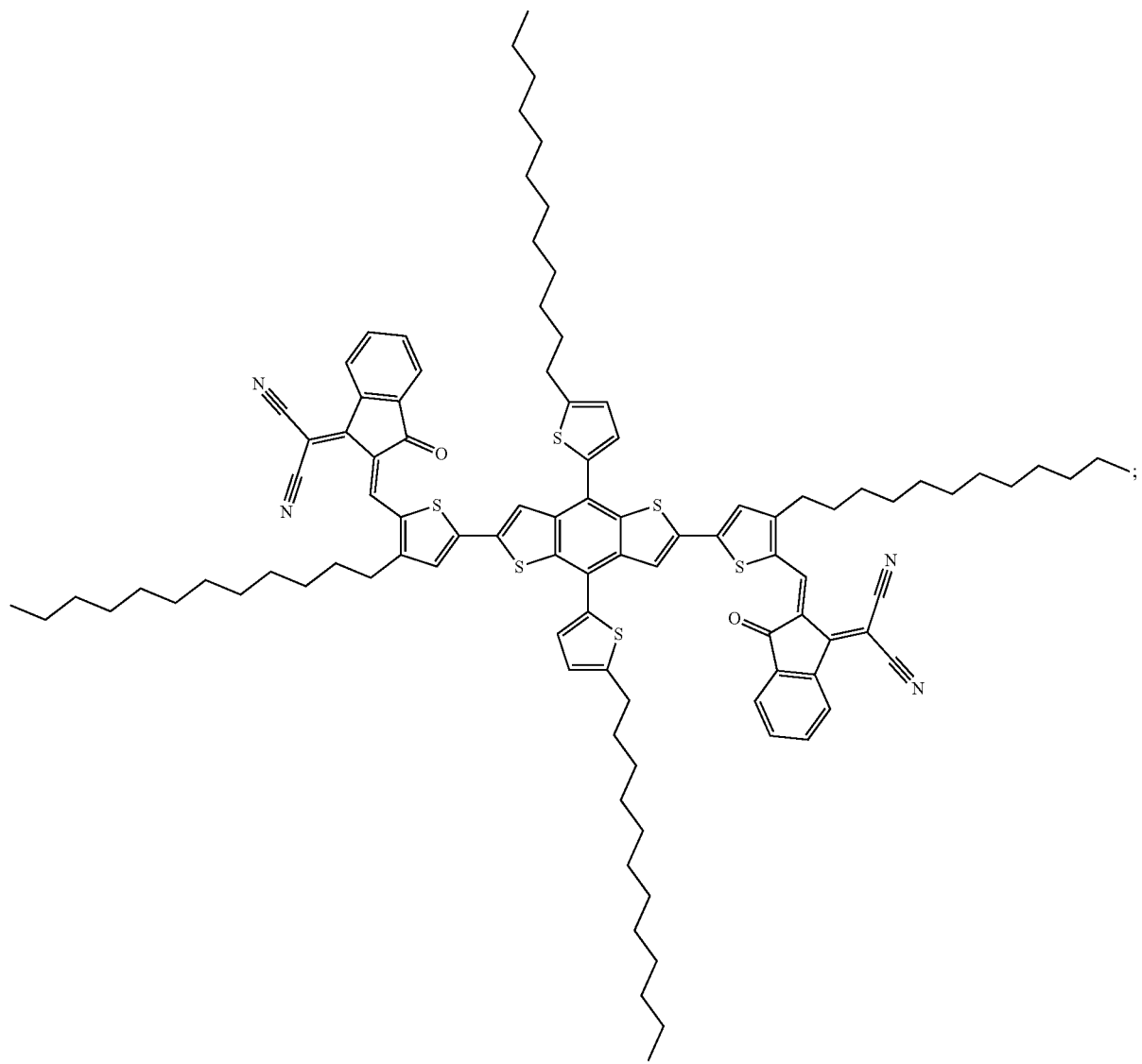
(2-15)

(2-16)
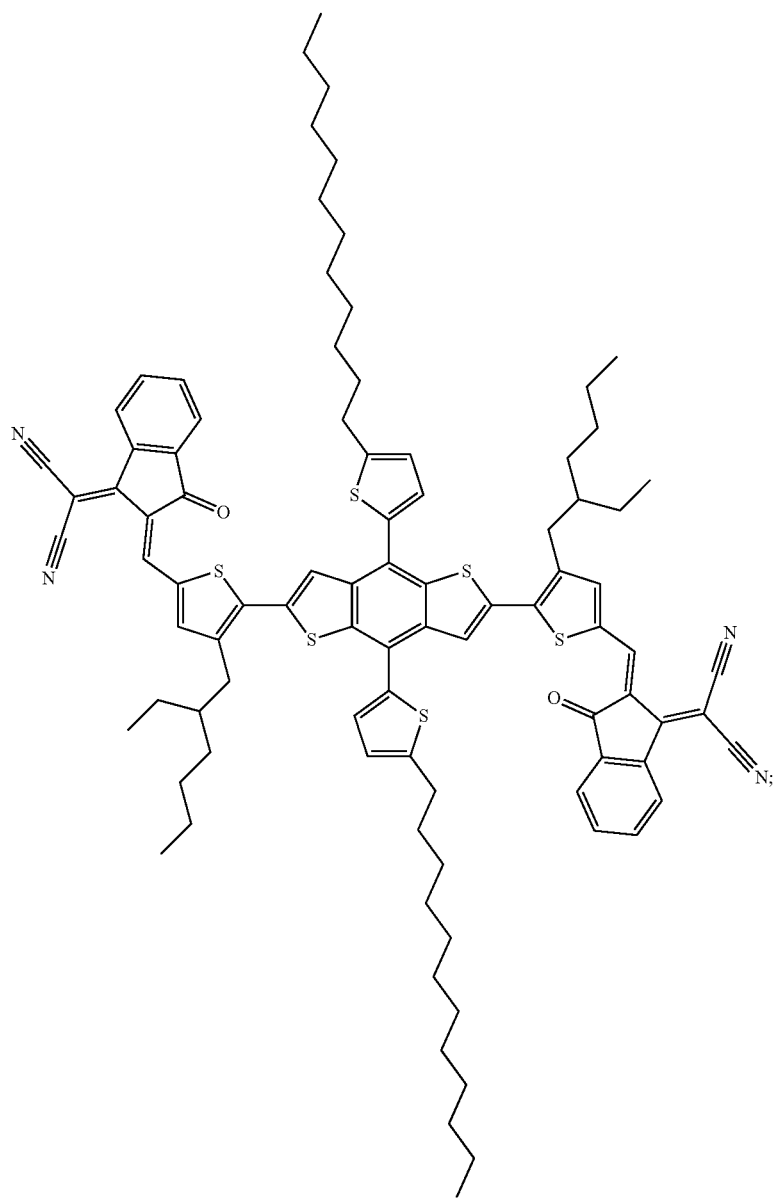

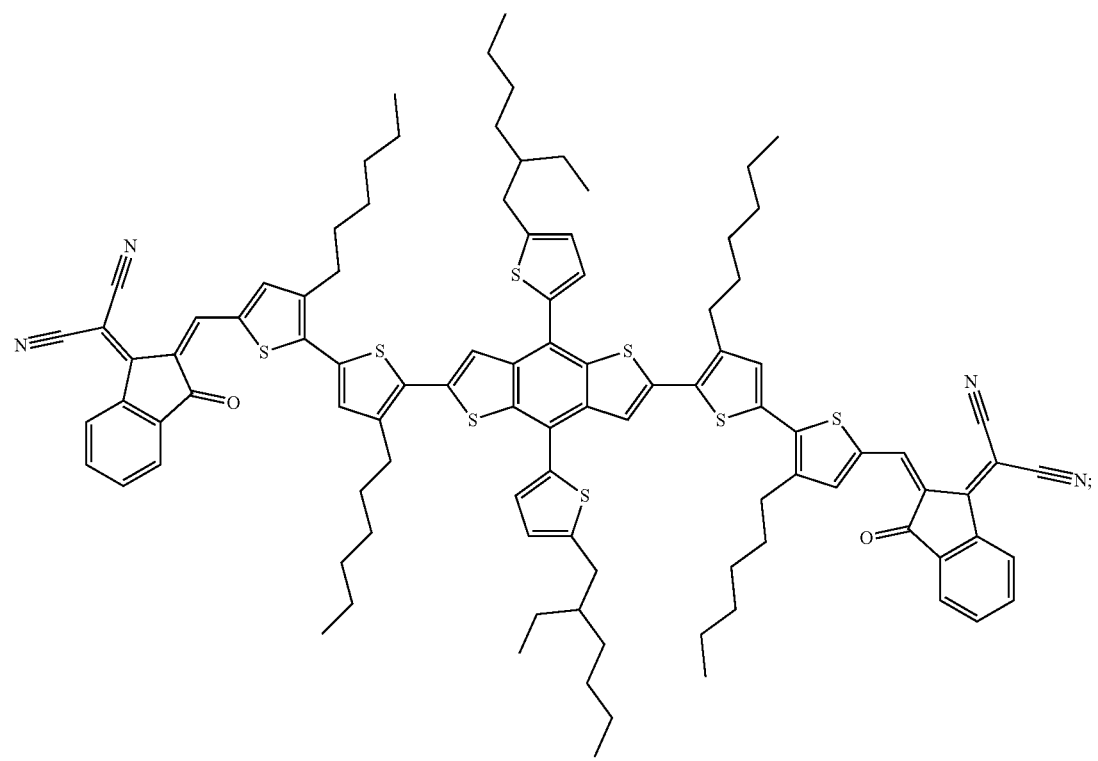
(2-17)

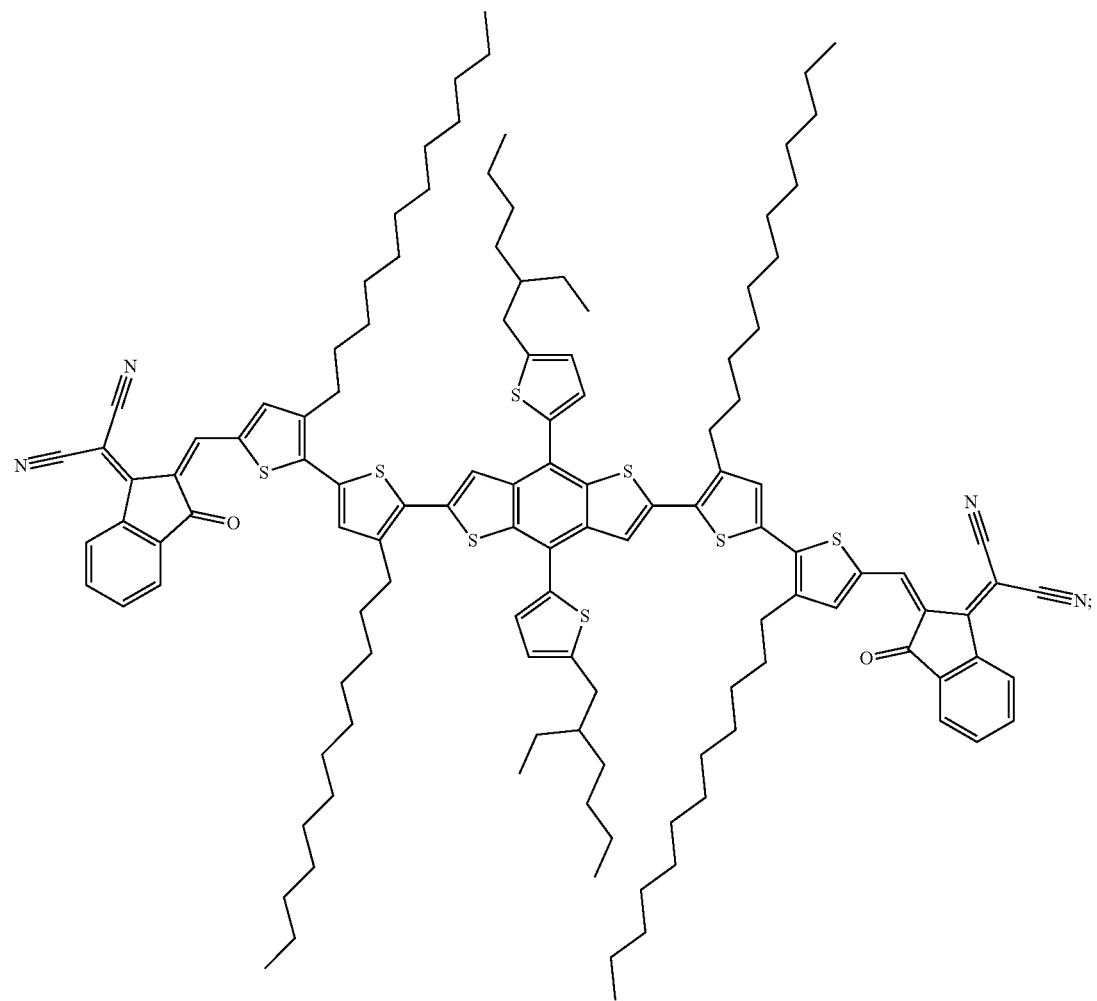
(2-18)

(2-19)
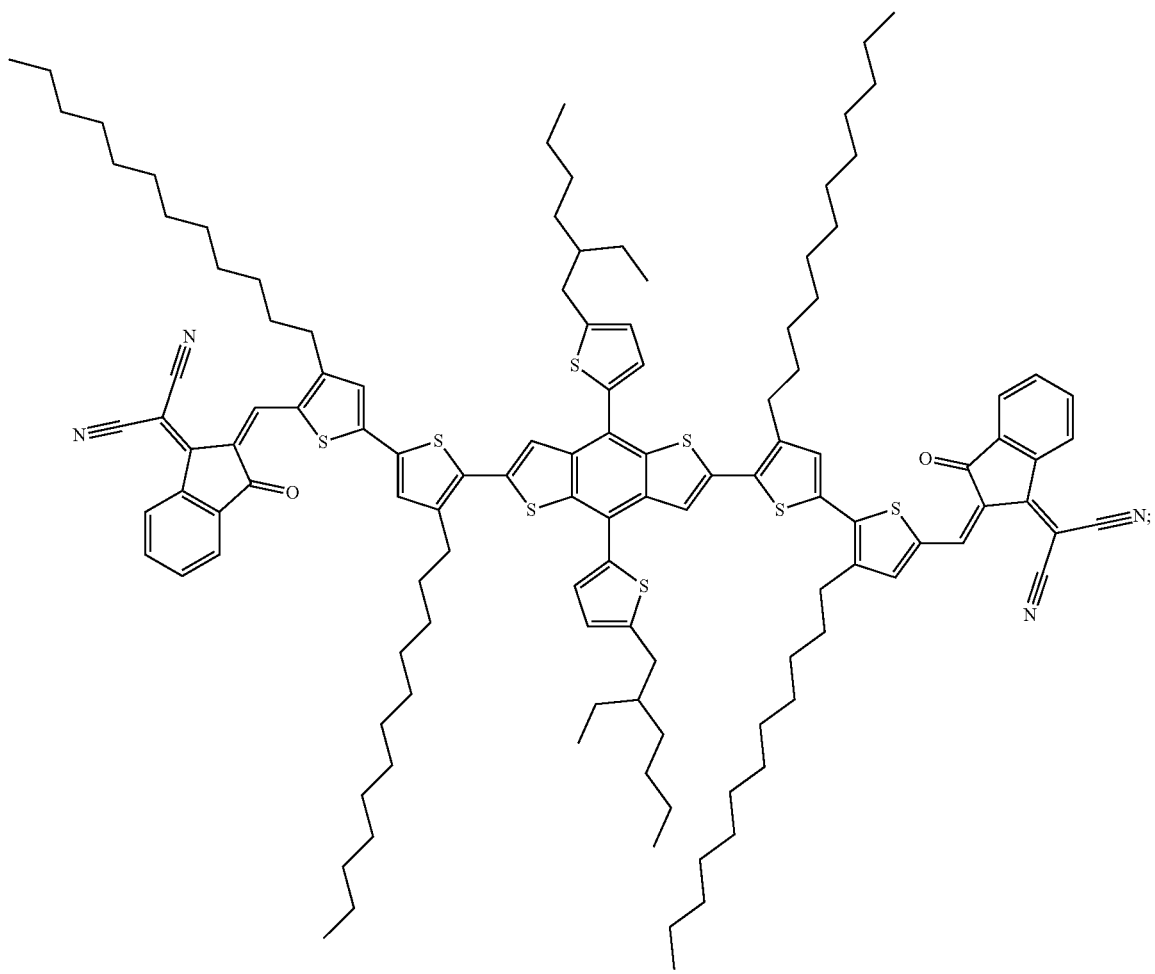

(2-20)
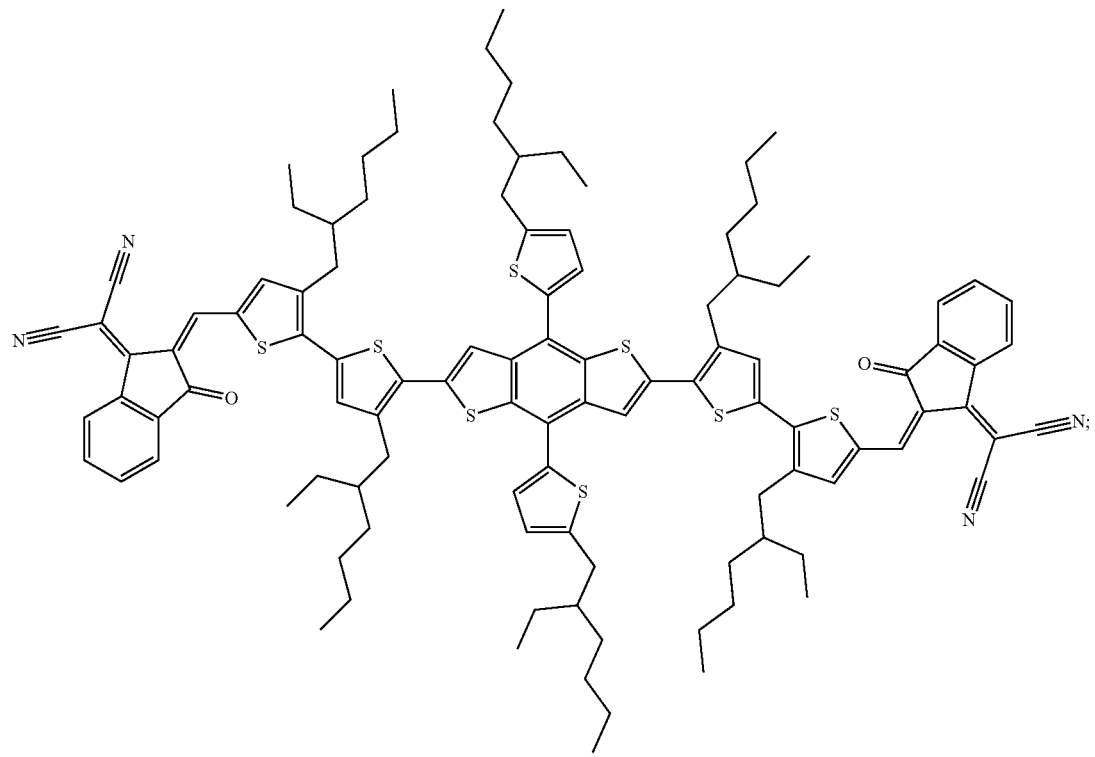
(2-21)
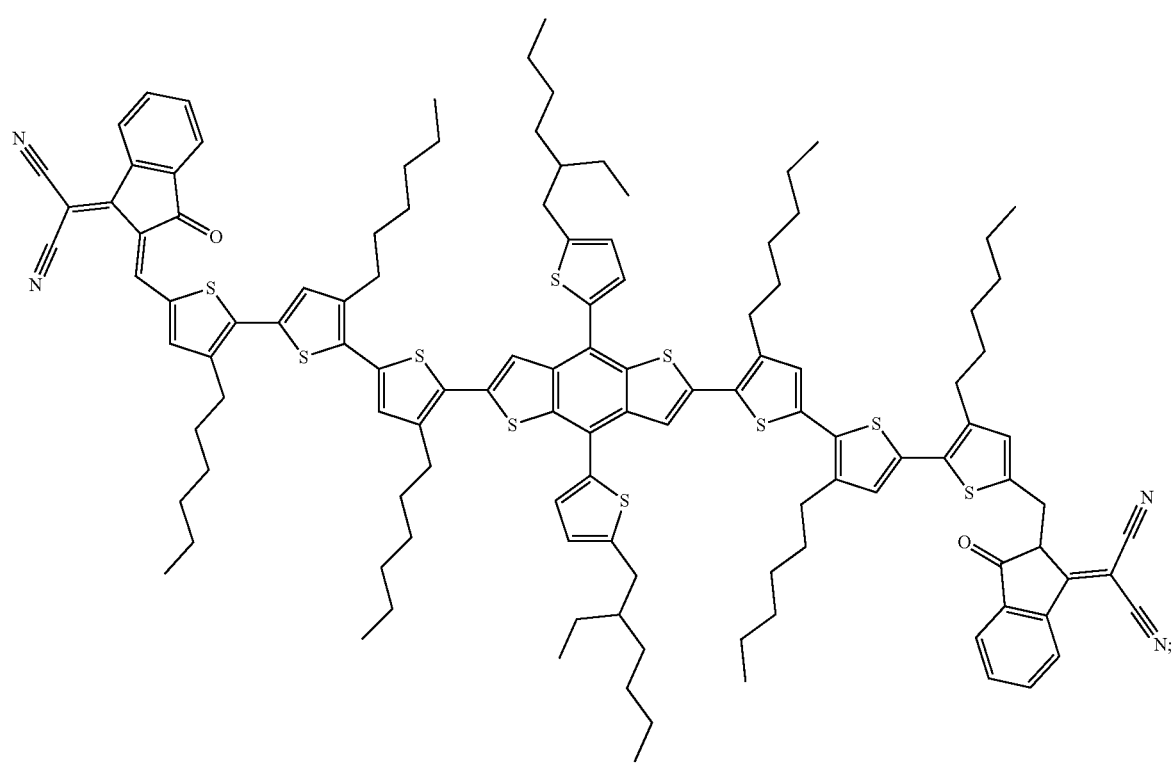

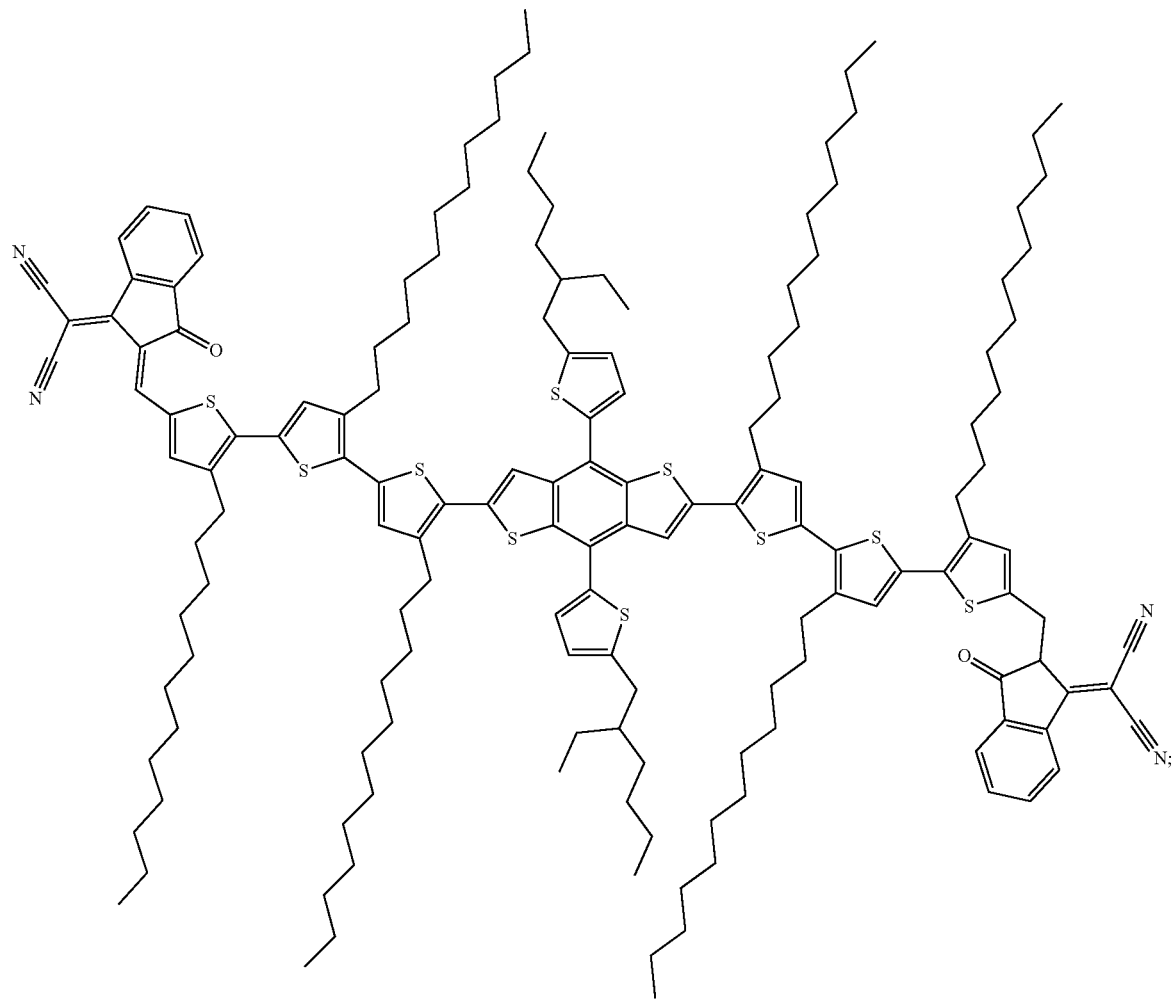
(2-22)

(2-23)
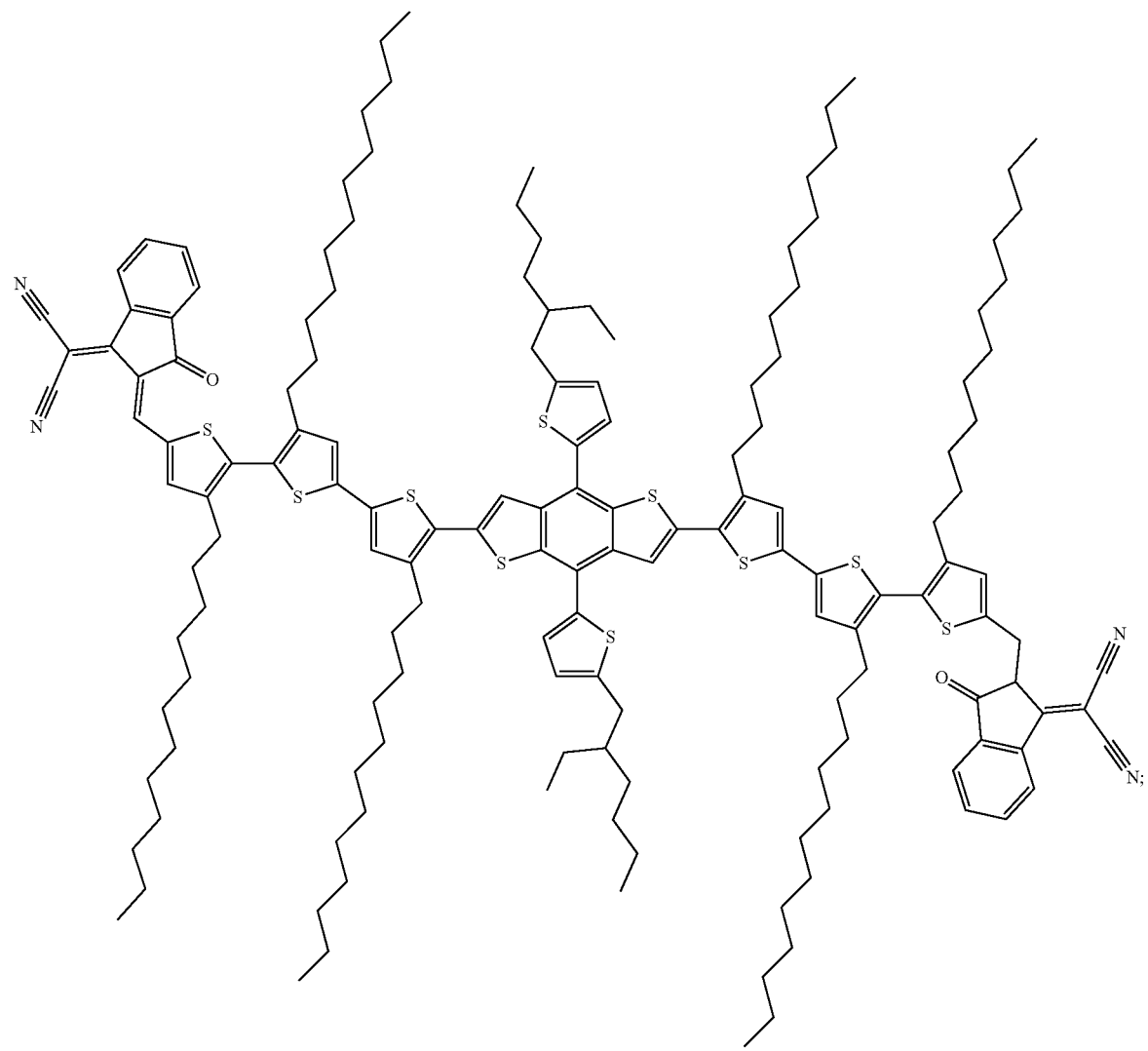

-continued (2-24)

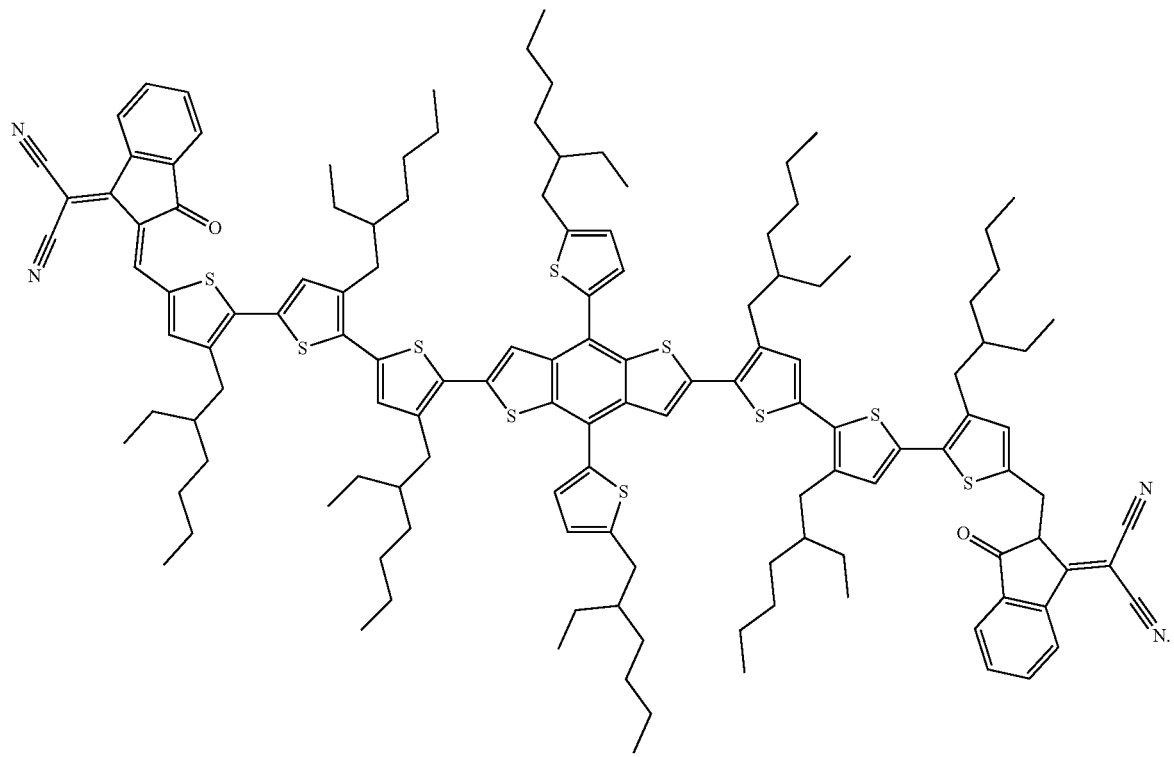

3. A thin organic-material film comprising:
   the organic compound according to claim 1; and
   a n-type organic material.

4. The thin organic-material film according to claim 3, wherein the n-type organic material is a fullerene derivative.

5. A photoelectric conversion layer, comprising the thin organic-material film according to claim 3.

6. A solution for forming a photoelectric conversion layer, the solution comprising:
   the organic compound according to claim 1;
   a n-type organic material; and
   an organic solvent.

7. The solution for forming a photoelectric conversion layer according to claim 6, wherein the n-type organic material is a fullerene derivative.

8. A photoelectric conversion element comprising:
   a substrate;
   a first electrode;
   an electron-transporting layer;
   a photoelectric conversion layer;
   a hole-transporting layer; and
   a second electrode, where the first electrode, the electron-transporting layer, the photoelectric conversion layer, the hole-transporting layer, and the second electrode are disposed on the substrate in this order,
   wherein the photoelectric conversion layer is the photoelectric conversion layer according to claim 5.

9. A photoelectric conversion element comprising:
   a substrate;
   a first electrode;
   a hole-transporting layer;
   a photoelectric conversion element;
   an electron-transporting layer; and
   a second electrode, where the first electrode, the hole-transporting layer, the photoelectric conversion element, the electron-transporting layer, and the second electrode are disposed on the substrate in this order,
   wherein the photoelectric conversion layer is the photoelectric conversion layer according to claim 5.

10. The photoelectric conversion element according to claim 8, wherein the electron-transporting layer contains metal oxide.

11. A photoelectric conversion element comprising:
    a first electrode;
    a second electrode; and
    a photoelectric conversion layer disposed between the first electrode and the second electrode,
    wherein the photoelectric conversion layer contains the organic compound according to claim 2.

12. The photoelectric conversion element according to claim 11, wherein the photoelectric conversion layer further contains a n-type organic semiconductor.

13. The photoelectric conversion element according to claim 12, wherein the n-type organic semiconductor is a fullerene derivative.

14. The photoelectric conversion element according to claim 11, wherein the first electrode, an electron-transporting layer, the photoelectric conversion layer, a hole-transporting layer, and the second electrode are disposed on a substrate in this order.

15. The photoelectric conversion element according to claim 11, wherein the first electrode, a hole-transporting layer, the photoelectric conversion layer, an electron-transporting layer, and the second electrode are disposed on a substrate in this order.

16. The photoelectric conversion element according to claim 12, wherein the first electrode, an electron-transporting layer, the photoelectric conversion layer, a hole-transporting layer, and the second electrode are disposed on a substrate in this order.

17. The photoelectric conversion element according to claim 12, wherein the first electrode, a hole-transporting layer, the photoelectric conversion layer, an electron-transporting layer, and the second electrode are disposed on a substrate in this order.

18. The photoelectric conversion element according to claim 13, wherein the first electrode, an electron-transporting layer, the photoelectric conversion layer, a hole-transporting layer, and the second electrode are disposed on a substrate in this order.

19. The photoelectric conversion element according to claim 13, wherein the first electrode, a hole-transporting layer, the photoelectric conversion layer, an electron-transporting layer, and the second electrode are disposed on a substrate in this order.

20. A photoelectric conversion element comprising:
a substrate;
a first electrode;
an electron-transporting layer;
a photoelectric conversion layer including a first photoelectric conversion layer, an intermediate electrode and a second photoelectric conversion layer;
a hole-transporting layer; and
a second electrode, where the first electrode, the electron-transporting layer, the first photoelectric conversion layer in contact with the electron-transporting layer, the intermediate electrode and the second photoelectric conversion layer, the hole-transporting layer in contact with the second photoelectric conversion layer, and the second electrode are disposed on the substrate in this order,
wherein the electron-transporting layer includes at least one of an electron-accepting organic material, zinc oxide, titanium oxide and lithium fluoride,
wherein the hole-transporting layer includes at least one of an aromatic amine derivative and a hole-transporting inorganic compound,
wherein the first photoelectric conversion layer has a different absorption wavelength than that of the second photoelectric conversion layers, and
wherein one of the first photoelectric conversion layer and the second photoelectric conversion layer includes an organic compound represented by one of the following formulas (1-1), (1-3), (2-1) and (2-2) and stereoisomers thereof and the other of the first photoelectric conversion layer and the second photoelectric conversion layer includes an organic compound different than said organic compound represented by one of the formulas (1-1), (1-3), (2-1) and (2-2) and stereoisomers thereof:

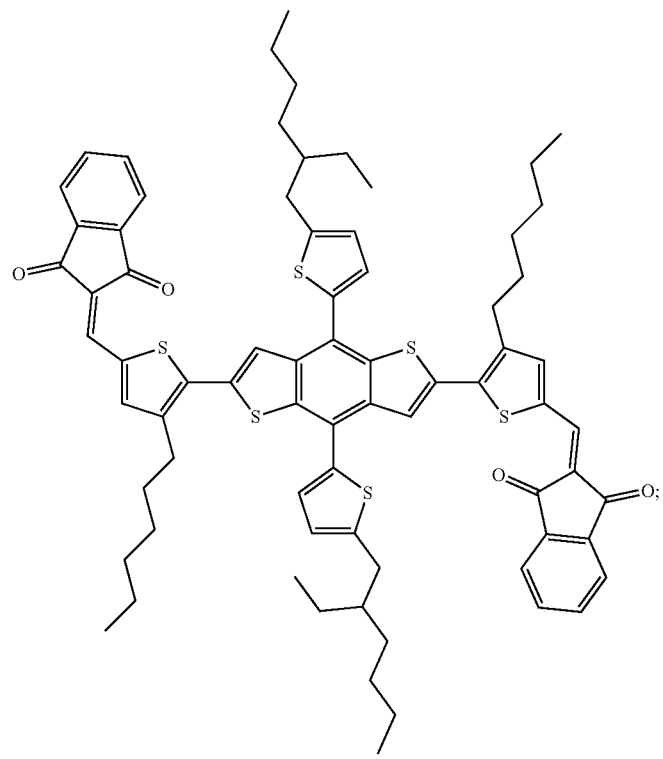

(1-1)

(1-3)

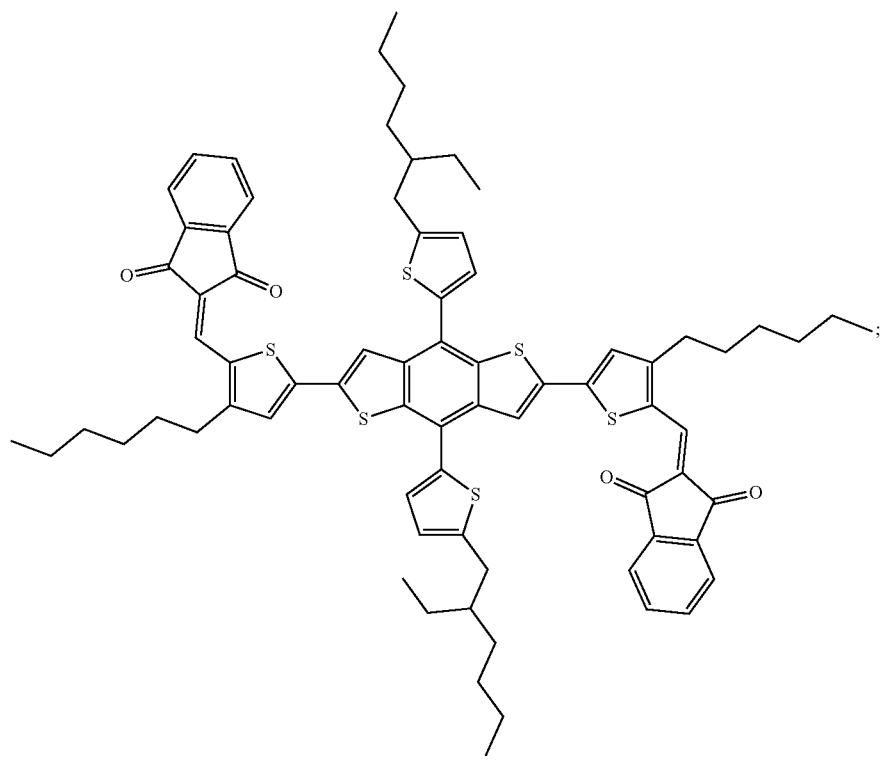

(2-2)

(2-1)

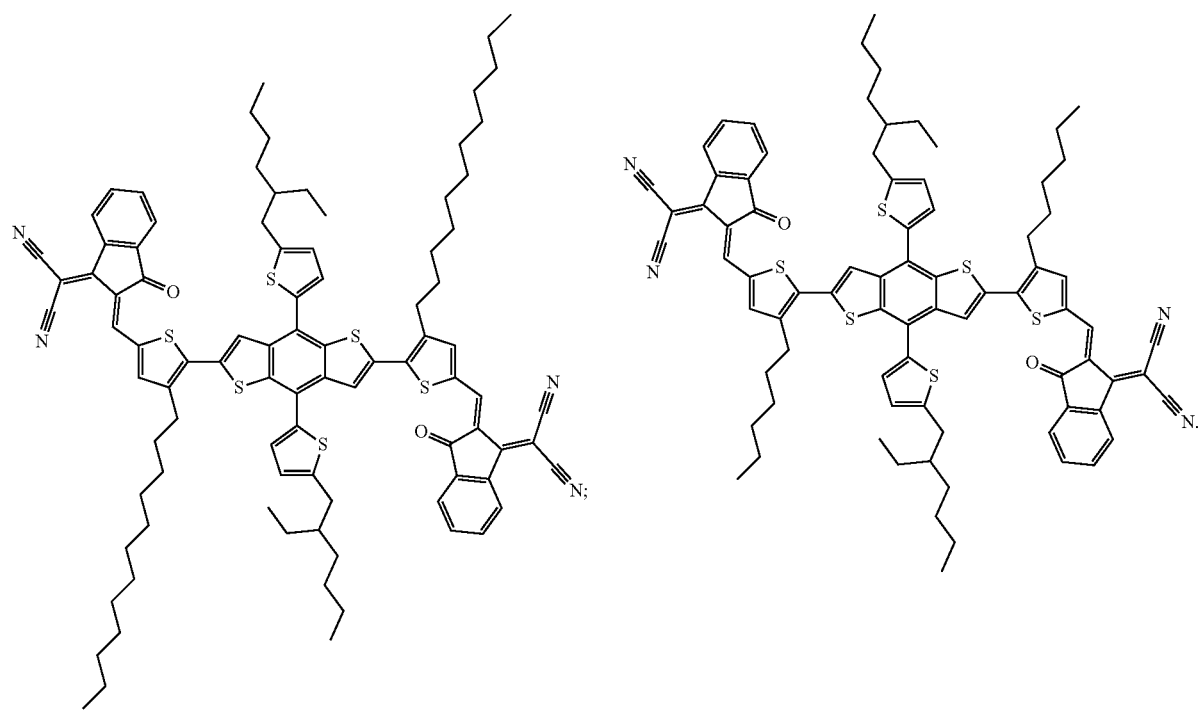

21. A photoelectric conversion element comprising:
a substrate;
a first electrode;
a hole-transporting layer;
a photoelectric conversion layer including a first photoelectric conversion layer, an intermediate electrode, a second photoelectric conversion layer;
an electron-transporting layer; and
a second electrode, where the first electrode, the hole-transporting layer, the first photoelectric conversion layer in contact with the hole-transporting layer, the intermediate electrode and the second photoelectric conversion layer, the electron-transporting layer in contact with the second photoelectric conversion layer, and the second electrode are disposed on the substrate in this order, wherein the electron-transporting layer includes at least one of an electron-accepting organic material, zinc oxide, titanium oxide and lithium fluoride, wherein the hole-transporting layer includes at least one of an aromatic amine derivative and a hole-transporting inorganic compound, wherein the first photoelectric conversion layer has a different absorption wavelength than that of the second photoelectric conversion layer, and wherein one of the first photoelectric conversion layer and the second photoelectric conversion layer includes an organic compound represented by one of the following formulas (1-1), (1-3), (2-1) and (2-2) and stereoisomers thereof and the other of the first photoelectric conversion layer and the second photoelectric conversion layer includes an organic compound different than said organic compound represented by one of the formulas (1-1), (1-3), (2-1) and (2-2) and stereoisomers thereof:

(1-1)

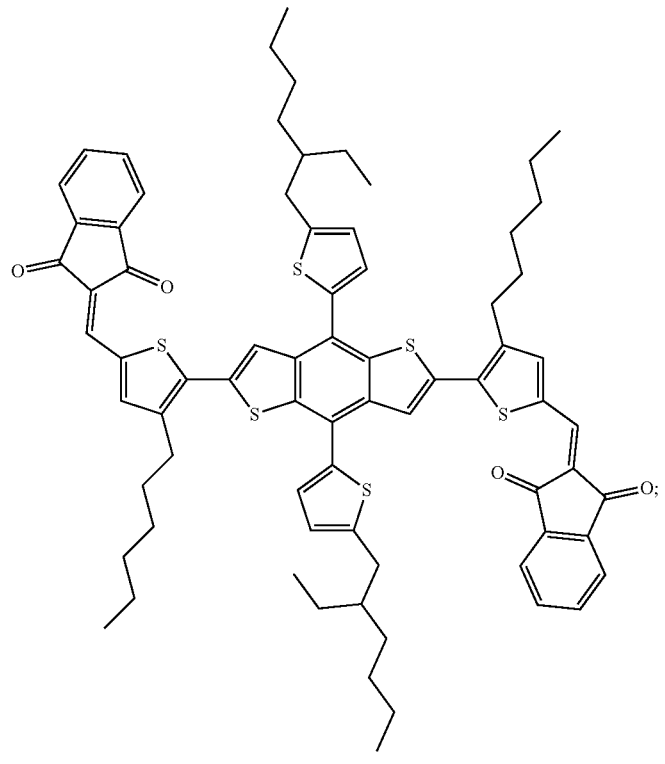

(1-3)

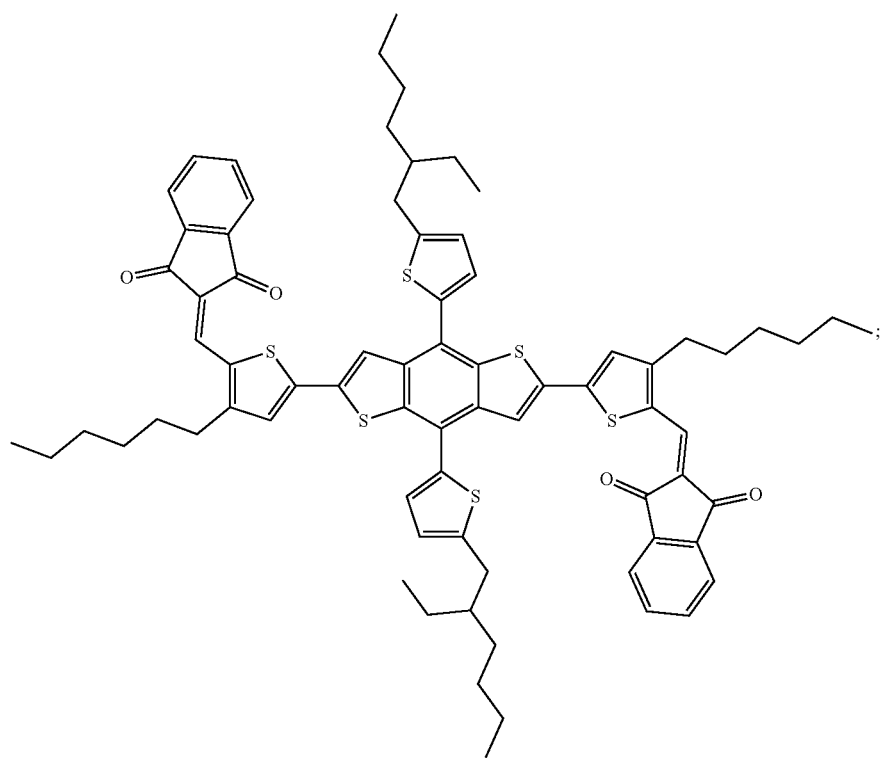

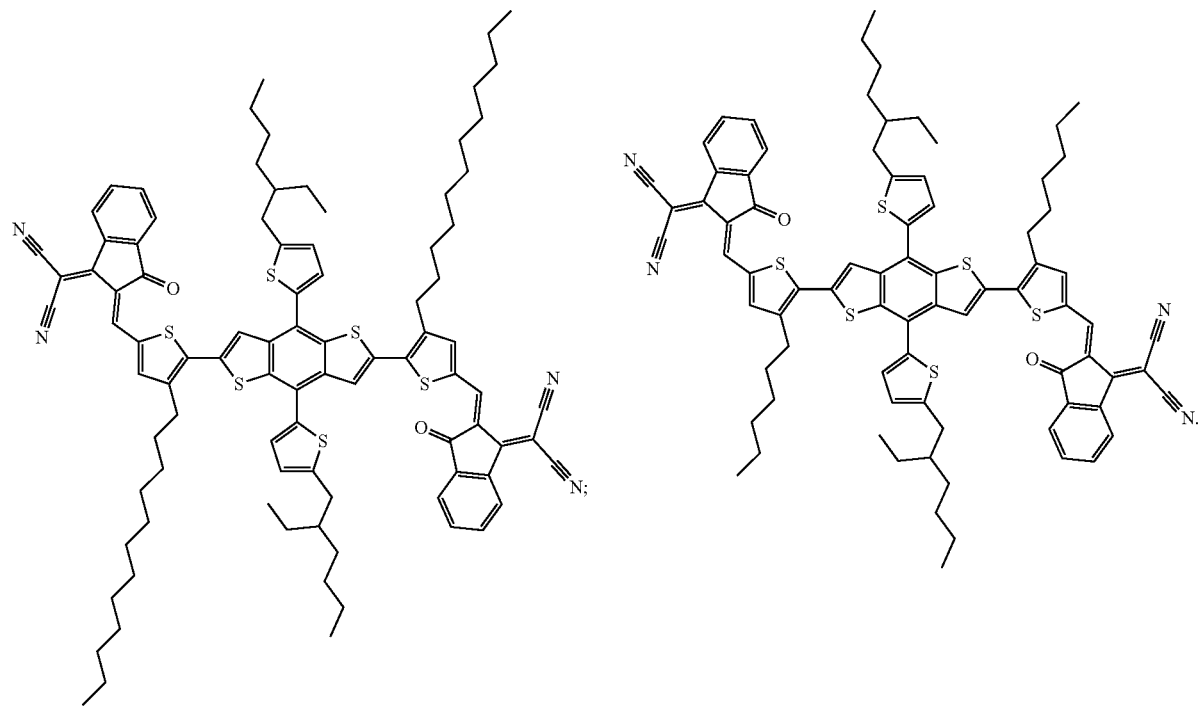
* * * * *